(12) United States Patent
Goldman

(10) Patent No.: US 12,258,569 B2
(45) Date of Patent: Mar. 25, 2025

(54) TRANSGENIC PLANTS WITH ENHANCED TRAITS

(71) Applicant: Monsanto Technology LLC, St. Louis, MO (US)

(72) Inventor: Barry S. Goldman, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 18/469,071

(22) Filed: Sep. 18, 2023

(65) Prior Publication Data

US 2024/0002872 A1    Jan. 4, 2024

Related U.S. Application Data

(60) Division of application No. 17/506,900, filed on Oct. 21, 2021, now abandoned, which is a continuation of application No. 16/417,505, filed on May 20, 2019, now Pat. No. 11,168,333, which is a continuation of application No. 15/532,681, filed as application No. PCT/US2015/063306 on Dec. 2, 2015, now Pat. No. 10,323,253.

(60) Provisional application No. 62/086,918, filed on Dec. 3, 2014.

(51) Int. Cl.
*C12N 15/82* (2006.01)

(52) U.S. Cl.
CPC ..... *C12N 15/8261* (2013.01); *C12N 15/8237* (2013.01); *C12N 15/8243* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 2006/0075522 A1* | 4/2006 | Cleveland | C12N 15/8273 800/294 |
| 2008/0090998 A1 | 4/2008 | Abad et al. | |
| 2012/0005773 A1 | 1/2012 | Aasen et al. | |
| 2012/0246748 A1 | 9/2012 | Guo et al. | |
| 2016/0369295 A1 | 12/2016 | Allen et al. | |

FOREIGN PATENT DOCUMENTS

| | | |
|---|---|---|
| WO | 1995002060 A1 | 1/1995 |
| WO | 01/07596 A1 | 2/2001 |
| WO | 2014102773 A1 | 7/2014 |

OTHER PUBLICATIONS

Whisstock J.C. et al. Prediction of protein function from protein sequence and structure. Q Rev Biophys. Aug. 2003;36(3):307-40. Review. (Year: 2003).*
Whisstock, J.C., et al., Prediction of protein function from protein sequence and structure. Q Rev Biophys. Aug;36(3):307-40 Review. (Year: 2003).
Ueguchi-Tanaka, et al., Gibberellin Insensitive DWARF1 encodes a soluble receptor for gibberellin. Nature. Sep. 29, 2005;437(7059):693-8. (Year: 2005).
Nishimura, et al., OsPNH1 Regulates Leaf Development and Maintenance of the Shoot Apical Meristem in Rice Plant J. Apr. 2002;30(2):189-201. (Year: 2002).
Hiei, et al., Efficient Transformation of Rice (*Oryza Sativa* L.) Mediated by Agrobacterium and Sequence Analysis of the Boundaries of the T-DNA Plant J. Aug. 1994;6(2):271-82. (Year: 1994).

* cited by examiner

*Primary Examiner* — Cynthia E Collins
(74) *Attorney, Agent, or Firm* — Dentons US LLP; Paula DeGrandis

(57) ABSTRACT

This disclosure provides recombinant DNA constructs and transgenic plants having enhanced traits such as increased yield, increased nitrogen use efficiency and enhanced drought tolerance; propagules, progeny and field crops of such transgenic plants; and methods of making and using such transgenic plants. This disclosure also provides methods of producing seed from such transgenic plants, growing such seed and selecting progeny plants with enhanced traits. Also disclosed are transgenic plants with altered phenotypes which are useful for screening and selecting transgenic events for the desired enhanced trait.

11 Claims, No Drawings
Specification includes a Sequence Listing.

TRANSGENIC PLANTS WITH ENHANCED TRAITS

CROSS REFERENCE TO RELATED APPLICATION

This application is a divisional of U.S. patent application Ser. No. 17/506,900, filed Oct. 21, 2021, which is a continuation of U.S. patent application Ser. No. 16/417,505, filed May 20, 2019, now U.S. Pat. No. 11,168,333, which is a continuation of U.S. patent application Ser. No. 15/532,681, filed Jun. 2, 2017, now U.S. Pat. No. 10,323,253, which is a U.S. National Stage Entry of PCT/US2015/063306, filed Dec. 2, 2015, which claims the benefit under 35 USC § 119(e) of U.S. provisional application Ser. No. 62/086,918, filed on Dec. 3, 2014, each of which is herein incorporated by reference in its entirety.

INCORPORATION OF SEQUENCE LISTING

The sequence listing file named "MONS421USD1_ST26", which is 170 kilobytes (measured in MS-WINDOWS) and was created on Sep. 15, 2023, is filed herewith and incorporated herein by reference in its entirety.

FIELD OF THE INVENTION

Disclosed herein are recombinant DNA constructs, plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

In one aspect, the disclosure provides a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-27 and 55;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6 and 55-60;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 28-54, 61, 79-96; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 33, 61-66, 82, and 96.

In another aspect, the disclosure provides a suppression recombinant DNA construct that transcribes into a double-stranded RNA, an antisense RNA, a miRNA or a ta-siRNA.

In another aspect, the disclosure provides a suppression recombinant DNA construct that transcribes into a miRNA precursor that produces a mature miRNA having a nucleic acid sequence with at least 95%, at least 96%, at least 97%, at least 98%, at least 99%, or 100% identity to a fragment of at least 19, 20, 21, 22, 23, 24, 25, 26 or 27 consecutive nucleotides of a sequence selected from the group consisting of SEQ ID NOs: 6 and 55-60.

In another aspect, the disclosure provides a suppression recombinant DNA construct that transcribes into a miRNA precursor that produces a mature miRNA having a nucleic acid sequence with at least 95%, at least 96%, at least 97%, at least 98%, at least 99%, or 100% complementarity to a fragment of at least 19, 20, 21, 22, 23, 24, 25, 26 or 27 consecutive nucleotides of a sequence selected from the group consisting of SEQ ID NOs: 6 and 55-60.

In another aspect, the disclosure provides a suppression recombinant DNA construct that transcribes into a miRNA precursor that produces a mature miRNA having a nucleic acid sequence with 100% identity or 100% complementarity to a fragment of 21 consecutive nucleotides of a sequence selected from the group consisting of SEQ ID NOs: 6 and 55-60.

In another aspect, the disclosure provides a suppression recombinant DNA construct comprising a sequence selected from the group consisting of SEQ ID NOs: 67-72.

In another aspect, the disclosure provides a plant comprising a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-27 and 55;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6 and 55-60;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 28-54, 61, 79-96; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 33, 61-66, 82, and 96.

In another aspect, the disclosure provides a plant comprising a recombinant DNA construct of the present disclosure, and having at least one altered phenotype or at least one enhanced trait as compared to a control plant. Such phenotype is characterized or measured by anthocyanin content, biomass, canopy area, chlorophyll content, plant height, water applied, water content or water use efficiency. Such enhanced trait is increased yield, increased nitrogen use efficiency, or increased water use efficiency.

In another aspect, the disclosure provides a plant comprising a recombinant DNA construct of the present disclosure, wherein the plant is a progeny, a propagule, or a field crop.

In another aspect, the disclosure provides a field crop comprising a recombinant DNA construct of the present disclosure, wherein the field crop is selected from the group consisting of corn, soybean, cotton, canola, rice, barley, oat, wheat, turf grass, alfalfa, sugar beet, sunflower, quinoa and sugar cane.

In another aspect, the disclosure provides a propagule comprising a recombinant DNA construct the present disclosure, wherein the propagule is selected from the group consisting of cell, pollen, ovule, flower, embryo, leaf, root, stem, shoot, meristem, grain and seed.

In another aspect, the disclosure provides a plant comprising a recombinant DNA construct of the present disclosure, wherein the plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, Miscanthus plant, pampas grass plant, switchgrass (Panicum) plant, and/or teosinte plant, or is a member of the family Alliaceae, onion plant, leek plant, garlic plant; or wherein the plant is a dicot plant or is a member of the family Amaranthaceae, spinach plant, quinoa plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, papaya plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, eucalyptus plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, Capsicum plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, or spruce plant.

In another aspect, the disclosure provides a method for increasing yield, increasing nitrogen use efficiency, or increasing water use efficiency in a plant comprising producing a plant comprising a recombinant DNA construct comprising a heterologous promoter functional in a plant cell and operably linked to:
  a) a polynucleotide that comprises a nucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-27 and 55;
  b) a DNA encoding RNA for suppressing the expression of a target mRNA transcribed from a polynucleotide having a nucleic acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 6 and 55-60;
  c) a polynucleotide that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 28-54, 61, 79-96; or
  d) a DNA encoding RNA for suppressing the expression of a target protein having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 33, 61-66, 82, and 96.

In another aspect, the disclosure provides a method for producing a plant by transforming a plant cell or tissue with the recombinant DNA construct of the present disclosure and regenerating a plant from said cell or tissue containing said recombinant DNA construct. In another aspect, the disclosure provides a method for producing a plant by crossing said plant through breeding with:
  a) itself;
  b) a second plant from the same plant line;
  c) a wild type plant; or
  d) a second plant from a different line of plants
to produce a seed, growing said seed to produce a plurality of progeny plants; and selecting a progeny plant with increased yield, increased nitrogen use efficiency, or increased water use efficiency as compared to a control plant.

DETAILED DESCRIPTION OF THE INVENTION

In the attached sequence listing:

SEQ ID NOs 1 to 27 are nucleotide sequences of the coding strand of the DNA used in the recombinant DNA constructs imparting an enhanced trait in plants, each representing a coding sequence for a protein.

SEQ ID NOs 28 to 54 are amino acid sequences of the cognate proteins of the DNA molecules with nucleotide sequences of SEQ ID NOs 1 to 27 respectively in the same order.

SEQ ID NOs: 55 to 60 are nucleotide sequences, each representing a coding sequence of a suppression target gene.

SEQ ID NOs 61 to 66 are amino acid sequences of the cognate proteins of the DNA molecules with nucleotide sequences of SEQ ID NOs 55 to 60 respectively in the same order.

SEQ ID NOs 67 to 72 are nucleotide sequences of DNA molecules used in the recombinant DNA constructs imparting an enhanced trait or altered phenotype in plants, each representing an engineered miRNA precursor sequence.

SEQ ID NOs: 73 to 78 are nucleotide sequences of the target recognition sites of the engineered miRNA precursors with nucleotide sequences of SEQ ID NOs 67 to 72 respectively in the same order.

SEQ ID NOs 79 to 96 are amino acid sequences of proteins homologous to the proteins with amino acid sequences of SEQ ID NOs 28 to 54, and 61 to 66.

SEQ ID NOs 97 to 100 are nucleotide sequences of DNA molecules used in the recombinant DNA constructs imparting an enhanced trait or altered phenotype in plants, each representing a promoter with a specific expression pattern.

SEQ ID NOs 101 to 104 are nucleotide sequences of variants of a rice MIR gene.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotide of the DNA with uracil (U) nucleotide. Thus, providing a specific DNA sequence is understood to define the exact RNA equivalent. A given first polynucleotide sequence, whether DNA or RNA, further defines the sequence of its exact complement (which can be DNA or RNA), i. e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

As used herein, the term "expression" refers to the production of a polynucleotide or a protein by a plant, plant cell or plant tissue which can give rise to an altered phenotype or enhanced trait. Expression can also refer to the process by which information from a gene is used in the synthesis of functional gene products, which may include but are not limited to other polynucleotides or proteins which may serve, e.g., an enzymatic, structural or regulatory function. Gene products having a regulatory function include but are not limited to elements that affect the occurrence or level of transcription or translation of a target protein. In some cases, the expression product is a non-coding functional RNA.

"Modulation" of expression refers to the process of effecting either overexpression or suppression of a polynucleotide or a protein.

The term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. The term "target gene" as used in the context of suppression refers to either "target protein" or "target mRNA". In alternate non-limiting embodiments, the target protein or target polynucleotide is one the suppression of which can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby affect the altered phenotype or enhanced trait indirectly.

Suppression can be applied using numerous approaches. Non limiting examples include: suppressing an endogenous gene(s) or a subset of genes in a pathway, suppressing one or more mutation that has resulted in decreased activity of a protein, suppressing the production of an inhibitory agent, to elevate, reducing or eliminating the level of substrate that an enzyme requires for activity, producing a new protein, activating a normally silent gene; or accumulating a product that does not normally increase under natural conditions.

Conversely, the term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. The term "target gene" as used in the context of overexpression refers to either "target protein" or "target mRNA". In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides or polypeptides under the control of a promoter, examples of which include but are not limited to endogenous promoters, heterologous promoters, inducible promoters and tissue specific promoters. In one exemplary embodiment, the promoter is a constitutive promoter, for example, the cauliflower mosaic virus 35S transcription initiation region. Thus, depending on the promoter used, overexpression can occur throughout a plant, in specific tissues of the plant, or in the presence or absence of different inducing or inducible agents, such as hormones or environmental signals.

Gene Suppression Elements: The gene suppression element can be transcribable DNA of any suitable length, and generally includes at least about 19 to about 27 nucleotides (for example 19, 20, 21, 22, 23, or 24 nucleotides) for every target gene that the recombinant DNA construct is intended to suppress. In many embodiments the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress.

Suitable gene suppression elements useful in the recombinant DNA constructs of the invention include at least one element (and, in some embodiments, multiple elements) selected from the group consisting of:

(a) DNA that includes at least one anti-sense DNA segment that is anti-sense to at least one segment of the at least one first target gene; (b) DNA that includes multiple copies of at least one anti-sense DNA segment that is anti-sense to at least one segment of the at least one first target gene; (c) DNA that includes at least one sense DNA segment that is at least one segment of the at least one first target gene; (d) DNA that includes multiple copies of at least one sense DNA segment that is at least one segment of the at least one first target gene; (e) DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene; (t) DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene; (g) DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats; (h) DNA that includes nucleotides derived from a miRNA, preferably a plant miRNA; (i) DNA that includes nucleotides of a siRNA; (j) DNA that transcribes to an RNA aptamer capable of binding to a ligand; and (k) DNA that transcribes to an RNA aptamer capable of binding to a ligand, and DNA that transcribes to regulatory RNA capable of regulating expression of the first target gene, wherein the regulation is dependent on the conformation of the regulatory RNA, and the conformation of the regulatory RNA is allosterically affected by the binding state of the RNA aptamer.

Any of these gene suppression elements, whether transcribing to a single double-stranded RNA or to multiple double-stranded RNAs, can be designed to suppress more than one target gene, including, for example, more than one allele of a target gene, multiple target genes (or multiple segments of at least one target gene) from a single species, or target genes from different species.

Anti-Sense DNA Segments: In one embodiment, the at least one anti-sense DNA segment that is anti-sense to at least one segment of the at least one first target gene includes DNA sequence that is anti-sense or complementary to at least a segment of the at least one first target gene, and can include multiple anti-sense DNA segments, that is, multiple copies of at least one anti-sense DNA segment that is anti-sense to at least one segment of the at least one first target gene. Multiple anti-sense DNA segments can include DNA sequence that is anti-sense or complementary to multiple segments of the at least one first target gene, or to multiple copies of a segment of the at least one first target gene, or to segments of multiple first target genes, or to any combination of these. Multiple anti-sense DNA segments can be fused into a chimera, e.g., including DNA sequences that are anti-sense to multiple segments of one or more first target genes and fused together.

The anti-sense DNA sequence that is anti-sense or complementary to (that is, can form Watson-Crick base-pairs with) at least a segment of the at least one first target gene has at least about 80%, or at least about 85%, or at least about 90%, or at least about 95% complementarity to at least a segment of the at least one first target gene. In one embodiment, the DNA sequence that is anti-sense or complementary to at least a segment of the at least one first target gene has between about 95% to about 100% complementarity to at least a segment of the at least one first target gene. Where the at least one anti-sense DNA segment includes multiple anti-sense DNA segments, the degree of complementarity can be, but need not be, identical for all of the multiple anti-sense DNA segments.

Sense DNA Segments: In another embodiment, the at least one sense DNA segment that is at least one segment of the at least one first target gene includes DNA sequence that corresponds to (that is, has a sequence that is identical or substantially identical to) at least a segment of the at least one first target gene, and can include multiple sense DNA segments, that is, multiple copies of at least one sense DNA segment that corresponds to (that is, has the nucleotide sequence of) at least one segment of the at least one first target gene. Multiple sense DNA segments can include DNA sequence that is or that corresponds to multiple segments of the at least one first target gene, or to multiple copies of a segment of the at least one first target gene, or to segments of multiple first target genes, or to any combination of these. Multiple sense DNA segments can be fused into a chimera, that is, can include DNA sequences corresponding to multiple segments of one or more first target genes and fused together.

The sense DNA sequence that corresponds to at least a segment of the target gene has at least about 80%, or at least about 85%, or at least about 90%, or at least about 95% sequence identity to at least a segment of the target gene. In one embodiment, the DNA sequence that corresponds to at least a segment of the target gene has between about 95% to about 100% sequence identity to at least a segment of the target gene. Where the at least one sense DNA segment includes multiple sense DNA segments, the degree of sequence identity can be, but need not be, identical for all of the multiple sense DNA segments.

Multiple Copies: Where the gene suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segment can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement.

Double-stranded RNA: In those embodiments wherein the gene suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA may become double-stranded by the action of an RNA-dependent RNA polymerase. See, for example, U.S. Pat. No. 5,283,184, which is incorporated by reference herein.

In yet other embodiments, the gene suppression element can include DNA that transcribes to RNA for suppressing the at least one first target gene by forming double-stranded RNA and includes at least one anti-sense DNA segment that is anti-sense to at least one segment of the at least one target gene (as described above under the heading "Anti-sense DNA Segments") and at least one sense DNA segment that is at least one segment of the at least one first target gene (as described above under the heading "Sense DNA Segments"). Such a gene suppression element can further include spacer DNA segments. Each at least one anti-sense DNA segment is complementary to at least part of a sense DNA segment in order to permit formation of double-stranded RNA by intramolecular hybridization of the at least one anti-sense DNA segment and the at least one sense DNA segment. Such complementarity between an anti-sense DNA segment and a sense DNA segment can be, but need not be, 100% complementarity; in some embodiments, this complementarity can be preferably at least about 80%, or at least about 85%, or at least about 90%, or at least about 95% complementarity.

The double-stranded RNA can be in the form of a single dsRNA "stem" (region of base-pairing between sense and anti-sense strands), or can have multiple dsRNA "stems". In one embodiment, the gene suppression element can include DNA that transcribes to RNA for suppressing the at least one first target gene by forming essentially a single double-stranded RNA and includes multiple serial anti-sense DNA segments that are anti-sense to at least one segment of the at least one first target gene and multiple serial sense DNA segments that are at least one segment of the at least one first target gene; the multiple serial anti-sense and multiple serial sense segments can form a single double-stranded RNA "stem" or multiple "stems" in a serial arrangement (with or without non-base paired spacer DNA separating the multiple "stems"). In another embodiment, the gene suppression element includes DNA that transcribes to RNA for suppressing the at least one first target gene by forming multiple dsRNA "stems" of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of dsRNA "stems" (such as, but not limited to "inverted repeats"). Such multiple dsRNA "stems" can further be arranged in series or clusters to form tandem inverted repeats, or structures resembling "hammerhead" or "cloverleaf" shapes. Any of these gene suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segment are of unequal length, the longer segment can act as a spacer.

miRNAs: In a further embodiment, the gene suppression element can include DNA that includes nucleotides derived from a miRNA (microRNA), that is, a DNA sequence that corresponds to a miRNA native to a virus or a eukaryote of interest (including plants and animals, especially invertebrates), or a DNA sequence derived from such a native miRNA but modified to include nucleotide sequences that do not correspond to the native miRNA. While miRNAs have not to date been reported in fungi, fungal miRNAs, should they exist, are also suitable for use in the invention. An embodiment includes a gene suppression element containing DNA that includes nucleotides derived from a viral or plant miRNA.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e.g., the placement of mismatches in the stem structure of the pre-miRNA) is preserved to permit the pre-miRNA to be processed into a mature miRNA. In yet another embodiment, the gene suppression element can include DNA that includes nucleotides derived from a miRNA and capable of inducing or guiding in-phase cleavage of an endogenous transcript into trans-acting siRNAs, as described by Allen et al. (2005) Cell, 121:207-221, which is incorporated by reference in its entirety herein. Thus, the DNA that includes nucleotides derived from a miRNA can include sequence naturally occurring in a miRNA or a miRNA precursor molecule, synthetic sequence, or both.

siRNAs: In yet another embodiment, the gene suppression element can include DNA that includes nucleotides of a small interfering RNA (siRNA). The siRNA can be one or more native siRNAs (such as siRNAs isolated from a non-transgenic eukaryote or from a transgenic eukaryote), or can be one or more DNA sequences predicted to have siRNA activity (such as by use of predictive tools known in the art, see, for example, Reynolds et al. (2004) Nature Biotechnol., 22:326-330, which is incorporated by reference in its entirety herein). Multiple native or predicted siRNA sequences can be joined in a chimeric siRNA sequence for gene suppression. Such a DNA that includes nucleotides of a siRNA includes at least 19 nucleotides, and in some embodiments includes at least 20, at least 21, at least 22, at least 23, or at least 24 nucleotides. In other embodiments, the DNA that includes nucleotides of a siRNA can contain substantially more than 21 nucleotides, for example, more than about 50, about 100, about 300, about 500, about 1000, about 3000, or about 5000 nucleotides or greater.

Engineered miRNAs and trans-acting siRNAs (ta-siR-NAs) are useful for gene suppression with increased specificity. The invention provides recombinant DNA constructs, each including a transcribable engineered miRNA precursor designed to suppress a target sequence, wherein the transcribable engineered miRNA precursor is derived from the fold-back structure of a MIR gene, preferably a plant MIR sequence. These miRNA precursors are also useful for directing in-phase production of siRNAs (e.g., heterologous sequence designed to be processed in a trans-acting siRNA suppression mechanism in planta). The invention further provides a method to suppress expression of a target sequence in a plant cell, including transcribing in a plant cell a recombinant DNA including a transcribable engineered miRNA precursor designed to suppress a target sequence, wherein the transcribable engineered miRNA precursor is derived from the fold-back structure of a MIR gene, preferably a plant MIR sequence, whereby expression of the target sequence is suppressed relative to its expression in the absence of transcription of the recombinant DNA construct. In specifically claimed embodiments, the transcribable engineered miRNA precursor is derived from the fold-back structure of a rice MIR sequence selected from the group consisting of SEQ ID NOs. 101-104, and their complements.

The mature miRNAs produced, or predicted to be produced, from these miRNA precursors may be engineered for use in suppression of a target gene, e.g., in transcriptional suppression by the miRNA, or to direct in-phase production of siRNAs in a trans-acting siRNA suppression mechanism (see Allen et al. (2005) Cell, 121:207-221, Vaucheret (2005) Science STKE, 2005:pe43, and Yoshikawa et al. (2005) Genes Dev., 19:2164-2175, all of which are incorporated by reference herein). Plant miRNAs generally have near-perfect complementarity to their target sequences (see, for example, Llave et al. (2002) Science, 297:2053-2056, Rhoades et al. (2002) Cell, 110:513-520, Jones-Rhoades and Bartel (2004) Mol. Cell, 14:787-799, all of which are incorporated by reference herein). Thus, the mature miRNAs can be engineered to serve as sequences useful for gene suppression of a target sequence, by replacing nucleotides of the mature miRNA sequence with nucleotides of the sequence that is targeted for suppression; see, for example, methods disclosed by Parizotto et al. (2004) Genes Dev., 18:2237-2242 and especially U.S. Patent Application Publications US2004/0053411A1, US2004/0268441A1, US2005/0144669, and US2005/0037988 all of which are incorporated by reference herein. When engineering a novel miRNA to target a specific sequence, one strategy is to select within the target sequence a region with sequence that is as similar as possible to the native miRNA sequence. Alternatively, the native miRNA sequence can be replaced with a region of the target sequence, preferably a region that meets structural and thermodynamic criteria believed to be important for miRNA function (see, for example, U.S. Patent Application Publication US2005/0037988). Sequences are preferably engineered such that the number and placement of mismatches in the stem structure of the fold-back region or pre-miRNA is preserved. Thus, an engineered miRNA or engineered miRNA precursor can be derived from any of the mature miRNA sequences, or their corresponding miRNA precursors (including the fold-back portions of the corresponding MIR genes) disclosed herein. The engineered miRNA precursor can be cloned and expressed (transiently or stably) in a plant cell or tissue or intact plant.

The construction and description of recombinant DNA constructs to modulate small non-coding RNA activities are disclosed in US Patent Application Publication US 2009/0070898 A1, US2011/0296555 A1, US2011/0035839 A1, all of which are incorporated herein by reference in their entirety. In particular, with respect to US2011/0035839 A1, see e.g., sections under the headings "Gene Suppression Elements" in paragraphs 122 to 135, and "Engineered Heterologous miRNA for Controlling Gene Expression in paragraphs 188 to 190.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant cell" means a plant cell that is transformed with stably-integrated, recombinant DNA, for example, by Agrobacterium-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein a "control plant" means a plant that does not contain the recombinant DNA of the present disclosure that imparts an enhanced trait or altered phenotype. A control plant is used to identify and select a transgenic plant that has an enhanced trait or altered phenotype. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of drought tolerance, increased water use efficiency, cold tolerance, increased nitrogen use efficiency and increased yield as shown in Tables 7 and 9, and altered phenotypes as shown in Tables 4-6. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in a modified trait. Therefore, the trait modification observed entails a change of the normal distribution and magnitude of the trait in the plants as compared to a control plant.

The present disclosure relates to a plant with improved economically important characteristics, more specifically increased yield. More specifically the present disclosure relates to a plant comprising a polynucleotide of this disclosure, wherein the plant has increased yield as compared to a control plant. Many plants of this disclosure exhibited increased yield as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), seed production and more. Root development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear and number of kernels per row, kernel number or weight per ear, weight per kernel, ear number, ear weight, fresh or dry ear biomass (weight).

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having increased yield; performance of the method gives plants increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, aleurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by producing a plant comprising a poly-nucleic acid sequence of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA construct, transgenic plants can be prepared by crossing a first plant having a stably integrated recombinant DNA construct with a second plant lacking the DNA. For example, recombinant DNA can be introduced into a first plant line that is amenable to transformation to produce a transgenic plant which can be crossed with a second plant line to introgress the recombinant DNA into the second plant line.

Selected transgenic plants transformed with a recombinant DNA construct and having the polynucleotide of this disclosure provides the enhanced trait of increased yield compared to a control plant. Use of genetic markers associated with the recombinant DNA can facilitate production of transgenic progeny that is homozygous for the desired recombinant DNA. Progeny plants carrying DNA for both parental traits can be back-crossed into a parent line multiple times, for example usually 6 to 8 generations, to produce a progeny plant with substantially the same genotype as the one reoccurring original transgenic parental line but having the recombinant DNA of the other transgenic parental line.

The term "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, a oligonucleotide, or any fragment thereof. In many instances, a polynucleotide encodes a polypeptide (or protein) or a domain or a fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components, with which it is typically associated, for example, by any of the various protein purification methods.

As used herein, a "functional fragment" refers to a portion of a polypeptide provided herein which retains full or partial molecular, physiological or biochemical function of the full length polypeptide. A functional fragment often contains the domain(s), such as Pfam domains (see below), identified in the polypeptide provided in the sequence listing.

A "recombinant DNA construct" as used in the present disclosure comprises at least one expression cassette having a promoter operable in plant cells and a polynucleotide of the present disclosure. DNA constructs can be used as a means of delivering recombinant DNA constructs to a plant cell in order to effect stable integration of the recombinant molecule into the plant cell genome. In one embodiment, the polynucleotide can encode a protein or variant of a protein or fragment of a protein that is functionally defined to maintain activity in transgenic host cells including plant cells, plant parts, explants and whole plants. In another embodiment, the polynucleotide can encode a non-coding RNA that interferes with the functioning of endogenous classes of small RNAs that regulate expression, including but not limited to taRNAs, siRNAs and miRNAs. Recombinant DNA constructs are assembled using methods known to persons of ordinary skill in the art and typically comprise a promoter operably linked to DNA, the expression of which provides the enhanced agronomic trait.

Other construct components can include additional regulatory elements, such as 5' leaders and introns for enhancing transcription, 3' untranslated regions (such as polyadenylation signals and sites), and DNA for transit or targeting or signal peptides.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from common ancestral genes by speciation and encode proteins retain the same function, but do not include paralogs, i.e., genes that are related by duplication but have evolved to encode proteins with different functions. Homologous genes include naturally occurring alleles and artificially-created variants.

Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about 80%, at least about 85%, at least about 90%, at least about 92%, at least about 94%, at least about 95%, at least about 96%, at least about 97%, at least about 98%, at least about 99%, or even at least about 99.5% identity over the full length of a protein or its corresponding nucleotide sequence identified as being associated with imparting an enhanced trait or altered phenotype when expressed in plant cells. In one aspect of the disclosure homolog proteins have at least about 80%, at least about 85%, at least about 90%, at least about 92%, at least about 94%, at least about 95%, at least about 96%, at least about 97%, at least about 98%, at least about 99%, or at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions (UTRs) and their complements. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

Sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) Transgenic Res. 6(2):157-166, globulin 1 as disclosed by Belanger et al (1991) Genetics 129:863-872, glutelin 1 as disclosed by Russell (1997) supra, and peroxiredoxin antioxidant (Peri) as disclosed by Stacy et al. (1996) Plant Mol Biol. 31 (6): 1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule. As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For description of the transit peptide region of an *Arabidopsis* EPSPS gene in the present disclosure, see Klee, H. J. Et al (MGG (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or an herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvyl-shikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,378,824; 5,605,011)), bialaphos or phosphinothricin or derivatives (e. g., phosphinothricin acetyltransferase (bar) tolerance to phosphinothricin or glufosinate (U.S. Pat. Nos. 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a nontranslated RNA, in the sense or antisense direction, a miRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/0192813 A1; and the pea (*Pisum sativum*) ribulose biphosphate carboxylase gene (rbs 3'), and 3' elements from the genes within the host plant.

As used herein "operably linked" means the association of two or more DNA fragments in a recombinant DNA construct so that the function of one, for example, protein-encoding DNA, is controlled by the other, for example, a promoter.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) Plant J. 4:833-840 and in Misawa et al, (1994) Plant J. 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in US Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506,599; 5,986,175 and US Patent Application Publication 2003/0150017 A1.

Plant Cell Transformation Methods

Numerous methods for transforming chromosomes in a plant cell with recombinant DNA are known in the art and are used in methods of producing a transgenic plant cell and plant. Two effective methods for such transformation are Agrobacterium-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). Agrobacterium-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 8,044,260 (cotton); U.S. Pat. No. 6,384,301 (soybean), U.S. Pat. No. 7,026,528 (wheat) and U.S. Pat. No. 6,329,571 (rice), US Patent Application Publication 2004/0087030 A1 (cotton), and US Patent Application Publication 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA construct, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA construct into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708; 6,118,047 and 8,030,544. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of sequences of protein-encoding genes as recombinant DNA for production of transgenic plants with enhanced traits. The elements of Table 1 are described by reference to:

"NUC SEQ ID NO." which identifies a DNA sequence.
"PEP SEQ ID NO." which identifies an amino acid sequence.
"Gene ID" which refers to an arbitrary identifier.
"Gene Name and Description" which is a common name and functional description of the gene.

TABLE 1

Sequences for Protein-Coding Genes

| NUC SEQ ID NO. | PEP SEQ ID NO. | Gene ID | Gene Name and Description |
|---|---|---|---|
| 1 | 28 | TRDX4-01 | Arabidopsis mitochondrial import receptor subunit TOM5 homolog (TOM5) |
| 2 | 29 | TRDX4-02 | Arabidopsis K + independent Asparaginase |
| 3 | 30 | TRDX4-03 | Arabidopsis plasma membrane (PM)-localized cyclic nucleotide gated channels (CNGCs) |
| 4 | 31 | TRDX4-04 | Arabidopsis receptor like kinase |
| 5 | 32 | TRDX4-05 | Rice gibberellin receptor gene GID1 |
| 6 | 33 | TRDX4-06 | Corn plastidial phosphoenolpyruvate (PEP) phosphate translocator (PPT) |
| 7 | 34 | TRDX4-07 | Arabidopsis sulfolipid biosynthesis protein SQD1 |
| 8 | 35 | TRDX4-08 | Arabidopsis cytochrome P450 family protein |
| 9 | 36 | TRDX4-09 | *Pseudomonas syringae* phosphoglycerate kinase |
| 10 | 37 | TRDX4-10 | Corn phospholipase A (PLA1) |

TABLE 1-continued

Sequences for Protein-Coding Genes

| NUC SEQ ID NO. | PEP SEQ ID NO. | Gene ID | Gene Name and Description |
|---|---|---|---|
| 11 | 38 | TRDX4-11 | Arabidopsis plastidal glycolate/glycerate translocator 1 (PLGG1) |
| 12 | 39 | TRDX4-12 | Corn coiled coil domain protein |
| 13 | 40 | TRDX4-13 | Corn iron-phytosiderophore transporter protein yellow stripe 1 (YS1) |
| 14 | 41 | TRDX4-14 | Arabidopsis ACT domain-containing protein 3 (ACR3) |
| 15 | 42 | TRDX4-15 | *E coli* arginine-insensitive acetylglutamate kinase (NAGK) |
| 16 | 43 | TRDX4-16 | Soybean NOS1 (mitochondrial constitutive NOS) |
| 17 | 44 | TRDX4-17 | Corn thylakoid lumen protein CYP38 |
| 18 | 45 | TRDX4-18 | Arabidopsis glutaredoxin family protein |
| 19 | 46 | TRDX4-19 | *E coli* aminobutyrate aminotransferase |
| 20 | 47 | TRDX4-20 | *Synechocystis* sp. gene of unknown function |
| 21 | 48 | TRDX4-21 | Corn putative forever young oxidoreductase |
| 22 | 49 | TRDX4-22 | Corn MSH2 gene |
| 23 | 50 | TRDX4-23 | Arabidopsis mitogen-activated protein kinase kinase kinase 19 (MAPKKK19) |
| 24 | 51 | TRDX4-24 | Arabidopsis carbamoyl phosphate synthase EC 6.3.3.5 large subunit |
| 25 | 52 | TRDX4-25 | Soybean gene improving Nitrogen Utilization Efficiency (NUE) |
| 26 | 53 | TRDX4-26 | Arabidopsis casparian strip membrane protein 1 (CASP1) |
| 27 | 54 | TRDX4-27 | *E coli* codon redesigned asparagine synthetase A (AsnA) gene |

Table 2 provides a list of sequences for suppression of target protein-coding genes, as recombinant DNA for production of transgenic plants with enhanced traits. The elements of Table 2 are described by reference to:

"Target NUC SEQ ID NO." which identifies a nucleotide coding sequence of the suppression target gene.

"Target PEP SEQ ID NO." which identifies an amino acid sequence of the suppression target gene.

"Target Gene ID" which is an arbitrary identifier of the suppression target gene.

"Engineered miRNA precursor SEQ ID NO." which identifies a nucleotide sequence of the miRNA construct.

"miRNA recognition site SEQ ID NO." which identifies a nucleotide sequence of the miRNA recognition site.

"Target Gene Name and Description" which is a common name and functional description of the suppression target gene.

TABLE 2

Sequences for Gene Suppression

| Target NUC SEQ ID NO. | Target PEP SEQ ID NO. | Target Gene ID | Engineered miRNA precursor SEQ ID NO. | miRNA recognition site SEQ ID NO. | Target Gene Name and Description |
|---|---|---|---|---|---|
| 55 | 61 | TRDX4-1T | 67 | 73 | corn homolog of NOX1 gene, Plastidial phosphoenol-pyruvate (PEP) phosphate translocator (PPT) |
| 56 | 62 | TRDX4-3T | 68 | 74 | soybean SOUL gene |
| 57 | 63 | TRDX4-4T | 69 | 75 | soybean Elongated Hypocotyl 5 (Hy5) |
| 58 | 64 | TRDX4-5T | 70 | 76 | corn Proliferating cell nuclear antigen 2 (PCNA2) |
| 59 | 65 | TRDX4-6T | 71 | 77 | corn putative dolichyl-di-phosphooligosac-charide protein |
| 60 | 66 | TRDX4-7T | 72 | 78 | corn Peroxisomal_fatty_acid_beta-oxidation |

Selection Methods for Transgenic Plants with Enhanced Traits

Within a population of transgenic plants each regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Transgenic plants having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct screening for the trait in a greenhouse or field trial or by screening for a surrogate trait. Such analyses can be directed to detecting changes in the chemical composition, biomass, physiological property, or morphology of the plant. Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, filleting, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield are identified by screening using progenies of the transgenic plants over multiple locations for several years with plants grown under optimal production management practices and maximum weed and pest control or standard agronomic practices (SAP). Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, quinoa and sugar cane plants.

Example 1. Corn Transformation

This example illustrates transformation methods in producing a transgenic corn plant cell, seed, and plant having altered phenotypes as shown in Tables 4-6, or an enhanced trait, for example, increased water use efficiency, increased nitrogen use efficiency, and increased yield as shown in Tables 7 and 9.

For *Agrobacterium*-mediated transformation of corn embryo cells corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown Agrobacterium cells, and incubated at room temperature with Agrobacterium for 5-20 minutes. Inoculated immature embryos were then co-cultured with Agrobacterium for 1 to 3 days at 23° C. in the dark. Co-cultured embryos were transferred to selection media and cultured for approximately two weeks to allow embryogenic callus to develop Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1 or with recombinant DNA from Table 2 that is transcribed into a non-coding miRNA. Progeny transgenic plants and seeds of the transformed plants were screened for the presence and single copy of the inserted gene, and for increased water use efficiency, increased yield, increased nitrogen use efficiency, and altered phenotypes as shown in Tables 4-6. From each group of multiple events of transgenic plants with a specific recombinant DNA from Table 1 or Table 2, the event(s) that showed increased yield, increased water use efficiency, increased nitrogen use efficiency, and altered phenotypes was (were) identified.

Example 2. Soybean Transformation

This example illustrates plant transformation in producing a transgenic soybean plant cell, seed, and plant having altered phenotypes, or an enhanced trait, for example, increased water use efficiency or drought tolerance and increased yield as shown in Tables 7 and 9.

For Agrobacterium mediated transformation, soybean seeds were imbibed overnight and the meristem explants excised. Soybean explants were mixed with induced Agrobacterium cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA from the genes identified in Table 1 or recombinant DNA transcribed into a miRNA identified in Table 2. Progeny transgenic plants and seed of the transformed plant cells were screened for the presence and single copy of the inserted gene, and for increased water use efficiency and increased yield as shown in Tables 7 and 9.

Example 3. Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent publication No. US20110135161 (filed on Nov. 10, 2010), which is incorporated by reference herein in its entirety.

Screening and Identification of Transgenic Corn Plants for Altered Phenotypes.

Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific conditions as shown in Table 3.

TABLE 3

Description of the 3 AGH screens for corn plants

| Screen | Description | Germination phase (5 days) | Screen specific phase (22 days) |
| --- | --- | --- | --- |
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

Water deficit is defined as a specific Volumetric Water Content (VWC) that is lower than the VWC of non-stress plant. For example, a non-stressed plant might be maintained at 55% VWC and the VWC for a water-deficit assay might be defined around 30% VWC as shown in Table 3. Data were collected using visible light and hyperspectral imaging as well as direct measurement of pot weight and amount of water and nutrient applied to individual plants on a daily basis.

Nitrogen deficit is defined in part as a specific mM concentration of nitrogen that is lower than the nitrogen concentration of non-stress plants. For example, a non-stress plant might be maintained at 8 mM nitrogen while the nitrogen concentration applied in a nitrogen-deficit assay might be maintained at a concentration of 2 mM.

Up to ten parameters were measured for each screen. The visible light color imaging based measurements are: biomass, canopy area and plant height. Biomass (Bmass) is defined as estimated shoot fresh weight (g) of the plant obtained from images acquired from multiple angles of view. Canopy Area (Cnop) is defined as area of leaf as seen in top-down image (mm 2) Plant Height (PlntH) refers to the distance from the top of the pot to the highest point of the plant derived from side image (mm) Anthocyanin score and area, chlorophyll score and concentration, and water content score are hyperspectral imaging based parameters. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Chlorophyll Score (ClrpS) and Chlorophyll Concentration (ClrpC) are both measurements of chlorophyll in the leaf canopy obtained from a top-down hyperspectral image, where Chlorophyll Score measures in relative units and is done for soybean plants, and Chlorophyll Concentration measures in ppm units and is done for corn plants. Water Content Score (WtrCt) is a measurement of water in the leaf canopy obtained from a top-down hyperspectral image. Water Use Efficiency (WUE) is derived from the grams of plant biomass per liter of water added. Water Applied (WtrAp) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 4-6 are summaries of transgenic corn plants comprising the disclosed recombinant DNA constructs with altered phenotypes under non stress, nitrogen deficit, and water deficit conditions, respectively.

The test results are represented by three numbers: the first number before letter "p" denotes number of events with an increase in the tested parameter at $p \leq 0.1$; the second number before letter "n" denotes number of events with an decrease in the tested parameter at $p \leq 0.1$; the third number before letter "t" denotes total number of transgenic events tested for a given parameter in a specific screen. The increase or decrease is measured in comparison to non-transgenic control plants. A "-" means that it has not been tested. For example, 2p1n5t indicates that 5 transgenic plant events were screened, of which 2 events showed increase and 1 showed decrease of the measured parameter. Note that two constructs of gene TRDX4-19 were tested, and the results are listed as TRDX4-19 and TRDX4-19x.

TABLE 4

Summary of transgenic corn plants with altered phenotypes in AGH non-stres sscreens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-01 | 0p0n5t | 1p0n5t | 0p2n5t | 0p1n5t | — | 0p3n5t | 0p0n5t | 0p1n5t | 0p3n5t | — |
| TRDX4-02 | 0p1n5t | 0p1n5t | 0p2n5t | 0p2n5t | — | 0p3n5t | 0p2n5t | 0p2n5t | 0p3n5t | — |
| TRDX4-03 | — | 0p2n5t | 0p1n5t | 1p0n5t | — | 0p2n5t | 0p1n5t | 0p2n5t | 0p1n5t | — |
| TRDX4-04 | 1p0n5t | 0p0n5t | 0p2n5t | 0p0n5t | — | 0p1n5t | 0p3n5t | 0p1n5t | 0p1n5t | — |
| TRDX4-05 | 1p0n5t | 0p0n5t | 0p0n5t | 0p0n5t | — | 0p0n5t | 0p1n5t | 0p0n5t | 0p1n5t | — |
| TRDX4-07 | — | 0p0n5t | 1p0n5t | — | 1p0n5t | 1p0n5t | 0p1n5t | 0p0n5t | 3p0n5t | 1p0n5t |
| TRDX4-09 | 0p0n5t | 0p0n5t | 0p0n5t | 0p0n5t | — | 0p0n5t | 1p0n5t | 0p2n5t | 1p0n5t | — |
| TRDX4-11 | 0p1n5t | 0p0n5t | 0p1n5t | 0p0n5t | — | 0p0n5t | 0p1n5t | 0p1n5t | 1p1n5t | — |
| TRDX4-12 | 0p2n5t | 0p2n5t | 0p0n5t | 1p0n5t | — | 0p0n5t | 0p0n5t | 0p0n5t | 2p0n5t | — |
| TRDX4-13 | 1p0n5t | 0p0n5t | 0p0n5t | 0p1n5t | — | 0p1n5t | 0p1n5t | 0p0n5t | 0p0n5t | — |
| TRDX4-14 | 0p0n5t | 1p0n5t | 0p2n5t | 1p0n5t | — | 0p2n5t | 0p4n5t | 0p2n5t | 0p2n5t | — |
| TRDX4-16 | 0p0n5t | 0p0n5t | 0p0n5t | 0p0n5t | — | 0p1n5t | 0p1n5t | 0p0n5t | 0p0n5t | — |
| TRDX4-17 | 0p1n5t | 0p0n5t | 1p0n5t | 1p0n5t | — | 2p0n5t | 0p0n5t | 0p0n5t | 4p0n5t | — |
| TRDX4-18 | 0p2n5t | 0p0n5t | 2p1n5t | 0p0n5t | — | 1p0n5t | 0p1n5t | 1p0n5t | 3p1n5t | — |
| TRDX4-19 | 0p1n4t | 0p0n4t | 0p1n4t | 0p0n4t | — | 0p1n4t | 0p1n4t | 0p1n4t | 0p1n4t | — |
| TRDX4-19x | 1p0n5t | 1p0n5t | 0p0n5t | 0p0n5t | — | 0p3n5t | 0p1n5t | 0p0n5t | 0p1n5t | — |
| TRDX4-1T | 0p0n5t | 0p0n5t | 0p1n5t | 3p0n5t | — | 0p1n5t | 0p1n5t | 0p0n5t | 0p1n5t | — |
| TRDX4-20 | 0p0n3t | 0p1n3t | 0p1n3t | 0p1n3t | — | 0p1n3t | 0p1n3t | 0p1n3t | 0p1n3t | — |
| TRDX4-21 | 1p1n5t | 0p0n5t | 0p0n5t | 0p0n5t | — | 1p0n5t | 0p0n5t | 0p0n5t | 1p0n5t | — |
| TRDX4-22 | 0p0n3t | 1p0n3t | 0p0n3t | 0p0n3t | — | 0p1n3t | 0p0n3t | 0p0n3t | 0p1n3t | — |
| TRDX4-23 | 0p0n5t | 1p0n5t | 0p0n5t | 1p0n5t | — | 0p1n5t | 0p0n5t | 0p0n5t | 0p1n5t | — |
| TRDX4-25 | 1p0n5t | 0p0n5t | 0p0n5t | 2p0n5t | — | 0p1n5t | 0p0n5t | 0p0n5t | 0p0n5t | — |
| TRDX4-26 | 0p0n5t | 0p0n5t | 0p2n5t | 0p1n5t | — | 0p2n5t | 0p1n5t | 0p3n5t | 0p0n5t | — |
| TRDX4-27 | 0p0n7t | 0p0n7t | 0p1n7t | 0p0n7t | — | 0p1n7t | 0p1n7t | 0p0n7t | 0p0n7t | — |
| TRDX4-5T | 0p0n3t | 0p0n3t | 0p1n3t | 0p0n3t | — | 0p1n3t | 0p0n3t | 0p1n3t | 0p1n3t | — |
| TRDX4-6T | — | 0p1n5t | 0p4n5t | 0p0n5t | — | 0p3n5t | 0p1n5t | 0p4n5t | 0p2n5t | — |
| TRDX4-7T | 1p0n2t | 0p0n2t | 0p0n2t | 0p0n2t | — | 0p0n2t | 0p1n2t | 0p0n2t | 0p0n2t | — |

TABLE 5

Summary of transgenic corn plants with altered phenotypes in AGH nitrogen-deficit screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-01 | 3p0n5t | 0p1n5t | 0p1n5t | 0p0n5t | — | 0p3n5t | 0p2n5t | 0p2n5t | 1p2n5t | — |
| TRDX4-02 | 0p1n5t | 0p1n5t | 5p0n5t | 3p0n5t | — | 4p0n5t | 3p1n5t | 5p0n5t | 5p0n5t | — |
| TRDX4-03 | — | 0p0n5t | 0p3n5t | 0p0n5t | — | 0p4n5t | 0p2n5t | 0p2n5t | 0p3n5t | — |
| TRDX4-04 | 0p0n5t | 0p0n5t | 0p0n5t | 1p0n5t | — | 0p0n5t | 0p2n5t | 0p0n5t | 1p0n5t | — |
| TRDX4-05 | 5p0n5t | 0p1n5t | 0p2n5t | 0p0n5t | — | 0p1n5t | 0p0n5t | 0p3n5t | 0p4n5t | — |
| TRDX4-07 | — | 0p0n5t | 1p0n5t | — | 0p1n5t | 0p0n5t | 0p1n5t | 1p0n5t | 1p0n5t | 0p0n5t |
| TRDX4-09 | 0p0n5t | 0p0n5t | 0p0n5t | 0p0n5t | — | 0p0n5t | 0p0n5t | 0p0n5t | 0p1n5t | — |
| TRDX4-11 | 0p0n5t | 0p0n5t | 0p2n5t | 0p1n5t | — | 0p0n5t | 0p0n5t | 0p0n5t | 0p3n5t | — |
| TRDX4-12 | 0p4n5t | 0p0n5t | 1p0n5t | 1p0n5t | — | 2p0n5t | 0p0n5t | 1p0n5t | 0p0n5t | — |
| TRDX4-13 | 0p2n5t | 0p0n5t | 4p0n5t | 0p1n5t | — | 1p0n5t | 3p0n5t | 3p0n5t | 3p0n5t | — |
| TRDX4-14 | 3p0n5t | 0p0n5t | 0p2n5t | 0p0n5t | — | 0p1n5t | 0p4n5t | 0p1n5t | 0p3n5t | — |
| TRDX4-16 | 1p0n5t | 0p0n5t | 0p2n5t | 0p0n5t | — | 0p1n5t | 1p2n5t | 0p2n5t | 0p1n5t | — |
| TRDX4-17 | 0p2n5t | 1p0n5t | 0p0n5t | 1p1n5t | — | 2p0n5t | 0p1n5t | 0p0n5t | 0p4n5t | — |
| TRDX4-18 | 0p3n5t | 0p1n5t | 2p0n5t | 0p0n5t | — | 1p0n5t | 0p0n5t | 3p0n5t | 0p1n5t | — |
| TRDX4-19 | 0p1n3t | 0p0n3t | 1p0n3t | 0p0n3t | — | 2p0n3t | 1p0n3t | 0p0n3t | 2p0n3t | — |
| TRDX4-19x | 0p0n5t | 0p2n5t | 0p0n5t | 0p0n5t | — | 0p1n5t | 0p0n5t | 0p1n5t | 0p1n5t | — |
| TRDX4-1T | 1p0n5t | 0p1n5t | 1p0n5t | 0p0n5t | — | 0p1n5t | 0p2n5t | 1p1n5t | 1p0n5t | — |

TABLE 5-continued

Summary of transgenic corn plants with altered phenotypes in AGH nitrogen-deficit screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-20 | 0p2n3t | 0p2n3t | 2p0n3t | 0p0n3t | — | 1p0n3t | 1p0n3t | 2p0n3t | 2p0n3t | — |
| TRDX4-21 | 0p2n5t | 0p0n5t | 1p1n5t | 2p0n5t | — | 1p1n5t | 0p1n5t | 2p0n5t | 0p3n5t | — |
| TRDX4-22 | 0p2n3t | 0p0n3t | 2p0n3t | 0p0n3t | — | 1p0n3t | 2p0n3t | 2p0n3t | 3p0n3t | — |
| TRDX4-23 | 0p0n5t | 0p0n5t | 1p0n5t | 0p0n5t | — | 1p0n5t | 1p0n5t | 1p0n5t | 1p0n5t | — |
| TRDX4-25 | 0p0n5t | 0p0n5t | 0p0n5t | 1p0n5t | — | 0p1n5t | 0p2n5t | 1p0n5t | 0p2n5t | — |
| TRDX4-26 | 0p0n5t | 0p2n5t | 0p0n5t | 4p0n5t | — | 0p1n5t | 0p5n5t | 0p0n5t | 0p5n5t | — |
| TRDX4-27 | 1p1n7t | 0p1n7t | 0p0n7t | 1p0n7t | — | 0p1n7t | 0p1n7t | 0p0n7t | 1p1n7t | — |
| TRDX4-5T | 0p0n3t | 0p0n3t | 0p1n3t | 0p0n3t | — | 0p2n3t | 0p1n3t | 0p2n3t | 0p3n3t | — |
| TRDX4-6T | — | 0p2n5t | 5p0n5t | 5p0n5t | — | 3p0n5t | 4p0n5t | 5p0n5t | 5p0n5t | — |
| TRDX4-7T | 0p1n3t | 0p1n3t | 3p0n3t | 0p0n3t | — | 3p0n3t | 0p0n3t | 3p0n3t | 2p0n3t | — |

TABLE 6

Summary of transgenic corn plants with altered phenotypes in AGH water-deficit screens

| Gene_ID | AntA | AntS | Bmass | ClrpC | ClrpS | Cnop | PlntH | WUE | WtrAp | WtrCt |
|---|---|---|---|---|---|---|---|---|---|---|
| TRDX4-01 | 0p0n5t | 1p1n5t | 1p0n5t | 1p0n5t | — | 1p0n5t | 1p1n5t | 0p0n5t | 1p0n5t | — |
| TRDX4-02 | 0p0n5t | 3p0n5t | 2p0n5t | 0p0n5t | — | 0p0n5t | 1p1n5t | 1p1n5t | 0p3n5t | — |
| TRDX4-03 | — | 0p1n5t | 0p0n5t | 1p0n5t | — | 1p0n5t | 0p0n5t | 0p1n5t | 1p0n5t | — |
| TRDX4-04 | 0p2n5t | 0p0n5t | 1p0n5t | 0p0n5t | — | 1p0n5t | 0p2n5t | 1p0n5t | 0p0n5t | — |
| TRDX4-05 | 1p0n5t | 0p0n5t | 0p1n5t | 0p0n5t | — | 0p1n5t | 1p0n5t | 0p1n5t | 1p2n5t | — |
| TRDX4-07 | — | 4p0n5t | 0p1n5t | — | 3p1n5t | 0p2n5t | 0p2n5t | 0p1n5t | 0p4n5t | 4p1n5t |
| TRDX4-09 | 1p0n5t | 0p0n5t | 0p0n5t | 0p1n5t | — | 0p1n5t | 0p1n5t | 0p0n5t | 1p4n5t | — |
| TRDX4-11 | 2p0n5t | 0p0n5t | 0p0n5t | 2p0n5t | — | 0p0n5t | 0p0n5t | 0p0n5t | 1p2n5t | — |
| TRDX4-12 | 1p0n5t | 0p1n5t | 1p1n5t | 0p0n5t | — | 2p1n5t | 2p0n5t | 1p1n5t | 2p0n5t | — |
| TRDX4-13 | 4p0n5t | 0p1n5t | 0p5n5t | 0p0n5t | — | 0p5n5t | 0p5n5t | 0p3n5t | 0p5n5t | — |
| TRDX4-14 | 0p0n5t | 0p0n5t | 0p1n5t | 0p1n5t | — | 0p1n5t | 1p1n5t | 0p0n5t | 0p2n5t | — |
| TRDX4-16 | 0p0n5t | 0p0n5t | 0p0n5t | 0p0n5t | — | 0p0n5t | 1p0n5t | 0p0n5t | 0p0n5t | — |
| TRDX4-17 | 0p1n5t | 0p0n5t | 4p0n5t | 2p0n5t | — | 2p0n5t | 4p0n5t | 1p0n5t | 4p0n5t | — |
| TRDX4-18 | 0p2n5t | 0p0n5t | 3p0n5t | 1p0n5t | — | 1p0n5t | 1p2n5t | 2p1n5t | 4p0n5t | — |
| TRDX4-19 | 0p1n4t | 1p0n4t | 0p2n4t | 0p0n4t | — | 1p1n4t | 0p2n4t | 0p1n4t | 0p1n4t | — |
| TRDX4-19x | 0p1n5t | 0p0n5t | 0p0n5t | 0p0n5t | — | 0p0n5t | 0p0n5t | 0p0n5t | 1p2n5t | — |
| TRDX4-1T | 0p1n2t | 0p0n2t | 1p0n2t | 0p0n2t | — | 0p0n2t | 0p0n2t | 1p0n2t | 0p0n2t | — |
| TRDX4-20 | 0p1n3t | 0p0n3t | 0p0n3t | 0p0n3t | — | 0p0n3t | 0p1n3t | 0p0n3t | 0p0n3t | — |
| TRDX4-21 | 0p1n5t | 0p0n5t | 3p1n5t | 2p0n5t | — | 3p0n5t | 2p0n5t | 1p0n5t | 4p1n5t | — |
| TRDX4-22 | 0p0n1t | 0p0n1t | 1p0n1t | 0p1n1t | — | 0p0n1t | 0p0n1t | 0p0n1t | 1p0n1t | — |
| TRDX4-23 | 0p3n5t | 0p1n5t | 4p0n5t | 1p0n5t | — | 4p0n5t | 0p0n5t | 1p0n5t | 4p0n5t | — |
| TRDX4-25 | 1p0n5t | 1p0n5t | 1p0n5t | 1p0n5t | — | 1p0n5t | 0p0n5t | 0p0n5t | 0p1n5t | — |
| TRDX4-26 | 1p0n5t | 3p0n5t | 5p0n5t | 0p0n5t | — | 5p0n5t | 2p0n5t | 3p0n5t | 1p0n5t | — |
| TRDX4-27 | 4p0n7t | 0p0n7t | 0p2n7t | 1p1n7t | — | 1p0n7t | 0p2n7t | 0p1n7t | 0p1n7t | — |
| TRDX4-5T | 2p0n3t | 0p0n3t | 0p3n3t | 0p0n3t | — | 0p3n3t | 0p3n3t | 0p3n3t | 0p3n3t | — |
| TRDX4-6T | — | 0p1n5t | 0p0n5t | 0p0n5t | — | 0p0n5t | 1p0n5t | 0p0n5t | 0p0n5t | — |
| TRDX4-7T | 0p0n3t | 0p0n3t | 0p0n3t | 0p1n3t | — | 3p0n3t | 0p0n3t | 1p0n3t | 0p0n3t | — |

Example 4. Phenotypic Evaluation of Transgenic Plants for Increased Nitrogen Use Efficiency, Increased Water Use Efficiency and Increased Yield Corn field trials were conducted to identify genes that can improve nitrogen use efficiency (NUE) under nitrogen limiting conditions leading to increased yield performance as compared to non transgenic controls. For the Nitrogen field trial results shown in Tables 7 and 9, each field was planted under nitrogen limiting condition (60 lbs/acre) and corn ear weight or yield was compared to non transgenic control plants.

Corn field trials were conducted to identify genes that can improve water use efficiency (WUE) under water limiting conditions leading to increased yield performance as compared to non transgenic controls. The water use efficiency trials for results shown in Tables 7 and 9 were conducted under managed water limiting conditions, and the corn ear weight or yield was compared to non transgenic control plants.

Corn and soybean field trials were conducted to identify genes that can improve broad-acre yield (BAY) under standard agronomic practice. The broad-acre yield trials for results shown in Tables 7 and 9 were conducted under standard agronomic practice, and the corn or soybean yield was compared to non transgenic control plants.

Table 7 provides a list of genes for producing transgenic plants with increased nitrogen use efficiency (NUE), increased water use efficiency (WUE), and increased broad-acre yield (BAY) as compared to a control plant. Polynucleotide sequences in constructs with at least one event showing significant yield or ear weight increase across multiple locations at p≤0.2 are included. The genes were expressed with constitutive promoters unless noted otherwise under "Specific Expression Pattern". Promoter of specific expression pattern was chosen over constitutive promoter, based on the understanding of the gene function, or based on the observed lack of significant yield increase when the gene was expressed with constitutive promoter. The elements of Table 7 are described by reference to:

"Crop" which refers to the crop in trial, which is either corn or soybean;

"Condition" which refers to the type of field trial, which is BAY for broad acre yield trial under standard agronomic practice (SAP), WUE for water use efficiency trial, and NUE for nitrogen use efficiency trial;

"Specific Expression Pattern" which refers to the expected expression pattern or promoter type, instead of constitutive;

"Gene ID" which refers to the gene identifier as defined in Table 1;

"Yield results" which refers to the recombinant DNA in a construct with at least one event showing significant yield increase at p≤0.2 across locations. The first number refers to the number of events with significant yield or ear weight increase, whereas the second number refers to the total number of events tested for each recombinant DNA in the construct.

TABLE 7

Recombinant DNA with protein-coding genes for increased nitrogen use efficiency, increased water use efficiency and increased yield

| Crop | Condition | Specific Expression Pattern | Gene ID | Yield Results |
|---|---|---|---|---|
| corn | BAY | leaf preferred | TRDX4-01 | 2/15 |
| corn | BAY | seed preferred | TRDX4-02 | 1/13 |
| corn | BAY | | TRDX4-03 | 2/8 |
| corn | BAY | | TRDX4-04 | 1/23 |
| corn | BAY | | TRDX4-05 | 1/23 |
| corn | BAY | | TRDX4-06 | 1/7 |
| corn | WUE | | TRDX4-07 | 2/4 |
| corn | BAY | cold inducible | TRDX4-08 | 4/26 |
| corn | BAY | | TRDX4-09 | 1/25 |
| corn | NUE | | TRDX4-10 | 1/12 |
| corn | BAY | | TRDX4-11 | 1/20 |
| corn | BAY | | TRDX4-12 | 8/20 |
| corn | BAY | | TRDX4-13 | 2/32 |
| corn | BAY | | TRDX4-14 | 2/20 |
| soybean | BAY | | TRDX4-15 | 4/13 |
| corn | BAY | | TRDX4-16 | 1/20 |
| corn | BAY | leaf preferred | TRDX4-17 | 2/13 |
| corn | BAY | | TRDX4-18 | 2/19 |
| corn | WUE | leaf preferred | TRDX4-19 | 1/5 |
| corn | BAY | | TRDX4-19 | 2/22 |
| corn | BAY | leaf preferred | TRDX4-20 | 1/20 |
| corn | BAY | | TRDX4-21 | 4/19 |
| corn | NUE | | TRDX4-22 | 2/10 |
| corn | BAY | leaf preferred | TRDX4-23 | 1/19 |
| soybean | BAY | | TRDX4-24 | 3/15 |
| corn | BAY | | TRDX4-25 | 2/18 |
| corn | BAY | root preferred | TRDX4-26 | 3/21 |
| corn | BAY | | TRDX4-27 | 3/24 |

Table 8 provides a list of polynucleotide sequences of promoters with specific expression patterns. To convey the specific expression patterns, choices of promoters are not limited to those listed in Table 8.

TABLE 8

Promoter sequences and expression patterns

| Nucleotide SEQ ID NO. | Promoter Expression Pattern |
|---|---|
| 97 | Cold inducible |
| 98 | Seed preferred |
| 99 | Leaf preferred |
| 100 | Leaf preferred |

Table 9 provides a list of suppression target genes and miRNA construct elements provided as recombinant DNA for production of transgenic corn or soybean plants with increased nitrogen use efficiency, increased water use efficiency and increased yield. The elements of Table 9 are described by reference to:

"Crop" which refers to the crop in trial, which is either corn or soy;

"Condition" which refers to the type of field trial, which is BAY for broad acre yield trial under standard agronomic practice, WUE for water use efficiency trial, and NUE for nitrogen use efficiency trial;

"Target Gene ID" which refers to the suppression target gene identifier as defined in Table 2;

"Engineered miRNA precursor SEQ ID NO." which identifies a nucleotide sequence of the miRNA construct;

"Yield results" which refers to the recombinant DNA in a construct with at least one event showing significant yield increase at p≤0.2 across locations. The first number refers to the number of events with significant yield or ear weight increase, whereas the second number refers to the total number of events tested for each sequence in the construct.

TABLE 9 miRNA Recombinant DNA constructs suppressing targeted genes for increased nitrogen use efficiency, increased water use efficiency and increased yield

| Crop | Condition | Target Gene ID | Engineered miRNA precursor SEQ ID NO. | Yield Results |
|---|---|---|---|---|
| corn | BAY | TRDX4-1T | 67 | 1/13 |
| soybean | BAY | TRDX4-3T | 68 | 4/15 |
| soybean | BAY | TRDX4-4T | 69 | 3/14 |
| corn | BAY | TRDX4-5T | 70 | 2/20 |
| corn | NUE | TRDX4-6T | 71 | 1/6 |
| corn | WUE | TRDX4-6T | 71 | 1/6 |
| corn | BAY | TRDX4-6T | 71 | 2/20 |
| corn | WUE | TRDX4-7T | 72 | 1/5 |

Example 5. Homolog Identification

This example illustrates the identification of homologs of proteins encoded by the DNA identified in Table 1 which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp"

program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over 95% of the length of the polypeptide sequences provided in Table 1 are reported below in Tables 10 and 11.

Table 10 provides a list of homolog genes, of which the elements are described by reference to:

"PEP SEQ ID NO." which identifies an amino acid sequence.

"Homolog ID" which refers to an alphanumeric identifier, the numeric part of which is the NCBI Genbank GI number.

"Gene Name and Description" which is a common name and functional description of the gene.

Table 11 describes the correspondence between the protein-coding genes in Table 1, suppression target genes in Table 2, and their homologs, and the level of protein sequence alignment between the gene and its homolog. Note that homologs can be from Table 1, 2 or 10.

TABLE 11

Correspondence of Genes and Homologs

| Gene ID | Homolog ID | Percent Gene Coverage | Percent Homolog Coverage | Percent Identity |
|---|---|---|---|---|
| TRDX4-02 | gi_735918 | 100 | 100 | 99 |
| TRDX4-03 | gi_110742427 | 100 | 100 | 99 |
| TRDX4-05 | gi_215261267 | 100 | 97 | 100 |
| TRDX4-06 | TRDX4-1T | 100 | 100 | 99 |
| TRDX4-06 | gi_193211383 | 100 | 100 | 99 |
| TRDX4-08 | gi_3164136 | 100 | 100 | 99 |
| TRDX4-09 | gi_28867617 | 99 | 100 | 100 |
| TRDX4-09 | gi_71734219 | 99 | 100 | 96 |
| TRDX4-09 | gi_66048014 | 99 | 100 | 96 |
| TRDX4-10 | gi_242053823 | 100 | 100 | 95 |
| TRDX4-11 | gi_21593232 | 100 | 100 | 99 |

TABLE 10

Homolog genes information

| PEP SEQ ID NO. | Homolog ID | Gene Name and Description |
|---|---|---|
| 79 | gi_735918 | gi|735918|emb|CAA84367.1|asparaginase [Arabidopsis thaliana] |
| 80 | gi_110742427 | gi|110742427|dbj|BAE99132.1| cyclic nucleotide-gated cation channel [Arabidopsis thaliana] |
| 81 | gi_215261267 | gi|215261267|pdb|3EBL|A Chain A, Crystal Structure Of Rice Gid1 Complexed With Ga4 [Oryza sativa Japonica group] |
| 82 | gi_193211383 | gi|193211383|ref|NP_001105952.1| plastid phosphate/phosphoenolpyruvate translocator1 [Zea mays] |
| 83 | gi_3164136 | gi|3164136|dbj|BAA28535.1| cytochrome P450 monooxygenase [Arabidopsis thaliana] |
| 84 | gi_28867617 | gi|28867617|ref|NP_790236.1| phosphoglycerate kinase [Pseudomonas syringae pv. tomato str. DC3000] |
| 85 | gi_71734219 | gi|71734219|ref|YP_276916.1| phosphoglycerate kinase [Pseudomonas syringae pv. phaseolicola 1448A] |
| 86 | gi_66048014 | gi|66048014|ref|YP_237855.1| phosphoglycerate kinase [Pseudomonas syringae pv. syringae B728a] |
| 87 | gi_242053823 | gi|242053823|ref|XP_002456057.1| hypothetical protein SORBIDRAFT_03g029630 [Sorghum bicolor] |
| 88 | gi_21593232 | gi|21593232|gb|AAM65181.1| unknown [Arabidopsis thaliana] |
| 89 | gi_226510490 | gi|226510490|ref|NP_001148910.1|LOC100282530 [Zea mays] gi|195623174|gb|ACG33417.1| pre-mRNA-splicing factor ISY1 [Zea mays] |
| 90 | gi_242065688 | gi|242065688|ref|XP_002454133.1| hypothetical protein SORBIDRAFT_04g025200 [Sorghum bicolor] |
| 91 | gi_21593552 | gi|21593552|gb|AAM65519.1|unknown [Arabidopsis thaliana] |
| 92 | gi_21593833 | gi|21593833|gb|AAM65800.1| glutaredoxin-like protein [Arabidopsis thaliana] |
| 93 | gi_226506654 | gi|226506654|ref|NP_001146301.1|DNA mismatch repair protein MSH2 [Zea mays] |
| 94 | gi_242050756 | gi|242050756|ref|XP_002463122.1| hypothetical protein SORBIDRAFT_02g038230 [Sorghum bicolor] |
| 95 | gi_255639875 | gi|255639875|gb|ACU20230.1| unknown [Glycine max] |
| 96 | gi_195623972 | gi|195623972|gb|ACG33816.1| triose phosphate/phosphate translocator, non-green plastid, chloroplast precursor [Zea mays] |

TABLE 11-continued

Correspondence of Genes and Homologs

| Gene ID | Homolog ID | Percent Gene Coverage | Percent Homolog Coverage | Percent Identity |
|---|---|---|---|---|
| TRDX4-12 | gi_226510490 | 100 | 100 | 99 |
| TRDX4-12 | gi_242065688 | 100 | 100 | 98 |
| TRDX4-14 | gi_21593552 | 100 | 100 | 99 |
| TRDX4-18 | gi_21593833 | 99 | 100 | 100 |
| TRDX4-22 | gi_226506654 | 100 | 100 | 99 |
| TRDX4-22 | gi_242050756 | 100 | 100 | 95 |
| TRDX4-25 | gi_255639875 | 100 | 100 | 99 |
| TRDX4-1T | TRDX4-06 | 100 | 100 | 99 |
| TRDX4-1T | gi_195623972 | 100 | 100 | 99 |
| TRDX4-1T | gi_193211383 | 100 | 100 | 99 |

Example 6. Use of Suppression Methods to Suppress Expression of Target Genes

This example illustrates monocot and dicot plant transformation with recombinant DNA constructs that are useful for stable integration into plant chromosomes in the nuclei of plant cells to provide transgenic plants having enhanced traits by suppression of the expression of target genes.

Various recombinant DNA constructs for use in suppressing the expression of a target gene in transgenic plants are constructed based on the nucleotide sequence of the gene encoding the protein that has an amino acid sequence selected from the group consisting of SEQ ID NOs: 61-66, where the DNA constructs are designed to express (a) a miRNA that targets the gene for suppression, (b) an RNA that is a messenger RNA for a target protein and has a synthetic miRNA recognition site that results in down modulation of the target protein, (c) an RNA that forms a dsRNA and that is processed into siRNAs that effect down regulation of the target protein, (d) a ssRNA that forms a trans-acting siRNA which results in the production of siRNAs that effect down regulation of the target protein.

Each of the various types of recombinant DNA constructs is used in transformation of a corn cell using the vector and method of Examples 1 and 2 to produce multiple events of transgenic corn cell. Such events are regenerated into transgenic corn plants and are screened to confirm the presence of the recombinant DNA and its expression of RNA for suppression of the target protein. The population of transgenic plants from multiple transgenic events are also screened to identify the transgenic plants that exhibit altered phenotype or enhanced trait.

We claim:

1. A recombinant DNA construct comprising a heterologous cold-inducible promoter functional in a plant cell and operably linked to:
   a) a polynucleotide that comprises a nucleotide sequence with at least 95%, at least 96%, at least 97%, at least 98%, at least 99% identity, or 100% identity to SEQ ID NO:8; or
   b) a polynucleotide that encodes a polypeptide having an amino acid sequence with at least 95%, at least 96%, at least 97%, at least 98%, at least 99% identity, or 100% identity to SEQ ID NO: 35.

2. A plant comprising a recombinant DNA construct comprising a heterologous cold-inducible promoter functional in a plant cell and operably linked to:
   a) a polynucleotide that comprises a nucleotide sequence with at least 95%, at least 96%, at least 97%, at least 98%, at least 99% identity, or 100% identity to SEQ ID NO:8; or
   b) a polynucleotide that encodes a polypeptide having an amino acid sequence with at least 95%, at least 96%, at least 97%, at least 98%, at least 99% identity, or 100% identity to SEQ ID NO: 35.

3. The plant of claim 2, wherein said plant has an altered phenotype or an enhanced trait as compared to a control plant.

4. The plant of claim 2, wherein said plant is a progeny, a propagule, or a field crop.

5. The plant of claim 2, wherein said plant is a field crop selected from the group consisting of corn, soybean, cotton, canola, rice, barley, oat, wheat, turf grass, alfalfa, sugar beet, sunflower, quinoa and sugar cane.

6. The plant of claim 2, wherein said plant is a propagule selected from the group consisting of cell, pollen, ovule, flower, embryo, leaf, root, stem, shoot, meristem, grain and seed.

7. The plant of claim 3, wherein said enhanced trait is increased yield, increased nitrogen use efficiency, or increased water use efficiency as compared to a control plant.

8. The plant of claim 3, wherein said phenotype is increased water use efficiency.

9. A method for increasing yield, increasing nitrogen use efficiency, or increasing water use efficiency in a plant comprising producing a plant comprising a recombinant DNA construct comprising a heterologous cold-inducible promoter functional in a plant cell and operably linked to:
   a) a polynucleotide that comprises a nucleotide sequence at least 95%, at least 96%, at least 97%, at least 98%, at least 99% identity, or 100% identity to SEQ ID NO:8; or
   b) a polynucleotide that encodes a polypeptide having an amino acid sequence with at least 95%, at least 96%, at least 97%, at least 98%, at least 99% identity, or 100% identity to SEQ ID NO: 35.

10. The method of claim 9 wherein said plant is produced by transforming a plant cell or tissue with said recombinant DNA construct and regenerating a plant from said cell or tissue containing said recombinant DNA construct.

11. The method of claim 9 comprising producing said plant by crossing said plant through breeding with:
    a) itself;
    b) a second plant from the same plant line;
    c) a wild type plant; or
    d) a second plant from a different line of plants to produce a seed, growing said seed to produce a plurality of progeny plants; and selecting a progeny plant with increased yield, increased nitrogen use efficiency, or increased water use efficiency as compared to a control plant.

* * * * *

SEQUENCE LISTING

```
Sequence total quantity: 104
SEQ ID NO: 1            moltype = DNA  length = 165
FEATURE                 Location/Qualifiers
source                  1..165
                        mol_type = unassigned DNA
                        organism = Arabidopsis thaliana
SEQUENCE: 1
atggtgaaca acgttgtctc tatcgaaaag atgaaagcac tctggcactc cgaggttcat   60
gatgaacaaa aatgggcggt gaacatgaaa cttctgcgag cacttggtat gtttgcagga  120
ggagtcgtcc tcatgcgtag ctatggggat ctcatgggaa tttga                  165

SEQ ID NO: 2            moltype = DNA  length = 948
FEATURE                 Location/Qualifiers
source                  1..948
                        mol_type = unassigned DNA
                        organism = Arabidopsis thaliana
SEQUENCE: 2
atggtggggt gggcgattgc gctacacggc ggtgccggag acattccgat cgatctcccc   60
gacgagcgac gtatccctcg tgagagcgcc ctccgtcact gcctcgatct tggcatctcc  120
gccctcaaat ccggcaagcc tcccttggac gtcgccgaac ttgtcgttcg tgaacttgag  180
aaccaccccgg acttcaatgc gggtaaagga tctgtcttaa ctgcacaagg cactgttgaa  240
atggaagctt ccattatgga cggtaaaacc aaaagatgtg gagctgtctc cggcttgacc  300
actgttgtta atcccatttc tttagctcgc ctcgtcatgg agaaaactcc tcatatatat  360
cttgcattcg atgctgctga agcttttgca agagcacatg gtgttgagac ggtagattct  420
agccatttca taactcctga aaacattgca aggctaaagc aggccaaaga attcaatcga  480
gtccagttgg attacacagt ccctagtccg aaagtaccgg acaattgcgg tgacagccaa  540
ataggaacgg tcggatgtgt agctgtggac agtgctggaa atctagcttc ggctacatca  600
acgggcggtt atgtcaacaa aatggttggc agaattgggg atacgccagt cattggcgca  660
ggaacttacg ctaaccacct ttgtgccatc tcagccacag gtaaaggaga ggatatcatc  720
cgtggaaccg tggctagaga cgtggctgca ctcatggaat ataaaggctt gtctttgact  780
gaggcagcgg cttatgttgt tgaccaatct gttcccagag gaagctgtgg actcgttgct  840
gtctctgcca atggtgaagt cacaatgccg tttaacacta ccggaatgtt cagggcttgt  900
gctagcgaag atggttactc tgagatcgca atctggccaa acaattga              948

SEQ ID NO: 3            moltype = DNA  length = 2181
FEATURE                 Location/Qualifiers
source                  1..2181
                        mol_type = unassigned DNA
                        organism = Arabidopsis thaliana
SEQUENCE: 3
atgccctctc accccaactt catcttcagg tggattggac tgttttccga taagttccgt   60
cgacaaacga ctgggatcga tgaaaacagt aacctccaaa tcaacggtgg agattcgagc  120
agcagcggca gcgatgagac gccggtgcta agctccgtcg agtgttacgc ttgcacacaa  180
gtaggcgtcc cagctttcca ttcaactagc tgcgatcaag ctcacgcgcc ggagtggcgt  240
gcctccgccg gctcttctct agttccgatc caggaaggat ctgtccctaa cccagcccga  300
accagattcc gacgtctcaa aggtccgttt ggtgaagttc tcgatcctag gagcaagcgc  360
gtgcagagat ggaaccgcgc gttgcttta gctcgtggga tggctttagc ggtggatccg  420
```

```
ctcttcttct acgcgctttc catcggccga actaccggac cggcgtgtct ttacatggat   480
ggtgcgttcg ccgcggtggt cacggtgctc cgcacgtgtc tcgatgctgt tcatctttgg   540
cacgtgtggc ttcaattcag actggcctac gtctcgagag agtcgcttgt cgttggttgt   600
gggaagctcg tttgggatcc acgcgccatc gcgtctcact acgcacgctc tctcactggc   660
ttctggtttg atgttatcgt catcctccct gtccctcagg cagtgttttg gttagttgtg   720
ccgaaactga taagagaaga gaaggttaag ctgataatga cgattctgct gctaatattc   780
ttgttccagt tcctccccaa gatttatcac tgcatctgtt tgatgagaag gatgcagaag   840
gtcactggtt acatttttgg aactatttgg tggggttttg ctcttaatct catcgcatat   900
ttcatcgctt ctcatgttgc tggggatgt tggtatgttc tcgcaataca gcgtgttgtt   960
tcttgcataa gacaacaatg tatgagaacc gggaactgca atctgagtct ggcttgcaaa  1020
gaagaggtct gttaccaatt tgtgtcaccg acaagcacag ttggatatcc atgcttatct  1080
ggaaaccttg ccagtgtggt caataagcct atgtgcttag actctaacgg accattccga  1140
tatggtatct accgttgggc acttccagtc atctccagca actctcttgc ggttaagatc  1200
ctttacccca tcttctgggg cctaatgact ctcagcacat ttgcgaatga tcttgagccc  1260
acaagcaact ggctcgaggt tattttcagt atagttatgg ttctaagtgg cttgttactt  1320
ttcacgctgt tgataggaaa cattcaggtg ttttttgcatg cggtaatggc gaaaaaaagg  1380
aaaatgcaga tacggtgtag ggatatgaa tggtggatga aacgtaggca gttaccttcc   1440
cggttaagac agagggttag gcgatttgag cggcagagat ggaatgcctt gggtggtgaa   1500
gacgagctag aacttataca tgatttgcct ccgggtcttc gaagagatat caaacgatat   1560
ctttgctttg atctcattaa caaggtgcca ttgttcaggg gcatgacgga cttgatcctc   1620
gacaacattt gcgatcgggc taagcctcga gtcttctcta aagacgaaaa gatcatccgt   1680
gaaggagatc ctgtacagag aatgatattc atcatgcggt gacgagtcaa acgtatacag   1740
agcctaagca aaggcgtcct agccactagt acactagaac caggcggtta cttgggcgac   1800
gagctactct catggtgcct acgtcgcccg tttctggacc gtcttccccc ttcctcagca   1860
acatttgtct gcctagaaaa catcgaggca ttctccctcg gatccgaaga tcttaggtac   1920
attaccgatc atttccgtta taaattcgcg aacgagcggc ttaagcggac cgcaagatac   1980
tattcctcaa actggaggac gtgggcagcg gtaaatattc agatggcgtg cgcgccggcgt  2040
aggaaaagaa cccgtggtga aaacatcggc ggttcgatga gtcctgtgtc ggagaatagc   2100
attgaaggta acagtgaacg ccggttactt cagtatgcag ctatgttcat gtccattcga   2160
ccgcatgatc atctcgaata a                                              2181

SEQ ID NO: 4            moltype = DNA  length = 1404
FEATURE                 Location/Qualifiers
source                  1..1404
                        mol_type = unassigned DNA
                        organism = Arabidopsis thaliana
SEQUENCE: 4
atgattcttg atttgggttt tccttgtttt gttcctcctc gaaccagctc tcgtgaggac     60
aacaaagctt ggcttctggc tgaaacagag ccgaagctta ttgactcaga acaacattcg    120
ttgcagtctt cgtttaggtt tagtctttgc tcacagttgg agctggagaa gattaaaaag    180
gagaaacctt cgttgtctta tcggaatttt ccagtgtctg aaggatcaga gacggttctg    240
ctagtgaatc tggagaatga gacaggagaa ttgacaggtg agatgaattg gtcgagaggc    300
ctttcactgg agaagagtat ttctccggtg gccgattctt tgatccgatt cagttaccgc    360
gaactcctca ctgccacgcg caatttctca aaacgagggt tttgggaag aggagcttgt    420
agctatgttt taagggaag aatcgggatt tggcgtaaag ccgtggccat caaaagactt    480
gataaaaaag ataagaatc tccaaagtcg ttttgcagag agttgatgat tgcaagctct    540
cttaatagcc ccaacgttgt gcctctgcta ggtttctgta tcgatcccga tcaagggctt    600
ttcttggtgt acaagtatgt gtctggtggc agcctcgaac gcttttttaca tgataagaag    660
aaaaagaaga gtaggaagac ccccttgaat ctgccttggt ctacaaggta caaggttgcc    720
ttaggtattg cagatgccat agcctattta cataatggca ctgagcaatg cgttgtgcat    780
agagacatta aaccctcaaa tattcttctt tcctcaaaca aaattccaaa gttgtgtcat    840
tttgggttgg ctacttggac cgctcgcgcct tcggttcctt tcctctgtaa accgtgaaa    900
ggaacttttg gttatctggc tcctgagtat ttccaacacg gcaagatatc tgacaagacc    960
gatgtttacg catttgggt cgtgttgctt gagctaataa ctggtcggaa gccaattgaa   1020
gcaagaagac catctggtga agaaaatttg gtagtttggg caaaaccgtt gttgcataga   1080
gggatagaag ctacagagga gttgctagat ccaaggctga aatgtactag aaaaaactcg   1140
gcttcgatga gcgtatgat ccgagctgcg gcagcgtgtg tgatcaatga ggaatcacga   1200
agaccggga tgaaggagat acttttcaatc ctaaaaggcg gtgaagggat agaactaagg   1260
acgttatcaa gccggaagaa atcaaatctt ccgggtataa tggactgtta tccgcagttg   1320
caacggacaa aatctgagat gaagagtcat cttacgcttt cgatgctcgg agtaacggaa   1380
tttgaagctg atgatctttt gtag                                           1404

SEQ ID NO: 5            moltype = DNA  length = 1065
FEATURE                 Location/Qualifiers
source                  1..1065
                        mol_type = unassigned DNA
                        organism = Oryza sativa
SEQUENCE: 5
atggccggca gcgacgaggt caaccgcaac gagtgcaaga cggtggtgcc gctccacaca     60
tgggtgctca tctccaactt caagctgtcg tacaacattc tgcggcgggc ggacgggacg    120
ttcgagcggg acctcgggga gtacctggac aggagggtgc cggcgaacgc gcggccgctg    180
gaggggggtgt cgtcgttcga ccacatcatc gaccagtcgg tggggctgga ggtgcgcatc    240
taccgggcgg cggcggaggg tgacgcgga gaggggcgg cggcggtgac gcggcccatc    300
cttgagttcc tgacggcgcc gccagcgcg gagcgtttcc cgtgatcat attcttccac    360
ggcggcagct tcgtgcactc gtcggccagc tcgaccatct acgacagtct gtgccgccgg    420
ttcgtgaagc tgagcaaggg cgtcgtggtg tccgtcaact accggcgcgc gccggagcac    480
cgctacccgt gcgcgtacga cgacgggtgg accgcgctca gtgggtcat gtcgcagccg    540
ttcatgcgca gcgcggcgga cgcgcaggcc cgcgtgttcc tctccggcga cagctccggc    600
ggcaacatcg cccaccacgt cgccgtccgc gccgccgacg agggcgtcaa ggtctgcggc    660
```

```
aacatcctgc tcaacgccat gttcggcggc accgagcgca cggagtcgga gcggcggctc  720
gacggcaagt acttcgtgac gctccaggac agggactggt actggaaggc gtacctgccg  780
gaggacgccg accgggacca tccggcgtgc aacccgttcg gcccgaacgg ccggcggctc  840
gggggcctcc ccttcgccaa gagcctcatc atcgtgtcgg gcctggacct cacctgcgac  900
cggcagctcg cctacgccga cgccctccgg gaggacggcc accacgtcaa ggttgtccaa  960
tgcgagaacg ccacggtggg gttctacctg ttgcccaaca ccgtccacta ccacgaggtc  1020
atggaggaga tctccgactt cctcaacgct aacctctact actag                  1065

SEQ ID NO: 6           moltype = DNA   length = 1173
FEATURE                Location/Qualifiers
source                 1..1173
                       mol_type = unassigned DNA
                       organism = Zea mays
SEQUENCE: 6
atgcagagcg cggctgccat cgggctccta cggccatgtg ccgcgcggcc gctcgccgcc  60
tacactagcc cacgccgcgg cgccggcgcg tgcagcggcg gcacccagcc gatcatcacg  120
ccccgcggca tccgcctctc cgcccgcccc ggtctcgtgc cggcctcgcc gctggaggag  180
aaggagaacc ggagatgcag ggccagtatg cacgcggcgg cgtcggccgg agaggaagct  240
gggggagggc tcgccaagac gctgcagctg ggggcgcttt tcgggctctg gtacctcttc  300
aacatctact tcaacatcta caacaagcag gttctgaagg ttttgccata ccctataaac  360
atcacaacgt gcagtttgc tgttggaagt gccattgctt tgttcatgtg gatcactggt  420
atccataaaa ggccaaagat ttcgggtgcc cagcttttcg tatccttcc tctagctatt  480
gtccatacca tgggcaatct tttcacaaac atgagccttg gaaaggtggc agtgtcattt  540
acacatacta taaggccat ggaacctttc ttctcagttc tcctttcagc aattttcctt  600
ggggagttgc ctacgccatg ggttgtgttg tctcttcttc cgattgttgg tggtgtagct  660
ttggcatccc ttactgaggc ctcctttaac tgggctgaac tttggagtgc aatggcttca  720
aatgtaaacct tccagtcaag gaatgtgcta agcaagaaac ttatggtgaa gaaagaggaa  780
tctctcgaca acattaacct attctcgatc attacagtca tgtcattctt cctgttggcc  840
ccagtaacct tacttacaga aggtgttaaa gttagtccag cagtgttgca gtctgctggt  900
ttgaacttga aacaggtata cacaaggtca ttgattgctg cattctgctt catgcatac   960
caacaggtgt catacatgat cctcgccagg gtatcccag tcacacattc agtgggcaat  1020
tgcgtcaagc gtgtggtggt cattgtgacc tctgttctgt tcttcaggac ccctgtttct  1080
cccatcaact ctcttggtac cgggatcgct cttgctggag ttttcctata ctcgcaattg  1140
aagagactta agcccaagcc caagactgct tag                               1173

SEQ ID NO: 7           moltype = DNA   length = 1434
FEATURE                Location/Qualifiers
source                 1..1434
                       mol_type = unassigned DNA
                       organism = Arabidopsis thaliana
SEQUENCE: 7
atggcgcatc tactttcagc ttcatgccct tcagttatct cacttagcag cagcagcagc  60
aagaattcag ttaagccgtt tgtttcaggg cagaccttct tcaatgctca gcttcttca   120
agatcttctc tcaaaggact tctcttccaa gagaagaaac cgagaaaaag ctgcgttttc  180
agagcaactg ctgtacctat aacccaacaa gcaccacccg aaacatctac caataactca  240
tcctctaaac caaagcgtgt tatggtcatt ggtggagatg gttattgcgg ttgggctact  300
gctctccact tgtccaagaa gaattacgaa gtttgcattg ttgacaacct tgtaagacgt  360
cttttcgacc accagcttgg acttgagtca ttgactccta ttgcctccat tcatgaccga  420
atcagccgat ggaaggcttt gacagggaaa tcaattgagt tgtacgttgg tgatatctgt  480
gatttcgaat tcttagctga gtcttttcaag tcttttgagc cggattcagt tgtccacttt  540
ggggaacaga gatccgctcc ttactcgatg attgaccggt ccagagcagt ttatacacag  600
cacaacaatg tgattgggac tctcaacgtt ctctttgcta taaaagagtt tggagaggag  660
tgtcatcttg taaaacttgg gacgatgggt gagtatggaa ctccaaatat tgacatcgag  720
gaaggttata taaccataac ccacaacggt agaactgaca ctttgccata ccccaagcaa  780
gctagctcct tttatcatct tagcaaagtt catgattcgc acaacattgc ttttacttgt  840
aaggcttggg gtattagagc cactgatctc aaccaaggag ttgtttatgg agtgaagact  900
gatgagacag agatgcatga ggaactccgt aaccgactgg attacgatgc tgtgtttggt  960
acagcactta accggttctg tgtgcaagct gctgttggtc acccacttac agtttatggt  1020
aaaggtggtc aacgagagg ctaccctgat ataagagaca cggttcaatg tgttgagatc  1080
gctatagcaa acccggcaaa agctggtgag ttccgggtct tcaaccaatt tacagaacag  1140
ttttcagtca atgaactggc ttcactcgtc actaaagcgg gttcaaagct gggctagac   1200
gtgaaaagga tgacggtgcc taacccgaga gtggaggcag aagaacatta ctacaacgca  1260
aagcacacta agctgatgga acttggactt gagcctcact atctatctga ctcacttctt  1320
gattcgttgc tcaactttgc tgttcagttt aaagatcgtt tggacacgaa acaaatcatg  1380
cctagtgttt cctggaagaa gattggcgtc aagactaagt ccatgaccac atag        1434

SEQ ID NO: 8           moltype = DNA   length = 1515
FEATURE                Location/Qualifiers
source                 1..1515
                       mol_type = unassigned DNA
                       organism = Arabidopsis thaliana
SEQUENCE: 8
atggtgagtc ttctatcttt tttcttgctt ctactcgtcc ccattttctt cttgttaatc  60
ttcaccaaga agatcaagga gtcaaaacaa aatcttcctc ctggcccagc aaagcttccg  120
atcatcggaa acctacacca gctccaaggg ttgcttcata atgtcttca cgatctctcc  180
aagaaacacg gacctgtgat gcatctccgt ctagggtttg cccaatggt cgtaatttca  240
tcaagtgaag cagctgaaga agctcttaaa acacatgacc ttgagtgttg ttcaagacct  300
atcactatgg cctcaagggt ttttcgcgt aacggtaaag acatcggatt gggggtttac  360
ggtgatgaat ggagagagct gcgtaagctt tcggttcgcg aattctttag cgtgaaaaaa  420
```

```
gttcaatcct tcaagtatat tagagaggaa gagaatgact tgatgatcaa gaaactgaaa    480
gaattggctt cgaagcaatc tccggtggat ttgagcaaaa tcctctttgg tctcactgcg    540
agtatcatat tcagaaccgc cttttggacaa agtttctttg ataacaagca tgtcgatcag   600
gaaagcatca aagaactgat gtttgaatct ctgagcaata tgacttttag attctctgat    660
tttttcccta ctgctggtct taaatggttt ataggcttg tgtcaggcca acataaggag    720
ctttacaacg tcttcaacag ggttgatact tttttaatc atatagttga tgatcatcac    780
tcgaagaaag caactcaaga tcgtcctgat atggtcgacg ctatcttaga tatgatagat    840
aatgaacaac aatatgcatc tttcaagctc accgttgatc atctcaaagg agtcctctca    900
aatatatatc acgctggaat tgacacaagc gccatcacct tgatttgggc gatggcagag    960
ctcgttagaa acccgcgggt aatgaagaaa gctcaagacg agatccgaac ttgcattgga   1020
atcaaacagg aaggaagaat catggaagaa gatcttgata agcttcaata cttgaagctt   1080
gtggtgaaag aaaccttaag actcaccca gcagctcctc ttttacttcc tcgagaaaca   1140
atggctgata tcaagattca aggctacgac attcctcaga aaagagctct tcttgttaat   1200
gcatggtcta taggacgaga tccggaatcc tggaaaaatc ctgaagagtt taacccggag   1260
aggtttattg attgtcctgt ggattacaag ggacatagct ttgagttgtt accatttggt   1320
tctggtcgga gaatttgtcc aggaatagct atggcgatcg caaccattga attgggggctc  1380
ttgaatttgc tctacttctt tgattggaat atgcctgaga gaagaaaga tatggacatg    1440
gaagaagctg gtgatctcac tgttgataag aaagttcctc ttgagcttct gccagttatt   1500
cgcatcagtt tgtag                                                     1515

SEQ ID NO: 9          moltype = DNA  length = 1170
FEATURE               Location/Qualifiers
source                1..1170
                      mol_type = unassigned DNA
                      note = Pseudomonas syringae pv. tomato str. DC3000
                      organism = Pseudomonas syringae
SEQUENCE: 9
atggtcatga ccgtcttgaa gatgaccgac ctcgatctgc aaggtaaacg tgtactgatc    60
cgcgaagacc tcaacgtccc gataaaggac ggcgttgtca gcagcgatgc acgtattctt   120
gcttcgctgc cgaccatcag gctgcgcgct gaaaaaggcg ggctgtcat ggtctgctcg    180
caccttggcc gtccgaccga gggcgagttt tctgctgaaa acagcctcaa gccggttgct   240
gaatacctga gcaaggcatt gggtcgtgac gttccgctgg tcgccgatta cctgacggc    300
gttgacgtca aggcgggcga tatcgtgctg ttcgagaacg ttcgcttcaa caagggcgag   360
aaaaagaacg ccgacgagct ggcgcagaag tacgcggccc tgtgcgacgt gttcgtgatg   420
gacgctttg gcaccgctca ccgcgctgaa ggctcgacc acggcgtggc caaatacgcc   480
aaggttgccg ctgctggccc gttgctggct gccgaactgg aagcgctggg caaggcgctg   540
ggcgctccgg ctcagccaat ggctgctatt gttgccggct ccaaagtgtc caccaagctg   600
gacgtgctca acagcctgag cgcgatctgc gatcagttga ttgttggcgg cgggattgcc   660
aacaccttc tggctgcagc cggtcacaag gtcgtaaat cgcttacga gccagacctg      720
ctcgacaccg cgcgccat tgccgccaag gtcagcgtgc cgttgccgac tgacgtggtg    780
gttgccaagg aattcgccga gagtgccact gcaaccgtca agctgatcgc cgatgtggcc   840
gacgacgaca tgattctgga tattggtcca cagactgctg cgcacttcgc cgaactgttg   900
aaatcttccg ggactatcct gtggaacggt ccggttggtc tgttcgaatt cgaccagttg   960
ggtgaaggca ccaaaacgct ggccaaggcc attgctgaaa gcaaagcgtt ctccatcgcg   1020
ggtggtggcg caccctggcc cgcgatcgac aagtacggtg tggcagatca gatttcctat   1080
atttcgaccg gtggcggtgc gttcctcgaa ttcgtggaag gcaaggttct gccagcggtt   1140
gaaatgctcg aacaacgtgc cagggcctag                                    1170

SEQ ID NO: 10         moltype = DNA  length = 1188
FEATURE               Location/Qualifiers
source                1..1188
                      mol_type = unassigned DNA
                      organism = Zea mays
SEQUENCE: 10
atgagtctca taagagggat gggcaacgtt gccaagagat ggaaagaact caatggcttg    60
aattactgga agggcctagt tgatccgctc gacctcgacc tccgtaggaa catcatcaac   120
tacggtgagc tctcccaggc aacctacacc gggctgaaca gggagagaag atcaaggtac   180
gctgggtctt gcctcttcaa ccgcagagac ttcctcagca gggtggatgt atcaaacccg   240
aacctgtatg agatcacgaa gttcatatac gcgatgtgca ctgtcagctt acctgacgg    300
ttcatggtca agtctctctc aaaggctgca tggagcaggc agtcgaattg gatgggggttt  360
gttgcagtag ctacgacga gggcaaggaa ctgcttggga ggcgggacgt ggtggtggcg    420
tggcgtggca ccataaggat ggtagagtgg gtcgatgatc ttgatatttc cttggtgcct   480
gcttcggaaa tagttcttcc aggcagcgca gccaaccct gtgtgcatgg agggtggctt    540
tcagtctaca cgagtgctga tccagggtca cagtacaaa aagagagac aagacatcag    600
gtgttaaacg aggtgaaaag gatacaggat ctgtacaagc cagaggagac gagcatcacc   660
ataacaggcc acagctagg agcagcactt gccaccatca acgcaaccga catcgtctcc   720
aatggctaca cgaggagctg ctgccctgtg tccgcgttcg tattcgggag ccccagagtc   780
ggaaaccctg atttccagaa ggcgttcgac agcgcggcg acctgaggct gctccgcgtc    840
cggaactctc ccgacgtggt cccaaaatgg ccaaagctag ggtacacgga tgtcggccga   900
gagctgatga tcgacacagg agaatcgccg tacctgaagg cccctggaaa ccccctgaca   960
tggcatgaca tggagtgcta catgcacggg gtgcgctggg ctcaggggag cagcggaggg  1020
ttcgagctgt tggtcgatcg ggacgttgct ttggtgaaca agcatgaaga tgcgctgaga  1080
aatgagttcg ctgtcccacc gtcgtggtgg gtggtgcaga acaaaggtat ggtgaaaggc  1140
aaggatggcc ggtggcatct ggccgaccat gaggaggatg atgactag               1188

SEQ ID NO: 11         moltype = DNA  length = 1539
FEATURE               Location/Qualifiers
source                1..1539
                      mol_type = unassigned DNA
```

```
                      organism = Arabidopsis thaliana
SEQUENCE: 11
atggctactc ttttagccac tcctatcttc tctcctttag cttcttctcc agcaaggaac    60
cgtctttctt gctctaagat ccgtttcggt tccaaaaatg ggaaaattct caattctgat   120
ggtgcccaga agttgaatct ctcaaaattc cgtaaacccg atggccaaag atttctacaa   180
atgggttctt ctaaagagat gaactttgag agaaaactct cagtccaagc tatggatggt   240
gcaggaacag gaaacacatc aacgatctct cgtaacgtaa ttgcgataag tcacttgttg   300
gtatcacttg ggatcattct tgctgcagac tatttcttga agcaggcgtt tgtagcagcg   360
tctattaagt tcccaagtgc tttgtttggg atgttctgta ttttctctgt tcttatgata   420
tttgattcgg ttgttcctgc tgctgcaaat ggtttgatga atttcttcga gcctgcgttt   480
ctgtttatcc aaagatggct tcctttgttc tatgttcctt ctcttgttgt tcttcctctt   540
tctgttagag atattccggc tgcttcaggt gtcaaaatct gctacattgt agccggtgga   600
tggttggcgt cactttgtgt agcagggtac acagctattg cagtgagaaa aatggtgaaa   660
accgaaatga cggaagccga gcctatggca aaaccatcac cattttcaac acttgagcta   720
tggagttgga gtggaatctt tgttgtgtcg tttgttggtg ctctgtttta ccctaattca   780
ttggggacaa gtgcaagaac ttctctccct ttccttcttt cttcaactgt gctaggttac   840
attgtaggtt ctgggttgcc atcttctatt aagaaagttt tccatccgat aatctgctgc   900
gcgctatctg cagtacttgc tgctctagct tttgggtatg cttcaggatc tggacttgtt   960
cctgttttag gaaactacct taccaaagta gcatcagatc ctggtgctgg tgacatctta  1020
atgggttttc ttggctctgt cattctctct ttcgctttct ccatgttcaa acaaagaaag  1080
ctcgtgaaga ggcacgcagc tgagatcttc acatctgtga tagtttcaac ggtattctcg  1140
ctctactcca ctgctcttgt tggacgttta gtcggttcag aaccttcttt aacgttttca  1200
atcctacctc gctgcatcac ggttgcattg gcccttagca ttgtatcact ctttgaaggg  1260
accaattcgt ctcttacagc agctgtagtc gttgtgactg tctgattgg agctaacttt   1320
gtacaagttg ttcttgacaa actgcgttta cgtgatccaa ttgctcgggg aattgcaact  1380
gcttcaagtg ctcatggact tggaacagca gctttgtcg ctaaggagcc agaggctctt   1440
ccctttgtg caatagctta tgctcttacc ggaatcttcg gatcgttact gtgttctgtt  1500
cctgccgtcc gacagagttt gctagcggtc gtcggctag                         1539

SEQ ID NO: 12             moltype = DNA  length = 936
FEATURE                   Location/Qualifiers
source                    1..936
                          mol_type = unassigned DNA
                          organism = Zea mays
SEQUENCE: 12
atggctcgca acgaggagaa ggcgcagtca atgctgaacc gcttcatcac gatgaagcag    60
gaggagaagc gcaagccccg agagcgccgg ccctacctcg cctccgagtg ccgcgacctc   120
gccgacgccg agcgctggcg ctctgagatc ctccgcgaga tcggcgccaa ggtcgccgag   180
atccagaacg agggtctcgg cgagcaccgc ctccgcgacc tcaacgacga gatcaacaaa   240
ctcctccgcg agcgcggcca ctgggagcgc cgcatcgtcg agctcggcgg ccgcgactac   300
tcccgcagct ccaacgcgcc gctcatgacc gacctcgacg gcaacatagt cgccgtcccc   360
aaccctcgg gtcgcggacc ggggtaccgc tactttggcg cggccaggaa gctccctggc   420
gtgcgggagc tcttcgacaa gccgcctgag atgcggaagc gacgcacccg ctacgagatc   480
cacaagcgca tcaacgccgg gtactacgga tactatgacg atgaggacg cgtgctagag   540
cgccttgagg gccctgccgg gaagcgcatg cgggaggaga ttgtttcaga gtggcaccgt   600
gtggaacggg tgcggcggga ggccatgaag gggtgtgatg acggtgaggt ggctgcggct   660
ggagggcgca gcggggaggc tgctagagag gtgctgtttg aggggtgga ggaggagttc   720
gaagaggaga ggaagcgtga ggaagagaag agggagaggg agaaaggcga ggaagttggg   780
agggaattcg ttgcacatgt gccgctacct gatgaaaagg agattgagcg catggtatta   840
gagaggaaga agaaggagct gcttagcaag tatgccagtg attccctgct ggttgagcag   900
gaggaggcca aggagatgct caatgtccga cgctag                             936

SEQ ID NO: 13             moltype = DNA  length = 2049
FEATURE                   Location/Qualifiers
source                    1..2049
                          mol_type = unassigned DNA
                          organism = Zea mays
SEQUENCE: 13
atggaccttg cacggagagg cggtgccgca ggcgcggacg acgaggggga gatcgagagg    60
cacgagccgg cgcccgagga catggagtcc gaccccgcag cggcgcgcga agggagctg   120
gagctggagc gggtgcagtc gtggcggag caggtgactc tgcgcggcgt ggtggcggcg   180
ctgctgatcg gcttcatgta cagcgtgatc gtgatgaaga tcgcgctcac cacggggctg   240
gtgcccacgc tgaacgtctc cgcggcgctg atggcgttcc tggcgctccg cggtggacg   300
cgcgtgctgg agcgcctcgg cgtggcgcac cgcccctcgc cgcaggaac tgcgtc       360
atcgagacct cgccgtcgc gtgctacacc atcgcgttcg gcgtgggtt cggctccacg   420
ctgctgggcc tggacaagaa gacgtacgag ctggccgggg cctcgccggc caacgttccg   480
ggcagctaca aggaccctgg gttcggctgg atggccggat cgtcgcggc gatcagcttc   540
gccggcctcc taagcctgat cccctcaga aaggttctgg tcattgacta caagctaact   600
tacccaagcg ggactgcgac cgctgttctc ataaacggt tccacaccaa gcaaggagac   660
aagaacgcaa ggatgcaagt ccgaggggttc ctcaagtact tgggctcag cttcgtgtgg   720
agctttttcc agtggttcta cacaggcggt gaagttgcg gctttgttca gtttcctacg   780
ttcggtctga aggcctggaa gcagacgttc ttctttgatt ttagcctcac gtacgttggt   840
gcggggatga tctgttcgca cctcgtgaac atctccaccc tccttggtgc catcctgtca   900
tggggatac tgtggccact catcagcaag cagaaaggga agtgtaccc tgcgaacata   960
cctgagagta gcatgaaaag cttatacggt tacaaggcct tcctctgcat agctctgatc  1020
atgggagacg gtacataca cttctttaaa gtctcggtg tcactgttaa gagtctgcat  1080
caacggctga gccgcaaacg tgctaccaac agagtggcaa acggtggaga cgaaatggcc  1140
gcgcttgacg acctacagcg tgacgagatc ttcagcgacg ggtcttttcc cgcctgggca  1200
gcttacgccg ggtacgcggc gctgaccgtc gtctcagcgg tcatcatccc gcacatgttc  1260
```

```
cggcaggtca agtggtacta cgtgatcgtg gcctacgtcc tcgcccctct cctcggcttc   1320
gccaactcct acggcacggg gctcaccgac atcaacatgg cctacaacta cggcaagatc   1380
gcgctcttca tcttcgcggc ctgggccggc agggacaacg cgtcatcgc gggcctcgcc    1440
ggcggcaccc tggtgaagca gctggtgatg gcgtccgcgg acctgatgca cgacttcaag   1500
acgggccacc tgaccatgac gtcgcccagg tccctgctcg tggcgcagtt catcgggacg   1560
gccatgggct gcgtcgtcgc gcccctcacg ttcctgctct ctacaacgc gttcgacatc    1620
gggaacccca ccgggtactg gaaggcgccg tacggcctca tctaccgcaa catggcgatc   1680
ctcggcgtgg agggcttctc cgtgctgccc aggcactgcc tcgcgctctc cgctgggttc   1740
ttcgccttcg ccttcgtctt cagcgtcgcc cgggacgtcc tgccgcggaa gtacgccagg   1800
ttcgtgcccc tgcccatggc catggccgtg ccgttcctcg tgggcgggag cttcgcgatc   1860
gatatgtgcg tcgggagcct ggccgtcttt gtctgggaga aggtgaacag gaaggaggcc   1920
gtgttcatgg tgcctgcggt tgcgtccggt tgatctgtg gagacggcat atggaccttc    1980
ccgtcttcca tttctcgctct ggccaagatc aagccaccga tttgcatgaa gttcactcct   2040
ggaagctag                                                            2049

SEQ ID NO: 14           moltype = DNA  length = 1362
FEATURE                 Location/Qualifiers
source                  1..1362
                        mol_type = unassigned DNA
                        organism = Arabidopsis thaliana
SEQUENCE: 14
atggctaaag tttattggcc ttatttcgat cctgaatatg agaacttgag ctccagaatc     60
aatcctccaa gtgtttctat agataacact agctgcaaag aatgcactct tgtcaaggtg    120
gacagtatga acaaacctgg aatactactt gaagttgtgc aagtcctaac cgatctcgat    180
ctcactatca ctaaagctta tatctcttct gatggtggat ggttcatgga cgtattccat    240
gtcaccgatc aacaaggaaa caaggttact gatagcaaca ccatcgatta catcgagaag    300
gtgttaggac caaagggtca tgcttccggc tcacaaaaca cttggcctgg taaaagagtc    360
ggtgtccatt cattaggcga ccacacatcg atagagatta ttgctcgtga tcgtcctggt    420
ctcttgtcgg aggtttcagc cgtactagca gacctcaaca ttaatgtggt ggcagctgaa    480
gcatggactc acaaccgtag gattgcgtgt gtcctctatg tgaatgacaa tgcaacttct    540
agagccgttg atgatccaga aagattgtct tccatggaag aacagcttaa caatgtgctg    600
cgtgggtgcg aagaacaaga tgagaaattt gctcggacga gtctctccat tgggtcgact    660
cacgttgatc gaaggcttca tcagatgttt ttcgctgata gagactacga agcagtgact    720
aagcttgatg attctgcttc ttgcgattc gagcccaaat tcacggttga gcattgtgaa     780
gagaaaggtt actccgtgat aaacgtgagc tgcgaggatc gaccaaagct catgtttgac    840
attgtatgca cgcttacgga tatgcaatac attgtgtttc acgccacgat ttcatcaagc    900
ggctctcatg cttctcagga gtatttcatc agacacaaag acggttgcac tcttgacaca    960
gaaggagaga agagagagt tgtcaaatgt ctggaagctg caatccatag acgagtcagc    1020
gagggttgga gtttggagct ctgcgcaaag gacagagtga ttactgtcg ggaagtgaca    1080
aggattctga gagagcacgg gctatcagtg tcgagagctc gtgtgacaac agtaggagaa   1140
caagccgtca acgttttcta tgtgaaagat gcttcaggga atccagtgga tgtgaagacg   1200
attgaggcgt acgcggagaga gattggacac agtatgatga ttgacttcaa gaataaagtt   1260
ccgagcagaa aatggaaaga agaaggtcaa gccggaacag gaggaggatg gccaaaaacc   1320
agtttcttct ttgggaattg gctggagaag ttactgcctt ag                       1362

SEQ ID NO: 15           moltype = DNA  length = 1005
FEATURE                 Location/Qualifiers
source                  1..1005
                        mol_type = unassigned DNA
                        organism = Escherichia coli
SEQUENCE: 15
atggcgcaag ttagcagaat ctgcaatggt gtgcagaacc catctcttat tccaatctc      60
tcgaaatcca gtcaacgcaa atctcccttta tcggtttctc tgaagacgca gcagcatcca   120
cgagcttatc cgatttcgtc gtcgtggga ttgaagaaga gtgggatgac gttaattggc     180
tctgagcttc gtcctcttaa ggtcatgtct tctgtttcca cggcgtgcat gatgaatcca    240
ttaattatca aactgggcgg cgtactgctg atagtgaag aggcgctgga acgtctgttt     300
agcgcactgg tgaattatcg tgagtcacat cagcgtccgc tggtgattgt gcacggcggc    360
ggttgcgtgg tggatgagct gatgaaaggg ctgaatctgc cggtgaaaaa gaaaaacggc    420
ctgcgggtga cgcctgctga tcagatagac attatcaccg gagcactggc gggaacggca    480
aataaaaccc tgttggcatg ggcgaagaaa catcagattc ggccgtagg tttgttttctc    540
ggtgacggcg acagcgtcaa agtgaccag cttgatgaag agttaggtca tgttggactg     600
gcgcagccag gttcgcctaa gcttatcaac tccttgctgg agaacggtta tctgccggtg    660
gtcagctcca ttggcgtaac agacgaaggg caactgatga cgtcaatgc cgaccaggcg    720
gcaacggccg tggcggcaac gctgggcgcg gatctgattt tgctctccga cgtcacgggc    780
attctcgacg gcaaagggca acgcattgcc gaaatgaccc cgcgaaagc agaacaactg     840
attgagcagg gcattattac tgacggcatg atagtgaaag tgaacgcggc gctggatgcg   900
gcccgcacgc tgggccgtcc ggtagatatc gcctcctggc gtcatgcgga gcagcttccg   960
gcactgttta acggtatgcc gatgggtacg cggatttttag cttag                  1005

SEQ ID NO: 16           moltype = DNA  length = 1674
FEATURE                 Location/Qualifiers
source                  1..1674
                        mol_type = unassigned DNA
                        organism = Glycine max
SEQUENCE: 16
atggcgctta aaccctatc cactttcctc tcacctcttt ctcttcccaa caccaaattc       60
ccgcaattcc tcaccaccaa gccttcctc attctctgcg agttcccctcg ctctcagaaa    120
tcgcgtttgt tcgccgccga ttcggaaggc accggcgccg ccgctccttc tcccggcgag    180
aagttcctcg aacgccagca gtcctccgaa gatgctaaga tcattctcaa agaaaacaag   240
```

```
aagaagagaa agaagaaaga caatgctata aaagcttcta gagccgtcgc ttcttgctac    300
ggctgcggcg ctccgttaca cacttccgat gccgatgccc ctggctacgt tgatcccgaa    360
acctatgaat tgaagaagaa acaccaccag cttcgaaccg ttctgtgtag gcggtgccgg    420
cttttgtctc atggcaagat gataactgcc gttggagggc acggaggata tcctggcggt    480
aaattattcg tcactgctga agagcttcga gaaaagttgt ctcacctgcg tcacgagaaa    540
gctctaatcg tcaaattggt tgatattgtt gacttcaatg gcagttttt gtctcgtgtg    600
cgagatcttg ctggttctaa tccaataata ttggtggtga ctaaggttga tctccttcct    660
agagatactg atcttcattg tgttggggat tgggttgtag aggctactat gagaaagaag    720
ctaaatgttc tcagtgtcca tctgaccagt tccaaatcat tggttggaat aactggagtg    780
atatcggaaa tccagaaaga gaagaaggga cgagatgttt acattctggg ttcagctaat    840
gttgggaaat ctgctttcat caatgcttta ctaaaaacaa tggctataaa tgatccagtg    900
gctgcatctg cacaaagata caaaccaata caatctgcag ttcctggaac taccttaggg    960
ccaattcaaa ttaatgcttt cctaggagga gggaaattgt acgacactcc tggagttcat   1020
ctctaccata ggcaaaatgc agttgttcat tctgaagatc tacccatcct tgctcccaaa   1080
agccgactga ggggcctgtc tttcccaagt tctatattat cttcagtaga ggaaggagct   1140
tccaccatag tgaatggctt gaatgcattt tcaatatttt ggggaggtct tgttagaatt   1200
gatgtcttga aggttctccc agaaacttgt ttgacatttt atggacccaa gagaatacca   1260
attcatatgg tacccacaga gcaagcagtt gaatttatc agacagaact tggagttctg   1320
ctgaccccac caagtggagg agaaaatgct gagaactgga aaggacttga atcagaacga   1380
aaattgcaaa ttaaatttga agatgtggac agttatgatc ccaaaccagc ttgtgatata   1440
gctatatcag gtctaggatg gtttactgtt gagccagtta gtcggtcact caaaatctca   1500
caaccaaaac cggtagagac tgctggggaa ttgattttgg ctgtgcacgt ccccaaggct   1560
gttgagattt ttgtgaggtc accaatacca gtaggcaagg ctggagcaga gtggtaccag   1620
tatgtagaat aacagagaa acaagaggaa atgagaccaa aatggtactt ttag           1674

SEQ ID NO: 17            moltype = DNA   length = 1281
FEATURE                  Location/Qualifiers
source                   1..1281
                         mol_type = unassigned DNA
                         organism = Zea mays
SEQUENCE: 17
atggcggcgg cgctcgcctc ctcccgctac tgctggagcc gccgtcgct gccgccccaa    60
ccgaccgcg gccgccgctc cgtcactagc tgcgcgctct ccggacgaga gaaagaaac    120
tccttagct ggagagagtg tgcaatttct gttgcattgt cagttggact aatcactggt    180
gcaccaacgt ttggaccacc ggccctatgct tcttctcttg aacctgttct tccagatgtg    240
tctgttctta tctctggacc tcccattaaa gatccaggtg ctttattgag atatgcttta    300
ccaatagata ataaagctat ccgtgaagtt caaaagccgc tggaggatat cactgacagc    360
ctcaaggttg ctggtgttag agccttggat tcagttgaaa gaaatgtcag acaagcatcg    420
aaagcactga acaatgggag aagcttaatt cttgctggcg tctgtgaacc aaaaagagca    480
aatggagaag agttgttgaa taagttggct gttggatttg aggagcttca agaattgtg    540
gaagacagaa atagggatgc agtagctcca aagcagaaag agcttctcca gtatgttgga    600
actgtagaag aagacatggt cgatggcttt ccctttgaaa taccagaaga gtacagcaac    660
atgcctcttc tcaaaggaag agctactgtg gatatgaagg ttaagattaa ggacaatccc    720
aacatggaag actgtgtatt taggatagtt ctgatggat ataatgctcc tgtgactgct    780
gggaacttcg tagatcttgt caaacggaaa ttctatgatg gcatggaaat ccaaagagct    840
gatggctttt tgttcaaac tggagatcca gaggggccag ctgagggctt atcgatccc    900
agcaccggca aaatccgtac ggtacctctt gaaattatgg ttgatggtga taaggcgcct    960
gtatatggtg aaacacttga gaacttggt cgctacaagg ctcaaacaaa actccctttc   1020
aacgctttg gaacaatggc tatggcaaga gaagaatttg atgacaattc tgcttctagc   1080
caagtatttt ggctcttgaa agagagtgag ctaacaccaa gcaatgccaa tatattggac   1140
gggcggtacg cagtatttgg atatgtaact gagaatgagg actacctggc tgacgtcaaa   1200
gttggagatg tcatcgaatc aatccaagtc gtctcaggct tggacaacct tgtcaaccca   1260
agctacaaga ttgtaggata g                                             1281

SEQ ID NO: 18            moltype = DNA   length = 435
FEATURE                  Location/Qualifiers
source                   1..435
                         mol_type = unassigned DNA
                         organism = Arabidopsis thaliana
SEQUENCE: 18
atgatgcaag aattaggctt acaacgtttc tcaaacgacg tcgttcgctt agacctcact    60
cctcttctc aaacctcatc tacttctctt tccatcgacg aagaggaatc aacggaagcc   120
aagatccgac ggctgatatc ggagcatcct gtgatcatct tcagtagatc ttcatgttgc   180
atgtgccacg tcatgaagag actcttagca acgatcggcg taatccccac cgtcatcgag   240
ctcgatgatc acgaggtttc ctctcttccc acggctctac aagatgaata ttccggtggc   300
gtctccgtcg ttggtcctcc gccggcggtt tcattggcc gtgagtgcgt cggaggtctt   360
gagtcccttg tcgctcttca cttaagtggt caacttgttc ctaagcttgt ccaagttgga   420
gctctttggg tatag                                                    435

SEQ ID NO: 19            moltype = DNA   length = 1530
FEATURE                  Location/Qualifiers
source                   1..1530
                         mol_type = unassigned DNA
                         organism = Escherichia coli
SEQUENCE: 19
atggcttcct ctatgctctc ttccgctact atggttgcct ctccggctca ggccactatg     60
gtcgctcctt tcaacggact taagtcctcc gctgccttcc cagccacccg caaggctaac   120
aacgacatta cttccatcac aagcaacggc ggaagagtta actgcatgca ggtgtggcct   180
ccgattggaa agaagaagtt tgagactctc tcttaccttc tgaccttac cgattccggt   240
```

```
ggtcgcgtca actgcatgca ggccatgagc aacaatgaat tccatcagcg tcgtctttct    300
gccactccgc gcggggttgg cgtgatgtgt aacttcttcg cccagtcggc tgaaaacgcc    360
acgctgaagg atgttgaggg caacgagtac atcgatttcg ccgcaggcat tgcggtgctg    420
aataccggac atcgccaccc tgatctggtc gcggcggtgg agcagcaact gcaacagttt    480
acccacaccg cgtatcagat tgtgccgtat gaaagctacg tcaccctggc ggagaaaatc    540
aacgcccttg ccccggtgag cgggcaggcc aaaaccgcgt tcttcaccac cggtgcggaa    600
gcggtggaaa acgcggtgaa aattgctcgc gcccataccg gacgccctgg cgtgattgcg    660
tttagcggcg gctttcacgg tcgtacgtat atgaccatgg cgctgaccgg aaaagttgcg    720
ccgtacaaaa tcggcttcgg cccgttccct ggttcggtgt atcacgtacc ttatccgtca    780
gatttacacg gcatttcaac acaggactcc ctcgacgcca tcgaacgctt gtttaaatca    840
gacatcgaag cgaagcaggt ggcggcgatt attttcgaac cggtgcaggg cgagggcggt    900
ttcaacgttg cgccaaaaga gctggttgcc gctattcgcc gcctgtgcga cgagcacggt    960
attgtgatga ttgctgatga agtgcaaagc ggctttgcgc gtaccggtaa gctgtttgcc   1020
atggatcatt acgccgataa gccggattta atgacgatgg cgaaaagcct cgcgggcggg   1080
atgccgcttt cgggcgtggt cggtaacgcg aatattatgg acgcaccgc gccgggcggg    1140
cttggcggca cctacgccgg taacccgctg gcggtggctg ccgcgcacgc ggtgctcaac   1200
attatcgaca agaatcact ctgcgaacgc gcgaatcaac tgggcagcg tctcaaaaac     1260
acgttgattg atgccaaaga aagcgttccg gccattgctg cggtacgcgg cctgggtcg    1320
atgattgcgg tagagtttaa cgatccgcaa acgggcgagc cgtcagcggc gattgcacag   1380
aaaatccagc aacgcgcgct ggcgcagggg ctgctcctgc tgacctgtgg cgcatacggc   1440
aacgtgattc gcttcctgta tccgctgacc atcccggatg cgcaattcga tgcggcaatg   1500
aaaatttttgc aggatgcgct gagcgattag                                    1530

SEQ ID NO: 20          moltype = DNA  length = 1473
FEATURE                Location/Qualifiers
source                 1..1473
                       mol_type = unassigned DNA
                       organism = Synechocystis sp.
SEQUENCE: 20
atggcttcct ctatgctctc ttccgctact atggttgcct ctccggctca ggccactatg     60
gtcgctcctt tcaacggact taagtcctcc gctgccttcc cagccacccg caaggctaac    120
aacgacatta cttccatcac aagcaacggc ggaagagtta actgcatgca ggtgtggcct    180
ccgattggaa agaagaagtt tgagactctc tcttaccttc ctgaccttac cgattccggt    240
ggtcgcgtca actgcatgca ggccatgacc ccagaattga atcctaattt tccccgaagaa    300
actacctccg atgcttggct gaccccagca gatgccggcc aggatggtga tgcccaggaa    360
ccggcggaag atgggggaga agaaggagta gtgtcggaag aactggccct gcctgaggac    420
ttacctccta tggatgccat ggtggcggca gtggaagaaa tgactccggt ggtggtgccc    480
gaaactgtac cagaaacaga aaccccagcc ttagaggatt tggtcgccca aaagaccgcc    540
ctggaaaagg acattgccgc tctgcaacgg gaaaaagccc agtggtatgg ccagcagttc    600
cagcaattac agcgggaaat ggcccggtta gtggaggaag gcaccaggga attagggcaa    660
agaaaagcag ctctggaaaa ggaaattgag aagttagagc gccgtcagga acggattcaa    720
caggaaatgc gtaccacttt tgccggggct tccaggagt tggccatccg cgtgcagggc    780
tttaaggatt atttggtggg gagtttgcag gatttgattt ccgccgccga ccagttggaa    840
ttaggggtgg gggacagttg ggagtcttcc tctacccatg gggatgcgat tattgaaaat    900
gccgacccaa ctccggtggt gagttttgcg gagcaggtt ttagtagcca aaaacgacaa     960
atccaagctt tgctggagca ataccgcact cgccctgatt attacggtcc cccttggcag   1020
ttgcgtcgta cctttgagcc agtccacgcc gaacggattg agaattggtt ctttaccctg   1080
ggcggtcggg gagcaatcct cagtttagac agtcgtttac aaaatatttt ggtgggttca   1140
gcggcgatcg ccatttttgaa tcagctctac ggcgatcgtt gtcgggcgtt aattttggcg   1200
gccacccccag aaagattggg ggaatggcga cggggtttac aggattgttt gggtatttcc   1260
cgcagtgact ttgggcccaga ccggggcatt gttttgtttg aatcggccaa tgccttgatt   1320
cagcggggcg aaagattggt cggcgatcgc caaatgccgt tggtgttggt ggatgaaaca   1380
gaggaacaaa ttgacttagc cctgttgcaa ttcccccttt tactggcctt tgcacctagt   1440
taccaagtcg gaggcagtaa ctattttttct tag                                1473

SEQ ID NO: 21          moltype = DNA  length = 1215
FEATURE                Location/Qualifiers
source                 1..1215
                       mol_type = unassigned DNA
                       organism = Zea mays
SEQUENCE: 21
atggccggcg aactgcgcca ccgccgcgcg ccgtcggagg acgagggcgt cgcctcctct     60
caaagactcg actccgcccc cgcaggcaac ggcaaggctg cacttcgtc cggcggcggc    120
gaggggcgg agccgcgggg cgggaagagg gacgcgctag ggtggctgga gtggtgccga    180
ggttggatgg ccatcgtggg ggagttcctc ttccagcgca tcgccgccag ccacctggcc    240
aacccgctcg agttgcccc gctcgatggc gtctccatcg tcgtcaccgg cgccaccagc    300
ggcatcgggc tcgagatcgc aaggcaactc gctctcgctg gggcacatgt tgttatggct    360
gtaaggagac ccaaggtggc acaagagttg attcagaagt ggcagaatga aaattcagaa    420
acaggaagac cactaaatgc cgaggtgatg aacttgacg tgctctccct cgactcggtc    480
gtaaaatttg ctgatgcttg gaatgctcgt atggcaccgc tgcacgtgtt gatcaacaat    540
gctggcatct tcgctatagg agaaccccaa cattttccga aggatggaca tgaagaacac    600
atgcaagtga accatcttgc acctgcatta ctggcgatgc tgcttatacc ttcccttctc    660
cgaggttctc ccagcagaat cgttaacgtt aattcaatca tgcacagtgt aggttttgtt    720
gatgctgaag atttcaactt gagaaaacat aaatatagaa gttggttggc gtattcaaat    780
agcaagttgg cacaggtaaa atttagtagc atgcttcata agagaattcc tgcagaagct    840
ggcatcagca taatttgtgc ttctcctgga attgtcgaca cgaatgttac aagagacctt    900
cctaagattg ttgtagctgc ataccgtttt cttccctact tcatattcga tggtcaagaa    960
ggttctagga gtgcactgtt tgcggcatgt gacccccaag ttccagagta ctgtgagatg   1020
ctcaagtcgg aagactggcc agtctgtgct tgcattaact acgactgtaa tccgatgaac   1080
```

```
gcgtctgaag aagcgcacag ccttgaaacc tcgcagctgg tctgggagaa gacgctcgag   1140
atgatcggcc ttccgccgga tgccctggac aagctcatcg ccggagaaac agtgccgtgc   1200
cgttatggac aatag                                                    1215

SEQ ID NO: 22           moltype = DNA   length = 2829
FEATURE                 Location/Qualifiers
source                  1..2829
                        mol_type = unassigned DNA
                        organism = Zea mays
SEQUENCE: 22
atggagggcg acgacttcac gccggagggc ggcaagctcc ccgagttcaa gctagatgcg   60
agacaagcgc agggtttcat ctccttcttc aagaagctgc cgcaggatcc ccgggccgtt   120
cgtctcttcg atcgcaggga ttattacact gcccatggcg agaatgctac gtttatcgca   180
aggacatact accaacacaat gtctgcctta cgtcaactga gtagcaccct tgatggaatc   240
ttaagtgcca gcgtgagcaa ggctatgttt gagaccattg cccgcaacat tttgttggaa   300
aggactgact gtacattgga actctatgag ggaagtgggt caaattggag gttaacaaag   360
tccggaacac ctggaaatat tggtagtttt gaagacattc tgtttgcaaa caatgacatg   420
gaagattcac cagtgattgt tgcttttgttt ccagcgtgcc gggaaagtca gctgtatgta   480
gggcttagtt ttttggatat gaccaatagg aagcttgggt tggctgagtt tcccgaagat   540
agccgattca ctaatgttga atcagctctt gttgcattag ttgcaaggat gtgtcttctc   600
ccagcagatt gtgaaaaatc cattgaccta atccccttc aagacgtcat tagtaactgt   660
aatgttctgt tgactgaaaa aaagaaggct gacttcaaat ccagggatct cgcacaagat   720
cttggtagaa taatcagggg ttctgttgag cctgtacgtg atctactatc tcagtttgac   780
tatgctcttg gtccccttgg agctctttta tcttatgccg agttgctagc agatgacact   840
aactatgaaa attacacaat tgagaagtac aatttgaact gctacatgcg acttgattct   900
gctgcagttc gagcattaaa cattgcagaa gggaaaactg atgtaaacaa gaacttcagt   960
ttgtttggtt tgatgaacag aacttgtact gttgggatgg gaaaaagatt gctgaacaga   1020
tggctgaaac aacctctatt agatgttaat gaaattaata accgactaga catggttcag   1080
gcttttgtag aagacccaga acttcgtcag ggactccggc aacaacttaa aaggatatca   1140
gatattgatc gtctaaacaca tagtctccga aagaaatcag ctaatctgca gcctgttgtt   1200
aagctttatc agtcctgtag cagaatccca tacatcaagg gcattcttca gcaatataat   1260
ggccaatttt caacattgat aaggtcaaag tttcttgaac cgttagaaga atggatggca   1320
aagaatcgat ttggtcgttt ttcttctctt gttgagacag ctattgatct tgctcagctg   1380
gagaatggag agtacagaat atctcctcta tattcttctg acttgggtgt actaaaggat   1440
gagctttctg tggttgaaaa ccacataaac aatctgcacg tggatacagc tagtgatctg   1500
gatctttctg ttgataagca actgaagcta gaaaaaggat cccttggaca tgtgttcaga   1560
atgtcaaaga aagaggaaca gaaagtcagg aagaaactca ctggcagcta cttaatcata   1620
gaaactcgta aagatggtgt aaagttcaca aattcagaag tgaaaaatct aagtgatcaa   1680
taccaggcat tgtttggtga gtacacaagt tgtcagaaaa aggtggttgg tgatgtagtg   1740
agggtttcag gcacattctc agaggtattt gaaaattttg ctgcagttct gtcggagttg   1800
gatgttttac aaagttttgc tgatttggca actagttgcc cagttcctta tgttaggcca   1860
gacatcactg cgtcggatga aggagatatt gttctactgg gtagcagaca tccttgtcta   1920
gaggcacaag atggtgttaa cttatacccc aatgattgca tctctggtga ggggaaaagt   1980
tggtttcaga tcatcactgg accaaacatg ggaggaaaat ccacatttat aagacaggtt   2040
ggtgtaaaatg tattgatggc acaagttggt tcctttgtac cttgtgatca agcaagtatt   2100
agtgtgaggg attgtatttt tgctcgtgtt ggcgctggtg attgccaact tcatggtgta   2160
tcaactttta tgcaagaaat gcttgaaaca gcatccatcc taaaaggcgc ctctgataag   2220
tctcttataa ttattgatga gctggggcgt ggaacttcca catatgatgg atttggtctt   2280
gcatgggcta tctgtgagca tcttatggaa gtgactcgag cgcctacctt gtttgcaacc   2340
catttccatg aactaactgc attagcacat agaaatgatg atgagcacca acacatttca   2400
gacatcggag ttgcaaatta tcacgtgggt gctcacatag acccattaag taggaagtta   2460
actatgcttt acaaggttga acctggtgca tgcgaccaaa gttttggtat tcatgttgca   2520
gaatttgcta attttccaga agctgttgtt gcccttgcga aaagcaaagc agcagagtta   2580
gaagactttt ctactacacc taccttttcc gatgatttga agacgaggt tggatcaaag   2640
cgcaagaggg tatttagccc agatgacatc accagaggag ctgcacgggc tcggcttttc   2700
cttgaggaat tcgccgcatt gcctatggat gagatggatg gagcaagat attggagatg   2760
gccaccaaga tgaaagctga cttgcagaaa gatgcagctg acaatccttg gctccagcag   2820
ttcttctag                                                           2829

SEQ ID NO: 23           moltype = DNA   length = 1035
FEATURE                 Location/Qualifiers
source                  1..1035
                        mol_type = unassigned DNA
                        organism = Arabidopsis thaliana
SEQUENCE: 23
atggagtgga ttcgaggaga aactatcgga tacggaactt ttctacagt aagtctagcg    60
acgcggtcta ataacgattc cggcgagttt cctccgttaa tggctgtgaa atctgcagac   120
tcatacggcg ctgcttctct ggcaaacgag aaatcagttc tagataatct cggagacgat   180
tgcaacgaga tcgtacggtg tttcggcgag gatcggacgg tcgaaaacgg tgaagagatg   240
cataatttgt tcttggaata cgcttctaga ggaagcttag agagttatct taagaaatta   300
gccggtgaag gtgtaccgga atccaccgtg cgtcgcccaca caggatcggt gcttagaggt   360
ctacgacaca tccacgctaa cggattcgct cactgtgatt taaaactcgg gaatattctg   420
ttgttcggtg acggcgccgt taagattgcg gattttggat tggcgaagag aattgggggat   480
ttaacggcgt taaattacgg tgtgcagatt agaggtacgc cgttgtacat ggcgccggaa   540
tctgttaacg ataacagatc cggatcagaa ggtgacgctc gggctttagg atgcgtagta   600
gttgagatgt ttagtggtaa aacggcatgg agtttaaaag aagggtcgaa cttcatgtcg   660
ttgttgttac gcatcggtgt tggtgacgag gttccgatga ttcccgagga gttgtcgaaa   720
caaggaagag atttttttgtc aaagtgtttc gttaaagatc ccaaaaagag atggacggct   780
gagatgcttc taaaccatcc attttgtaacc gtcgatgttg atcacgacgt tttagtcaaa   840
```

```
gaagaagatt tcgttgttaa tatgaaaaca gaggacgtct cgacatcgcc gagatgccca   900
ttcgaatttc ccgattgggt ttcggtttct tccggttcac aaacgatcga ttcgccggat   960
gagagagttg ctagtttggt gactgatatg atccctgatt ggtctgttac caatagctgg  1020
gtcaccgtac ggtga                                                    1035

SEQ ID NO: 24           moltype = DNA  length = 3564
FEATURE                 Location/Qualifiers
source                  1..3564
                        mol_type = unassigned DNA
                        organism = Arabidopsis thaliana
SEQUENCE: 24
atgagaaacc attgcttaga actctcttcc aattgttcct ccattttcgc ttcttccaaa    60
tccaatcctc gtttctctcc ttccaagctc tcctattcca ctttcttctc tcgctctgcc   120
atctattaca gatcaaaacc aaaacaagcc tcgtcttctt cttccttctc cactttcccc   180
ccatgtctca atcggaaaag ctccctcacg catgttctca aacccgtctc agagctcgcc   240
gacaccacta ccaagccttt ttctccggag atcgtcggca agagaaccga tctgaagaag   300
attatgattc tcggcgctgg tccgattgtc attggacaag cttgtgagtt tgattactct   360
ggtactcaag ccttgtaaagc cttaagagaa gagggctatg aggttatcct gatcaattcg   420
aatcctgcca ctatcatgac tgatccgaaa actgctaatc ggacttatat cgctcccgatg   480
actcctgagc ttgtcgagca ggttattgag aaagagaggc ctgacgcttt gttaccaacc   540
atgggtggtc aaaccgcatt gaacctcgcg ttgctcttg ctgagagtgg tgctttggag    600
aaatacggtg ttgaattgat aggagctaag cttggtgcga ttaagaaagc tgaagatcgt   660
gagttgttca aggatgcgat gaagaacatt gggctaaaga ctccaccttc agggattggg   720
accactcttg atgagtgttt tgacattgct gagaaaattg gtgagttccc tttgattatc   780
cgtcctgcgt ttactttagg tggtactggt ggtggaattc gtataacaa agaggagttt     840
gagtctatat gtaaatcggg tttggctgcg agtgcgaaga gtcaagttct tgtggagaaa   900
tccttgttgg gttggaaaga atatgagctt gaggtgatga gagacttagc tgacaatgtt   960
gtcattatct gttccattga gaatattgat cctatgggtg tgcacactgg tgattccatc  1020
actgtgggcac ctgcacagac tctaacggat agagagtacc agcggcttag ggattattcc  1080
attgcgatta tacgggagat tggtgttgga tgtgttgagg ctaatgtgca gtttgctgtc  1140
aaaccggttg atggtgaagt tatgatcata gagatgaacc ctagggtctc aagatcttct  1200
gctcttgctt ccaaggctac agggtttccc attgctaaaa tggctgccaa gttgtctgtt  1260
ggctatacct tggatcagat tcctaatgat atcacggagg aaacaccggc tagcttcgag  1320
ccctccatcg attatgtggt gactaagatt cctcgatttg catttgaaaa gtttccagga  1380
tctcagccat tgctaacgac ccagatgaaa tctgttgggg aatctatggc tctcggccgt  1440
acattccaag aatctttcca gaaagctctg aggtctctgg agtgtggatt ctcgggttgg  1500
ggttgtgcaa aaattaaaga gctagattgg gactgggatc agctgaaata cagcctaaga  1560
gtcccaaatc ctgacaggat ccatgcgata tatgctgcca tgaaaaaggg tatgaaaatt  1620
gatgaaatct acgagttgag catggtggac aagtggttcc taacccagct taaagagctc  1680
gtggacgtcg aacagtatct tatgtccgga accttgtcag agattacaaa agaagacctt  1740
tacgaagtca aaaagcgggg atttagtgac aagcaaatcg cttttgctac aaagacaacc  1800
gaggaagaag tccgtaccaa gcggatttct ctaggagttg ttccatctta caagagagtg  1860
gatacatgtg ctgcagagtt cgaagcgcat acaccataca tgtactcttc atatgatgtt  1920
gaatgtgaat cagctccaaa caacaagaag aaggttttga ttttgggtgg agggcccaac  1980
cgcattggtc aagggattga atttgattac tgttgttgcc acacatcttt cgccttacag  2040
gatgctggat atgagaccat aatgttgaac tcaaatcctg aaacagtatc cacagattat  2100
gatacaagcg ataggctcta ttttgaacct ctcacaatcg aggatgttct caatgttatc  2160
gaccttgaga aacctgatgg cataatagtg caatttggtg gtcaaactcc tctgaaactc  2220
gctctgccga tcaaacatta tttggataag cacatgccca tgagcttgag cggagcggga  2280
cctgttcgca tctggggtac atcacctgac tccattgacg ctgctgaaga cagagagagg  2340
ttcaatgcaa ttctcgacga gctgaagatt gagcagccca agggaggcat tgcaaagagc  2400
gaagctgatg cattgccat agcaaaggag gtagggtacc cagttgtggt aagaccttct  2460
tatgttctag gtggacgagc aatggagatc gtttatgatg acagtagact aataacctat  2520
ttggaaaatg cggtacaagt tgacccagag agacctgttt ggtagataa atatctttct  2580
gatgccattg agatcgacgt tgatacccct actgattcct atggaaatgt ggtgattggt  2640
ggaataatgg agcatatcga acaagctggt gtgcattctg gtgactcagc ttgtatgctt  2700
ccaacacaaa ccatcccagc ttcttgtttg caaactattc gaacatggac cactaagctg  2760
gcgaagaagc taaatgtatg tgggctgatg aactgtcagt acgcaatcac aacatctggg  2820
gatgttttt tgctggaagc caatccccga gcttcccgta ctgtccctt tgtgtcaaaa  2880
gccattggac accctcttgc caagtatgca gcgctggtca tgtcgggcaa atctctcaaa  2940
gatcttaact ttgaaaaaga agttatccct aaacatgtct ctgtgaaaga agctgttttc  3000
ccgtttgaga agttccaagg atgcgatgtg atactcgggc agagatgag aagcacagga  3060
gaagtgatga gcatcagttc tgaattctca agtgcgtttg caatggctca gatcgctgca  3120
ggtcaaaagc tacctctatc aggcacagtc ttcctcagct taaacgatat gaccaaaccg  3180
cacctggaga aaatcgcggt gtccttcctc gagcttgggt tcaaaatagt tgccacctcg  3240
ggaacagctc atttcctgga actgaaaggc atttcagtgg agagagtgtt gaagttgcat  3300
gaaggaagac cacatgctgc tgatatggtg gcgaatggtc agatccattt gatgttgatc  3360
acaagctcgg gtgatgctct tgatcagaaa gatgggagac agctcagaca aatggctcta  3420
gcatacaagg tacctgttat aaccactgtt gctggtgcat tggccactgc tgagggaatc  3480
aagagcttga agtcaagtgc cattaaaatg accgctcttc aggacttctt tgaggtaaag  3540
aatgtatctt ctttgctcgt ctga                                         3564

SEQ ID NO: 25           moltype = DNA  length = 825
FEATURE                 Location/Qualifiers
source                  1..825
                        mol_type = unassigned DNA
                        organism = Glycine max
SEQUENCE: 25
atgagagcca aattgtttgt gttcccaata cgaggcagga actggtgctt ctccagaacc    60
```

-continued

```
atcgatcact ctctctccgc ttcccatgct tcctctcaat cccctcaac cctcaaagac    120
ttgtggacca acatcaacgt tggtgataaa ccctgaaca ccaaaactga gctctttgtc     180
gattacatcg ccaacaagat gaataatgct tggattggct tggagaaggc gccggagggg    240
tctttcaaga acaagattca tgggttgggg ttgcggctct tgtcgcgggt taagccctct    300
gagatatttt tgaagtctat atcgaaggaa atcactagtg ttgaaatcat ttatccatca    360
agtttgaatg ctcaacttgt tcgtcgaaga ctaagcacaca ttgctgtgag gggagcagtt    420
atccatcgga attacttata cggtttagtt tcgttgattc cattgacttc agcacttagc    480
attttacctt tgcctaatgt tccgttcttc tgggttttat ttcgcactta ttctcattgg    540
agagccttgc agggaagtga gaggctgttt caactagtc cagataacag caagacttca    600
aacacttgta catatgaaaa gaaaactgag cacaaggaat ctaaagtca aagacatagt     660
tcaaatgaac cttgttgggt gttgaggcca tccaaagaac ttgagaatct tgtccatcta    720
gaagatggtc aagagagtct tagtcaacat gccatcataa acatttgcaa gatctatgac    780
ttgaacccag tagatgttat aaaatacgag aagtccgtct tttaa                    825

SEQ ID NO: 26          moltype = DNA  length = 621
FEATURE                Location/Qualifiers
source                 1..621
                       mol_type = unassigned DNA
                       organism = Arabidopsis thaliana
SEQUENCE: 26
atggcgaaag agtccaccac catcgacgtc ggcgagccaa gcactgttac caaaagttca     60
agctgatgtcg taaaggacgc gaagaagaag ggctttgtg cagtcgcctc aagaggtggt    120
gccaagagag gtttggctat attcgatttc ctcctccgtt tggcggccat agcagtcact    180
attggggctg cctctgtcat gtacaccgcc gaggaaactc ttcccttctt tactcagttc    240
ctccagttcc aagccggtta cgatgacctt cctgcgtttc agtactttgt gatagccgta    300
gccgtagtcg ctagctatct cgtcctttca cttccattct ccatcgtatc cgttgtccgt    360
ccacatgctg tcgcgccccg gctgatcctc ctcatttgcg atactctggt cgtgacgctc    420
aacacatcag cagcagcagc ggcagcatca atcacctacc ttgcacacaa cggcaaccaa    480
agcaccaact ggctccctat ctgtcagcag tttggagact tctgccagaa cgttagcacc    540
gcggttgtgg ctgattctat cgcgattctc ttcttcatcg ttcttatcat catctcagcc    600
atcgccctca agaggcattg a                                              621

SEQ ID NO: 27          moltype = DNA  length = 1236
FEATURE                Location/Qualifiers
source                 1..1236
                       mol_type = other DNA
                       note = codon optimized Escherichia coli Asparagine
                         synthetase A (AsnA) gene
                       organism = synthetic construct
SEQUENCE: 27
atggcaacag caacatcagc ttctctgttt tcaactgttt cttcatctta ctccaaagct     60
agctccatac cacattcaag actccaatct gtgaaattca actcagtccc tagcttcacc    120
ggtctcaaat caacctctct catctcggga tctgattcct ttccttagc caagactcta    180
cgcggttccg taacgaaagc acaaacatct gacaagaagc cttacggatt caaaatcaac    240
gctatgaaga ccgcctacat cgctaagcag cgccagatct ccttcgtgaa gtcccacttc    300
tctaggcagc tagaggagcg cctaggcctg atcgaggtgc aggcccccat ccttagccgc    360
gtgggtgacg gcacccagga caaccttagc ggctgcgaga aggccgtgca ggtgaaggtg    420
aaggcccctcc ccgacgccca gttcgaggtg gtccactccc tcgccaagtg gaagcgccag    480
acccctcggcc agcacgactt cagcgccggc gagggcctct acaccacat gaaggccctc    540
cgccccgacg aggacaggct ctcccccctc cactccgtgt acgtggacca gtgggactgg    600
gagagggtca tgggcgacgg cgagaggcag ttctccaccc tcaagagcac tgtcgaggcc    660
atctgggccg gcatcaaggc tactgaggct gcggtcagcg aggaattcgg cctcgctcct    720
ttcctccctg accagatcca cttttgtccac tctcaggagc tcctgtctag gtaccctgac    780
ctcgacgcta agggccggga gcgggctatc gctaaggacc tcggtgctgt ctttctggtc    840
ggtatcggtg gaaactgtc tgacggtcac cggcacgatg tccgtgctgc tgattatgat    900
gattggtcga ctccgtcgga gctgggtcat gcgggtctga acggggatat tctggtttgg    960
aatccggttc tggaggatgc gttttgagctg tcgtcaatgg ggattcgtgt tgatgcggat    1020
acgctgaaac atcagctggc actgacgggg gatgaggata gacttgaact tgaatggcat    1080
caggcattac ttcgtgggga aatgccgcag acaattgggg gaggaattgg acaatcaaga    1140
cttacaatgc ttttgcttca attgccacat ataggacaag ttcaatgcgg agtttggcca    1200
gcagcagttc gagaaagtgt accaagtttg ttgtga                              1236

SEQ ID NO: 28          moltype = AA  length = 54
FEATURE                Location/Qualifiers
source                 1..54
                       mol_type = protein
                       organism = Arabidopsis thaliana
SEQUENCE: 28
MVNNVVSIEK MKALWHSEVH DEQKWAVNMK LLRALGMFAG GVVLMRSYGD LMGV            54

SEQ ID NO: 29          moltype = AA  length = 315
FEATURE                Location/Qualifiers
source                 1..315
                       mol_type = protein
                       organism = Arabidopsis thaliana
SEQUENCE: 29
MVGWAIALHG GAGDIPIDLP DERRIPRESA LRHCLDLGIS ALKSGKPPLD VAELVVRELE     60
NHPDFNAGKG SVLTAQGTVE MEASIMDGKT KRCGAVSGLT TVVNPISLAR LVMEKTPHIY    120
LAFDAAEAFA RAHGVETVDS SHFITPENIA RLKQAKEFNR VQLDYTVPSP KVPDNCGDSQ    180
```

```
IGTVGCVAVD SAGNLASATS TGGYVNKMVG RIGDTPVIGA GTYANHLCAI SATGKGEDII    240
RGTVARDVAA LMEYKGLSLT EAAAYVVDQS VPRGSCGLVA VSANGEVTMP FNTTGMFRAC    300
ASEDGYSEIA IWPNN                                                    315

SEQ ID NO: 30            moltype = AA   length = 726
FEATURE                  Location/Qualifiers
source                   1..726
                         mol_type = protein
                         organism = Arabidopsis thaliana
SEQUENCE: 30
MPSHPNFIFR WIGLFSDKFR RQTTGIDENS NLQINGGDSS SSGSDETPVL SSVECYACTQ     60
VGVPAFHSTS CDQAHAPEWR ASAGSSLVPI QEGSVPNPAR TRFRRLKGPF GEVLDPRSKR    120
VQRWNRALLL ARGMALAVDP LFFYALSIGR TTGPACLYMD GAFAAVVTVL RTCLDAVHLW    180
HVWLQFRLAY VSRESLVVGC GKLVWDPRAI ASHYARSLTG FWFDVIVILP VPQAVFWLVV    240
PKLIREEKVK LIMTILLLIF LFQFLPKIYH CICLMRRMQK VTGYIFGTIW WGFALNLIAY    300
FIASHVAGGC WYVLAIQRVA SCIRQQCMRT GNCNLSLACK EEVCYQFVSP TSTVGYPCLS    360
GNLTSVVNKP MCLDSNGPFR YGIYRWALPV ISSNSLAVKI LYPIFWGLMT LSTFANDLEP    420
TSNWLEVIFS IVMVLSGLLL FTLLIGNIQV FLHAVMAKKR KMQIRCRDME WWMKRRQLPS    480
RLRQRVRRFE RQRWNALGGE DELELIHDLP PGLRRDIKRY LCFDLINKVP LFRGMDDLIL    540
DNICDRAKPR VFSKDEKIIR EGDPVQRMIF IMRGRVKRIQ SLSKGVLATS TLEPGGYLGD    600
ELLSWCLRRP FLDRLPPSSA TFVCLENIEA FSLGSEDLRY ITDHFRYKFA NERLKRTARY    660
YSSNWRTWAA VNIQMAWRRR RKRTRGENIG GSMSPVSENS IEGNSERRLL QYAAMFMSIR    720
PHDHLE                                                              726

SEQ ID NO: 31            moltype = AA   length = 467
FEATURE                  Location/Qualifiers
source                   1..467
                         mol_type = protein
                         organism = Arabidopsis thaliana
SEQUENCE: 31
MILDLGFPCF VPPRTSSRED NKAWLLAETE PKLIDSEQHS LQSSFRFSLC SQLELEKIKK     60
EKPSLSYRNF PVSEGSETVL LVNLENETGE LTGEMNWSRG LSLEKSISPV ADSLIRFSYR    120
ELLTATRNFS KRRVLGRGAC SYVFKGRIGI WRKAVAIKRL DKKDKESPKS FCRELMIASS    180
LNSPNVVPLL GFCIDPDQGL FLVYKYVSGG SLERFLHDKK KKKSRKTPLN LPWSTRYKVA    240
LGIADAIAYL HNGTEQCVVH RDIKPSNILL SSNKIPKLCD FGLATWTAAP SVPFLCKTVK    300
GTFGYLAPEY FQHGKISDKT DVYAFGVVLL ELITGRKPIE ARRPSGEENL VVWAKPLLHR    360
GIEATEELLD PRLKCTRKNS ASMERMIRAA AACVINEESR RPGMKEILSI LKGGEGIELR    420
TLSSRKKSNL PGIMDCYPQL QRTKSEMKSH LTLAMLGVTE FEADDLL                 467

SEQ ID NO: 32            moltype = AA   length = 354
FEATURE                  Location/Qualifiers
source                   1..354
                         mol_type = protein
                         organism = Oryza sativa
SEQUENCE: 32
MAGSDEVNRN ECKTVVPLHT WVLISNFKLS YNILRRADGT FERDLGEYLD RRVPANARPL     60
EGVSSFDHII DQSVGLEVRI YRAAAEGDAE EGAAAVTRPI LEFLTDAPAA EPFPVIIFFH    120
GGSFVHSSAS STIYDSLCRR FVKLSKGVVV SVNYRRAPEH RYPCAYDDGW TALKWVMSQP    180
FMRSGGDAQA RVFLSGDSSG GNIAHHVAVR AADEGVKVCG NILLNAMFGG TERTESERRL    240
DGKYFVTLQD RDWYWKAYLP EDADRDHPAC NPFGPNGRRL GGLPFAKSLI IVSGLDLTCD    300
RQLAYADALR EDGHHVKVVQ CENATVGFYL LPNTVHYHEV MEEISDFLNA NLYY          354

SEQ ID NO: 33            moltype = AA   length = 390
FEATURE                  Location/Qualifiers
source                   1..390
                         mol_type = protein
                         organism = Zea mays
SEQUENCE: 33
MQSAAAIGLL RPCAARPLAA YTSPRRGAGA CSGGTQPIIT PRGIRLSARP GLVPASPLEE     60
KENRRCRASM HAAASAGEEA GGGLAKTLQL GALFGLWYLF NIYFNIYNKQ VLKVLPYPIN    120
ITTVQFAVGS AIALFMWITG IHKRPKISGA QLFAILPLAI VHTMGNLFTN MSLGKVAVSF    180
THTIKAMEPF FSVLLSAIFL GELPTPWVVL SLLPIVGGVA LASLTEASFN WAGFWSAMAS    240
NVTFQSRNVL SKKLMVKKEE SLDNINLFSI ITVMSFFLLA PVTLLTEGVK VSPAVLQSAG    300
LNLKQVYTRS LIAAFCFHAY QQVSYMILAR VSPVTHSVGN CVKRVVVIVT SVLFFRTPVS    360
PINSLGTGIA LAGVFLYSQL KRLKPKPKTA                                    390

SEQ ID NO: 34            moltype = AA   length = 477
FEATURE                  Location/Qualifiers
source                   1..477
                         mol_type = protein
                         organism = Arabidopsis thaliana
SEQUENCE: 34
MAHLLSASCP SVISLSSSSS KNSVKPFVSG QTFFNAQLLS RSSLKGLLFQ EKKPRKSCVF     60
RATAVPITQQ APPETSTNNS SSKPKRVMVI GGDGYCGWAT ALHLSKKNYE VCIVDNLVRR    120
LFDHQLGLES LTPIASIHDR ISRWKALTGK SIELYVGDIC DFEFLAESFK SFEPDSVVHF    180
GEQRSAPYSM IDRSRAVYTQ HNNVIGTLNV LFAIKEFGEE CHLVKLGTMG EYGTPNIDIE    240
EGYITITHNG RTDTLPYPKQ ASSFYHLSKV HDSHNIAFTC KAWGIRATDL NQGVVYGVKT    300
DETEMHEELR NRLDYDAVFG TALNRFCVQA AVGHPLTVYG KGGQTRGYLD IRDTVQCVEI    360
AIANPAKAGE FRVFNQFTEQ FSVNELASLV TKAGSKLGLD VKKMTVPNPR VEAEEHYYNA    420
```

```
KHTKLMELGL EPHYLSDSLL DSLLNFAVQF KDRVDTKQIM PSVSWKKIGV KTKSMTT        477

SEQ ID NO: 35             moltype = AA   length = 504
FEATURE                   Location/Qualifiers
source                    1..504
                          mol_type = protein
                          organism = Arabidopsis thaliana
SEQUENCE: 35
MVSLLSFFLL LLVPIFFLLI FTKKIKESKQ NLPPGPAKLP IIGNLHQLQG LLHKCLHDLS      60
KKHGPVMHLR LGFAPMVVIS SSEAAEEALK THDLECCSRP ITMASRVFSR NGKDIGFGVY     120
GDEWRELRKL SVREFFSVKK VQSFKYIREE ENDLMIKKLK ELASKQSPVD LSKILFGLTA     180
SIIFRTAFGQ SFFDNKHVDQ ESIKELMFES LSNMTFRFSD FFPTAGLKWF IGFVSGQHKR     240
LYNVFNRVDT FFNHIVDDHH SKKATQDRPD MVDAILDMID NEQQYASFKL TVDHLKGVLS     300
NIYHAGIDTS AITLIWAMAE LVRNPRVMKK AQDEIRTCIG IKQEGRIMEE DLDKLQYLKL     360
VVKETLRLHP AAPLLLPRET MADIKIQGYD IPQKRALLVN AWSIGRDPES WKNPEEFNPE     420
RFIDCPVDYK GHSFELLPFG SGRRICPGIA MAIATIELGL LNLLYFFDWN MPEKKKDMDM     480
EEAGDLTVDK KVPLELLPVI RISL                                            504

SEQ ID NO: 36             moltype = AA   length = 389
FEATURE                   Location/Qualifiers
source                    1..389
                          mol_type = protein
                          note = Pseudomonas syringae pv. tomato str. DC3000
                          organism = Pseudomonas syringae
SEQUENCE: 36
MVMTVLKMTD LDLQGKRVLI REDLNVPIKD GVVSSDARIL ASLPTIRLAL EKGAAVMVCS      60
HLGRPTEGEF SAENSLKPVA EYLSKALGRD VPLVADYLDG VDVKAGDIVL FENVRFNKGE     120
KKNADELAQK YAALCDVFVM DAFGTAHRAE GSTHGVAKYA KVAAAGPLLA AELEALGKAL     180
GAPAQPMAAI VAGSKVSTKL DVLNSLSAIC DQLIVGGGIA NTFLAAAGHK VGKSLYEPDL     240
LDTARAIAAK VSVPLPTDVV VAKEFAESAT ATVKLIADVA DDDMILDIGP QTAAHFAELL     300
KSSGTILWNG PVGVFEFDQF GEGTKTLAKA IAESKAFSIA GGGDTLAAID KYGVADQISY     360
ISTGGGAFLE FVEGKVLPAV EMLEQRARA                                       389

SEQ ID NO: 37             moltype = AA   length = 395
FEATURE                   Location/Qualifiers
source                    1..395
                          mol_type = protein
                          organism = Zea mays
SEQUENCE: 37
MSLIRGMGNV AKRWKELNGL NYWKGLVDPL DLDRRNIIN YGELSQATYT GLNRERRSRY       60
AGSCLFNRRD FLSRVDVSNP NLYEITKFIY AMCTVSLPDG FMVKSLSKAA WSRQSNWMGF     120
VAVATDEGKE LLGRRDVVVA WRGTIRMVEW VDDLDISLVP ASEIVLPGSA ANPCVHGGWL     180
SVYTSADPGS QYNKESARHQ VLNEVKRIQD LYKPEETSIT ITGHSLGAAL ATINATDIVS     240
NGYNRSCCPV SAFVFGSPRV GNPDFQKAFD SAADLRLLRV RNSPDVVPKW PKLGYSDVGT     300
ELMIDTGESP YLKAPGNPLT WHDMECYMHG VAGAQGSSGG FELLVDRDVA LVNKHEDALR     360
NEFAVPPSWW VVQNKGMVKG KDGRWHLADH EEDDD                                395

SEQ ID NO: 38             moltype = AA   length = 512
FEATURE                   Location/Qualifiers
source                    1..512
                          mol_type = protein
                          organism = Arabidopsis thaliana
SEQUENCE: 38
MATLLATPIF SPLASSPARN RLSCSKIRFG SKNGKILNSD GAQKLNLSKF RKPDGQRFLQ      60
MGSSKEMNFE RKLSVQAMDG AGTGNTSTIS RNVIAISHLL VSLGIILAAD YFLKQAFVAA     120
SIKFPSALFG MFCIFSVLMI FDSVVPAAAN GLMNFFEPAF LFIQRWLPLF YVPSLVVLPL     180
SVRDIPAASG VKICYIVAGG WLASLCVAGY TAIAVRKMVK TEMTEAEPMA KPSPFSTLEL     240
WSWSGIFVVS FVGALFYPNS LGTSARTSLP FLLSSTVLGY IVGSGLPSSI KKVFHPIICC     300
ALSAVLAALA FGYASGSGLD PVLGNYLTKV ASDPGAGDIL MGFLGSVILS FAFSMFKQRK     360
LVKRHAAEIF TSVIVSTVFS LYSTALVGRL VGLEPSLTVS ILPRCITVAL ALSIVSLFEG     420
TNSSLTAAVV VVTGLIGANF VQVVLDKLRL RDPIARGIAT ASSAHGLGTA ALSAKEPEAL     480
PFCAIAYALT GIFGSLLCSV PAVRQSLLAV VG                                   512

SEQ ID NO: 39             moltype = AA   length = 311
FEATURE                   Location/Qualifiers
source                    1..311
                          mol_type = protein
                          organism = Zea mays
SEQUENCE: 39
MARNEEKAQS MLNRFITMKQ EEKRKPRERR PYLASECRDL ADAERWRSEI LREIGAKVAE      60
IQNEGLGEHR LRDLNDEINK LLRERGHWER RIVELGGRDY SRSSNAPLMT DLDGNIVAVP     120
NPSGRGPGYR YFGAARKLPG VRELFDKPPE MRKRRTRYEI HKRINAGYYG YYDDEDGVLE     180
RLEGPAGKRM REEIVSEWHR VERVRREAMK GVMSGEVAAA GGRSGEAARE VLFEGVEEEV     240
EEERKREEEK REREKGEEVG REFVAHVPLP DKEIERMVL ERKKKELLSK YASDSLLVEQ      300
EEAKEMLNVR R                                                          311

SEQ ID NO: 40             moltype = AA   length = 682
FEATURE                   Location/Qualifiers
source                    1..682
```

```
                           mol_type = protein
                           organism = Zea mays
SEQUENCE: 40
MDLARRGGAA GADDEGEIER HEPAPEDMES DPAAAREKEL ELERVQSWRE QVTLRGVVAA    60
LLIGFMYSVI VMKIALTTGL VPTLNVSAAL MAFLALRGWT RVLERLGVAH RPFTRQENCV   120
IETCAVACYT IAFGGGFGST LLGLDKKTYE LAGASPANVP GSYKDPGFGW MAGFVAAISF   180
AGLLSLIPLR KVLVIDYKLT YPSGTATAVL INGFHTKQGD KNARMQVRGF LKYFGLSFVW   240
SFFQWFYTGG EVCGFVQFPT FGLKAWKQTF FFDFSLTYVG AGMICSHLVN ISTLLGAILS   300
WGILWPLISK QKGEWYPANI PESSMKSLYG YKAFLCIALI MGDGTYHFFK VFGVTVKSLH   360
QRLSRKRATN RVANGGDEMA ALDDLQRDEI FSDGSFPAWA AYAGYAALTV VSAVIIPHMF   420
RQVKWYYVIV AYVLAPLLGF ANSYGTGLTD INMAYNYGKI ALFIFAAWAG RDNGVIAGLA   480
GGTLVKQLVM ASADLMHDFK TGHLTMTSPR SLLVAQFIGT AMGCVVAPLT FLLFYNAFDI   540
GNPTGYWKAP YGLIYRNMAI LGVEGFSVLP RHCLALSAGF FAFAFVFSVA RDVLPRKYAR   600
FVPLPMAMAV PFLVGGSFAI DMCVGSLAVF VWEKVNRKEA VFMVPAVASG LICGDGIWTF   660
PSSILALAKI KPPICMKFTP GS                                            682

SEQ ID NO: 41              moltype = AA  length = 453
FEATURE                    Location/Qualifiers
source                     1..453
                           mol_type = protein
                           organism = Arabidopsis thaliana
SEQUENCE: 41
MAKVYWPYFD PEYENLSSRI NPPSVSIDNT SCKECTLVKV DSMNKPGILL EVVQVLTDLD    60
LTITKAYISS DGGWFMDVFH VTDQQGNKVT DSKTIDYIEK VLGPKGHASA SQNTWPGKRV   120
GVHSLGDHTS IEIIARDRPG LLSEVSAVLA DLNINVVAAE AWTHNRRIAC VLYVNDNATS   180
RAVDDPERLS SMEEQLNNVL RGCEEQDEKF ARTSLSIGST HVDRRLHQMF FADRDYEAVT   240
KLDDSASCGF EPKITVEHCE EKGYSVINVS CEDRPKLMFD IVCTLTDMQY IVFHATISSS   300
GSHASQEYFI RHKDGCTLDT EGEKERVVKC LEAAIHRRVS EGWSLELCAK DRVGLLSEVT   360
RILREHGLSV SRAGVTTVGE QAVNVFYVKD ASGNPVDVKT IEALRGEIGH SMMIDFKNKV   420
PSRKWKEEGQ AGTGGGWAKT SFFFGNLLEK LLP                                453

SEQ ID NO: 42              moltype = AA  length = 334
FEATURE                    Location/Qualifiers
source                     1..334
                           mol_type = protein
                           organism = Escherichia coli
SEQUENCE: 42
MAQVSRICNG VQNPSLISNL SKSSQRKSPL SVSLKTQQHP RAYPISSSWG LKKSGMTLIG    60
SELRPLKVMS SVSTACMMNP LIIKLGGVLL DSEEALERLF SALVNYRESH QRPLVIVHGG   120
GCVVVDELMKG LNLPVKKKNG LRVTPADQID IITGALAGTA NKTLLAWAKK HQIAAVGLFL   180
GDGDSVKVTQ LDEELGHVGL AQPGSPKLIN SLLENGYLPV VSSIGVTDEG QLMNVNADQA   240
ATALAATLGA DLILLSDVSG ILDGKGQRIA EMTAAKAEQL IEQGIITDGM IVKVNAALDA   300
ARTLGRPVDI ASWRHAEQLP ALFNGMPMGT RILA                               334

SEQ ID NO: 43              moltype = AA  length = 557
FEATURE                    Location/Qualifiers
source                     1..557
                           mol_type = protein
                           organism = Glycine max
SEQUENCE: 43
MALKTLSTFL SPLSLPNTKF PQFLTTKPSL ILCEFPRSQK SRLLAADSEG TGAAAPSPGE    60
KFLERQQSFE DAKIILKENK KKRKKKDNAI KASRAVASCY GCGAPLHTSD ADAPGYVDPE   120
TYELKKKHHQ LRTVLCRRCR LLSHGKMITA VGGHGGYPGG KLFVTAEELR EKLSHLRHEK   180
ALIVKLVDIV DFNGSFLSRV RDLAGSNPII LVVTKVDLLP RDTDLHCVGD WVVEATMRKK   240
LNVLSVHLTS SKSLVGITGV ISEIQKEKKG RDVYILGSAN VGKSAFINAL LKTMAINDPV   300
AASAQRYKPI QSAVPGTTLG PIQINAFLGG GKLYDTPGVH LYHRQTAVVH SEDLPILAPQ   360
SRLRGLSFPS SILSSVEEGA STIVNGLNAF SIFWGGLVRI DVLKVLPETC LTFYGPKRIP   420
IHMVPTEQAV EFYQTELGVL LTPPSGGENA ENWKGLESER KLQIKFEDVD SYDPKPACDI   480
AISGLGWFTV EPVSRSLKIS QPKPVETAGE LILAVHVPKA VEIFVRSPIP VGKAGAEWYQ   540
YVELTEKQEE MRPKWYF                                                  557

SEQ ID NO: 44              moltype = AA  length = 426
FEATURE                    Location/Qualifiers
source                     1..426
                           mol_type = protein
                           organism = Zea mays
SEQUENCE: 44
MAAALASSRY CWSRPSLPPQ PTRGRRSVTS CALSGREKRN SFSWRECAIS VALSVGLITG    60
APTFGPPAYA SSLEPVLPDV SVLISGPPIK DPGALLRYAL PIDNKAIREV QKPLEDITDS   120
LKVAGVRALD SVERNVRQAS KALNNGRSLI LAGLAEPKRA NGEELLNKLA VGFEELQRIV   180
EDRNRDAVAP KQKELLQYVG TVEEDMVDGF PFEIPEEYSN MPLLKGRATV DMKVKIKDNP   240
NMEDCVFRIV LDGYNAPVTA GNFVDLVKRK FYDGMEIQRA DGFVVQTGDP EGPAEGFIDP   300
STGKIRTVPL EIMVDGDKAP VYGETLEELG RYKAQTKLPF NAFGTMAMAR EEFDDNSASS   360
QVFWLLKESE LTPSNANILD GRYAVFGYVT ENEDYLADVK VGDVIESIQV VSGLDNLVNP   420
SYKIVG                                                              426

SEQ ID NO: 45              moltype = AA  length = 144
FEATURE                    Location/Qualifiers
source                     1..144
```

```
                        mol_type = protein
                        organism = Arabidopsis thaliana
SEQUENCE: 45
MMQELGLQRF SNDVVRLDLT PPSQTSSTSL SIDEEESTEA KIRRLISEHP VIIFSRSSCC   60
MCHVMKRLLA TIGVIPTVIE LDDHEVSSLP TALQDEYSGG VSVVGPPPAV FIGRECVGGL  120
ESLVALHLSG QLVPKLVQVG ALWV                                        144

SEQ ID NO: 46           moltype = AA  length = 509
FEATURE                 Location/Qualifiers
source                  1..509
                        mol_type = protein
                        organism = Escherichia coli
SEQUENCE: 46
MASSMLSSAT MVASPAQATM VAPFNGLKSS AAFPATRKAN NDITSITSNG GRVNCMQVWP   60
PIGKKKFETL SYLPDLTDSG GRVNCMQAMS NNEFHQRRLS ATPRGVGVMC NFFAQSAENA  120
TLKDVEGNEY IDFAAGIAVL NTGHRHPDLV AAVEQQLQQF THTAYQIVPY ESYVTLAEKI  180
NALAPVSGQA KTAFFTTGAE AVENAVKIAR AHTGRPVIA FSGGFHGRTY MTMALTGKVA   240
PYKIGFGPFP GSVYHVPYPS DLHGISTQDS LDAIERLFKS DIEAKQVAAI IFEPVQGEGG  300
FNVAPKELVA AIRRLCDEHG IVMIADEVQS GFARTGKLFA MDHYADKPDL MTMAKSLAGG  360
MPLSGVVGNA NIMDAPAPGG LGGTYAGNPL AVAAAHAVLN IIDKESLCER ANQLGQRLKN  420
TLIDAKESVP AIAAVRGLGS MIAVEFNDPQ TGEPSAAIAQ KIQQRALAQG LLLLTCGAYG  480
NVIRFLYPLT IPDAQFDAAM KILQDALSD                                   509

SEQ ID NO: 47           moltype = AA  length = 490
FEATURE                 Location/Qualifiers
source                  1..490
                        mol_type = protein
                        organism = Synechocystis sp.
SEQUENCE: 47
MASSMLSSAT MVASPAQATM VAPFNGLKSS AAFPATRKAN NDITSITSNG GRVNCMQVWP   60
PIGKKKFETL SYLPDLTDSG GRVNCMQAMT PELNPNFPEE TTSDAWLTPA DAGQDGDAQE  120
PAEDGGEEGV VSEELALPED LPPMDAMVAA VEEMTPVVVP ETVPETETPA LEDLVAQKTA  180
LEKDIAALQR EKAQWYGQQF QQLQREMARL VEEGTRELGQ RKAALEKEIE KLERRQERIQ  240
QEMRTTFAGA SQELAIRVQG FKDYLVGSLQ DLVSAADQLE LGVGDSWESS STHGDAIIEN  300
ADPTPVVSFA EQGFSSQKRQ IQALLEQYRT RPDYYGPPWQ LRRTFEPVHA ERIENWFFTL  360
GGRGAILSLD SRLQNILVGS AAIAILNQLY GDRCRALILA ATPERLGEWR RGLQDCLGIS  420
RSDFGPDRGI VLFESANALI QRAERLVGDR QMPLVLVDET EEQIDLALLQ FPLLLAFAPS  480
YQVGGSNYFS                                                         490

SEQ ID NO: 48           moltype = AA  length = 404
FEATURE                 Location/Qualifiers
source                  1..404
                        mol_type = protein
                        organism = Zea mays
SEQUENCE: 48
MAGELRHRRA PSEDEGVASS QRLDSAPAGN GKAGTSSGGG EGAEPRGGKR DALGWLEWCR   60
GWMAIVGEFL FQRIAASHLA NPLELPPLDG VSIVVTGATS GIGLEIARQL ALAGAHVVMA  120
VRRPKVAQEL IQKWQNENSE TGRPLNAEVM ELDLLSLDSV VKFADAWNAR MAPLHVLINN  180
AGIFAIGEPQ HFSKDGHEEH MQVNHLAPAL LAMLLIPSLL RGSPSRIVNV NSIMHSVGFV  240
DAEDFNLRKH KYRSWLAYSN SKLAQVKFSS MLHKRIPAEA GISIICASPG IVDTNVTRDL  300
PKIVVAAYRF LPYFIFDGQE GSRSALFAAC DPQVPEYCEM LKSEDWPVCA CINYDCNPMN  360
ASEEAHSLET SQLVWEKTLE MIGLPPDALD KLIAGETVPC RYGQ                  404

SEQ ID NO: 49           moltype = AA  length = 942
FEATURE                 Location/Qualifiers
source                  1..942
                        mol_type = protein
                        organism = Zea mays
SEQUENCE: 49
MEGDDFTPEG GKLPEFKLDA RQAQGFISFF KKLPQDPRAV RLFDRRDYYT AHGENATFIA   60
RTYYHTMSAL RQLGSTSDGI LSASVSKAMF ETIARNILLE RDCTLELYE GSGSNWRLTK   120
SGTPGNIGSF EDILFANNDM EDSPVIVALF PACRESQLYV GLSFLDMTNR KLGLAEFPED  180
SRFTNVESAL VALGCKECLL PADCEKSIDL NPLQDVISNC NVLLTEKKKA DFKSRDLAQD  240
LGRIIRGSVE PVRDLLSQFD YALGPLGALL SYAELLADDT NYGNYTIEKY NLNCYMRLDS  300
AAVRALNIAE GKTDVNKNFS LFGLMNRTCT VGMKRLLNR WLKQPLLDVN EINNRLDMVQ   360
AFVEDPELRQ GLRQQLKRIS DIDRLTHSLR KKSANLPVV KLYQSCSRIP YIKGILQQYN   420
GQFSTLIRSK FLEPLEEWMA KNRFGRFSSL VETAIDLAQL ENGEYRISPL YSSDLGVLKD  480
ELSVVENHIN NLHVDTASDL DLSVDKQLKL EKGSLGHVPR MSKKEEQKVR KKLTGSYLII  540
ETRKDGVKFT NSKLKNLSDQ YQALFGEYTS CQKKVVGDVV RVSGTFSEVF ENFAAVLSEL  600
DVLQSFADLA TSCPVPYVRP DITASEDGDI VLLGSRHPCL EAQDGVNFIP NDCTLVRGKS  660
WFQIITGPNM GGKSTFIRQV GVNVLMAQVG SFVPCDQASI SVRDCIFARV GAGDCQLHGV  720
STFMQEMLET ASILKGASDK SLIIIDELGR GTSTYDGFGL AWAICEHLME VTRAPTLFAT  780
HFHELTALAH RNDDEHQHIS DIGVANYHVG AHIDPLSRKL TMLYKVEPGA CDQSFGIHVA  840
EFANFPEAVV ALAKSKAEL EDFSTTPTFS DDLKDEVGSK RKRVFSPDDI TRGAARARLF   900
LEEFAALPMD EMDGSKILEM ATKMKADLQK DAADNPWLQQ FF                     942

SEQ ID NO: 50           moltype = AA  length = 344
FEATURE                 Location/Qualifiers
source                  1..344
```

```
                            mol_type = protein
                            organism = Arabidopsis thaliana
SEQUENCE: 50
MEWIRGETIG YGTFSTVSLA TRSNNDSGEF PPLMAVKSAD SYGAASLANE KSVLDNLGDD     60
CNEIVRCFGE DRTVENGEEM HNLFLEYASR GSLESYLKKL AGEGVPESTV RRHTGSVLRG    120
LRHIHANGFA HCDLKLGNIL LFGDGAVKIA DFGLAKRIGD LTALNYGVQI RGTPLYMAPE    180
SVNDNEYGSE GDVWALGCVV VEMFSGKTAW SLKEGSNFMS LLLRIGVGDE VPMIPEELSE    240
QGRDFLSKCF VKDPKKRWTA EMLLNHPFVT VDVDHDVLVK EEDFVVNMKT EDVSTSPRCP    300
FEFPDWVSVS SGSQTIDSPD ERVASLVTDM IPDWSVTNSW VTVR                    344

SEQ ID NO: 51               moltype = AA  length = 1187
FEATURE                     Location/Qualifiers
source                      1..1187
                            mol_type = protein
                            organism = Arabidopsis thaliana
SEQUENCE: 51
MRNHCLELSS NCSSIFASSK SNPRFSPSKL SYSTFFSRSA IYYRSKPKQA SSSSSFSTFP     60
PCLNRKSSLT HVLKPVSELA DTTTKPFSPE IVGKRTDLKK IMILGAGPIV IGQACEFDYS    120
GTQACKALRE EGYEVILINS NPATIMTDPE TANRTYIAPM TPELVEQVIE KERPDALLPT    180
MGGQTALNLA VALAESGALE KYGVELIGAK LGAIKKAEDR ELFKDAMKNI GLKTPPSGIG    240
TTLDECFDIA EKIGEFPLII RPAFTLGGTG GGIAYNKEEF ESICKSGLAA SATSQVLVEK    300
SLLGWKEYEL EVMRDLADNV VIICSIENID PMGVHTGDSI TVAPAQTLTD REYQRLRDYS    360
IAIIREIGVE CGGSNVQFAV NPVDGEVMII EMNPRVSRSS ALASKATGFP IAKMAAKLSV    420
GYTLDQIPND ITRKTPASFE PSIDYVVTKI PRFAFEKFPG SQPLLTTQMK SVGESMALGR    480
TFQESFQKAL RSLECGFSGW GCAKIKELDW DWDQLKYSLR VPNPDRIHAI YAAMKKGMKI    540
DEIYELSMVD KWFLTQLKEL VDVEQYLMSG TLSEITKEDL YEVKKRGFSD KQIAFATKTT    600
EEEVRTKRIS LGVVPSYKRV DTCAAEFEAH TPYMYSSYDV ECESAPNNKK KVLILGGGPN    660
RIGQGIEFDY CCCHTSFALQ DAGYETIMLN SNPETVSTDY DTSDRLYFEP LTIEDVLNVI    720
DLEKPDGIIV QFGGQTPLKL ALPIKHYLDK HMPMSLSGAG PVRIWGTSPD SIDAAEDRER    780
FNAILDELKI EQPKGGIAKS EADALAIAKE VGYPVVVRPS YVLGGRAMEI VYDDSRLITY    840
LENAVQVDPE RPVLVDKYLS DAIEIDVDTL TDSYGNVVIG GIMEHIEQAG VHSGDSACML    900
PTQTIPASCL QTIRTWTTKL AKKLNVCGLM NCQYAITTSG DVFLLEANPR ASRTVPFVSK    960
AIGHPLAKYA ALVMSGKSLK DLNFEKEVIP KHVSVKEAVF PFEKFQGCDV ILGPEMRSTG   1020
EVMSISSEFS SAFAMAQIAA GQKLPLSGTV FLSLNDMTKP HLEKIAVSFL ELGFKIVATS   1080
GTAHFLELKG IPVERVLKLH EGRPHAADMV ANGQIHLMLI TSSGDALDQK DGRQLRQMAL   1140
AYKVPVITTV AGALATAEGI KSLKSSAIKM TALQDFFEVK NVSSLLV                 1187

SEQ ID NO: 52               moltype = AA  length = 274
FEATURE                     Location/Qualifiers
source                      1..274
                            mol_type = protein
                            organism = Glycine max
SEQUENCE: 52
MRAKLFVFPI RGRNWCFSRT IDHSLSASHA SSQSPSTLKD LWTNINVGDK PLNTKTELFV     60
DYIANKMNNA WIGLEKAPEG SFKNKIHGLG LRLLSRVKPS EIFLKSISKE ITSVEIIYPS    120
SLNAQLVRRR LRHIAVRGAV IHRNYLYGLV SLIPLTSALS ILPLPNVPFF WVLFRTYSHW    180
RALQGSERLF QLVSDNSKTS NTCTYEKKTE HKESKSQRHS SNEPCWVLRP SKELENLVHL    240
EDGQESLSQH AIINICKIYD LNPVDVIKYE KSVF                               274

SEQ ID NO: 53               moltype = AA  length = 206
FEATURE                     Location/Qualifiers
source                      1..206
                            mol_type = protein
                            organism = Arabidopsis thaliana
SEQUENCE: 53
MAKESTTIDV GEPSTVTKSS SHVVKDAKKK GFVAVASRGG AKRGLAIFDF LLRLAAIAVT     60
IGAASVMYTA EETLPFFTQF LQFQAGYDDL PAFQYFVIAV AVVASYLVLS LPFSIVSIVR    120
PHAVAPRLIL LICDTLVVTL NTSAAAAAAS ITYLAHNGNQ STNWLPICQQ FGDFCQNVST    180
AVVADSIAIL FFIVLIIISA IALKRH                                        206

SEQ ID NO: 54               moltype = AA  length = 411
FEATURE                     Location/Qualifiers
source                      1..411
                            mol_type = protein
                            organism = Escherichia coli
SEQUENCE: 54
MATATSASLF STVSSSYSKA SSIPHSRLQS VKFNSVPSFT GLKSTSLISG SDSSSLAKTL     60
RGSVTKAQTS DKKPYGFKIN AMKTAYIAKQ RQISFVKSHF SRQLEERLGL IEVQAPILSR    120
VGDGTQDNLS GCEKAVQVKV KALPDAQFEV VHSLAKWKRQ TLGQHDFSAG EGLYTHMKAL    180
RPDEDRLSPL HSVYVDQWDW ERVMGDGERQ FSTLKSTVEA IWAGIKATEA AVSEEFGLAP    240
FLPDQIHFVH SQELLSRYPD LDAKGRERAI AKDLGAVFLV GIGGKLSDGH RHDVRAPDYD    300
DWSTPSELGH AGLNGDILVW NPVLEDAFEL SSMGIRVDAD TLKHQLALTG DEDRLELEWH    360
QALLRGEMPQ TIGGGIGQSR LTMLLLQLPH IGQVQCGVWP AAVRESVPSL L             411

SEQ ID NO: 55               moltype = DNA  length = 1173
FEATURE                     Location/Qualifiers
source                      1..1173
                            mol_type = unassigned DNA
                            organism = Zea mays
```

```
SEQUENCE: 55
atgcagagcg cggctgccat cgggctccta cggccatgtg ccgcgcggcc gctcgccgcc    60
tacactagcc cacgccgcgg cgccggcgcg tgcagcggcg gcacccagcc gctcatcacg   120
ccccgcggca tccgcctctc cgcccgcccc ggtctcgtgc cggcctcgcc gctggaggag   180
aaggagaacc ggagatgcag ggccagtatg cacgcggcgg cgtcggccgg agaggaagct   240
ggggagggc tcgccaagac gctgcagctg ggggcgcttt cgggctctg gtacctcttc    300
aacatctact tcaacatcta caacaagcag gttctgaagg ttttgccata ccctataaac   360
atcacaacgg tgcagtttgc tgttggaagt gccattgctt tgttcatgtg gatcactggt   420
atccataaaa ggccaaagat ttcgggtgcc cagcttttcg ctatccttcc tctagctatt   480
gtccatacca tgggcaatct ttttcacaaac atgagccttg gaaaggttgc agtgtcattt   540
acacatacta taaaggccat ggaacctttc ttctcagttc tcctttcagc aattttcctt   600
ggggagttgc ctacgccatg ggttgtgttg tctcttcttc cgattgttgg tggtgtagct   660
ttggcatccc ttactgaggc ctcctttaac tgggctggat tttggagtgc aatggcttca   720
aatgtaaccc tccagtcaag gaatgtgcta agcaagaaac ttatggtgaa gaaagaggaa   780
tctctcgaca acattaacct attctcgatc attacagtca tgtcattctt cctgttggcc   840
ccagtcaacct tacttacaga aggtgttaaa gttagtccag cagtgttgca gtctgctggt   900
ttgaacttga acaggtata cacaaggtca ttgattgctg cattctgctt ccatgcatac   960
caacaggtat catacatgat cctcgccagg gtatccccag tcacacattc agtgggcaat  1020
tgcgtcaagc gtgtggtggt cattgtgacc tctgttctgt tcttcaggac ccctgtttct  1080
cccatcaact ctcttggtac cgggatcgct cttgctggag ttttcctata ctcgcaattg  1140
aagagactta agcccaagcc caagactgct tga                               1173

SEQ ID NO: 56          moltype = DNA  length = 720
FEATURE                Location/Qualifiers
source                 1..720
                       mol_type = unassigned DNA
                       organism = Glycine max
SEQUENCE: 56
atggctgctg ctagtactat gatcacactc aagttctcat tcctctggag tctccttctc    60
tcagtttcac tcttgggtgt aaagtcatca catagccacc aaaatggtgg agaagaaca   120
attcctccaa catgcaagcg cattgagtgc cccacccatg atgtgattga agtgggtgat   180
ggctatgaaa tccgacgcta taataataat tcaactgtgt ggatgtcaac ttctcccatt   240
caagacattt ctctggttga agctacaaga actggcttca ggagtctatt tgattatatc   300
caaggcaaga acaactacaa gcaaaaaatt gagatgcaag cgcctgtgat cacagaagtt   360
tcacctagtg atggacccct tgtaaatcc tcatttgttg tcagcttctt tgtgccaaaa   420
ttgaaccaag caaaccctcc tcctgcaaag gtctccatg tccaaagatg aacaatatg    480
tatgtggcag caaggcagtt tggtggacac gtaaacgatt caaatgttgc ggtggaagcc   540
gctgtgttgc gagctagtat tgaaggcaca aatggtctg gtgccattga caaaaaccag    600
aaagctggcc atgcttctgt ttacactgtg gcacaataca atgacccttt tgaatatcag   660
aatagggtga atgagatatg gttcttgttt gaaatggaaa gtgaaaggca tgcaatttga   720

SEQ ID NO: 57          moltype = DNA  length = 981
FEATURE                Location/Qualifiers
source                 1..981
                       mol_type = unassigned DNA
                       organism = Glycine max
SEQUENCE: 57
atggaacgaa gtggcggaat ggtaacgggg tcgcatgaaa ggaacgaact tgttagagtt    60
agacacggtt ctgacagtgg gtctaaaccc ttgaagaatt taaatggtca gatttgtcaa   120
atatgtggta caccattgg attaacggct actggtgacc tctttgttgc ttgtcatgag    180
tgtggcttcc cactttgtca ttcttgttac gagtatgacc tgaaaaatgt gagccaatct   240
tgtcccagt gcaagactac attcacaagt cgccaagagg gtgctgaagt ggagggagat   300
gatgatgacg aagacgatgc tgatgatcta gataatggga tcaactatgg ccaaggaaac   360
aattccaagt cggggatgct gtgggaagaa gatgctgacc tctcttcatc ttctggacat   420
gattctcata taccaaaccc ccatctagta aacgggcaac cgatgtctgg tgagtttcca   480
tgtgctactt ctgatgctca atctatgcaa actacatcag atcctatggg tcaatccgaa   540
aaggttcact cacttccata tgctgatcca aagcaaccag gtcctgagag tgatgaagag   600
ataagaagag tgccggagat tggaggtgaa agcgctggaa cttcagcctc tcggccagat   660
gccggttcaa atgctggtac agaacgtgct caggggacag gggacagcca gaagaagaa   720
gggagaagcc cagctgataa agaaagcaag cggctactgag gaatagagtt               780
tcggctcagc aagcaaggga gaggaagaag gcatatttga ttgatttgga acaagagtc    840
aaagacttag agaagaagaa ctcagagctc aagaaagac tttccacttt gcagaatgaa    900
aaccaaatgc ttagacaaat attgaagaac acaacagcaa gcaggagagg gagcaatagt    960
ggtaccaata atgctgagta a                                             981

SEQ ID NO: 58          moltype = DNA  length = 792
FEATURE                Location/Qualifiers
source                 1..792
                       mol_type = unassigned DNA
                       organism = Zea mays
SEQUENCE: 58
atgttggagc tacgtctcgt gcagggctct ctcctgaaga aggttctcga atcgatcaag    60
gatctcgtca acgacgccaa cttcgactgc tccaccaccg gcttctccct ccaagccatg   120
gactccgaca acgtggcgct cgtctccctc ctgctcagca ccgaaggctg cgagcactac   180
cgctgcgacc gtaaccttc catggggat aatctcggaa acatgtcgaa gatgctcaaa   240
tgcgccggaa acgacgacat catcaccatc aaagccgatg acgcggcga caccgtcacc   300
ttcatgttcg agagtcccaa gcaagacaag attgcagatt tgagatgaa gctgatggat   360
atagacagtg agcatttggg gatacctgat gctgagtatc attcgattgt taggatgccg   420
tctaatgagt tctctagaat ctgcaaagat ctcagtacca tcggtgacac tgttgtgata   480
```

```
tctgtgacta aagaagggt taagttctct actgctggtg acattgggac agctaacatt  540
gtgttgagac agaacacaac tgttgacaag ccggaagatg cgattgtaat agagatgaac  600
gagccggtgt cactctcgtt tgccttgagg tatatgaatt ccttcacaaa ggcgactcct  660
ttgtcagaca cggtgacgat cagcttatcg tcggagctgc cagttgtggt ggagtataag  720
gtggctgaga tgggttacat tcgttactac ttggctccta agattgaaga agatgaagaa  780
gacaaggctt aa                                                      792
```

SEQ ID NO: 59          moltype = DNA  length = 902
FEATURE                Location/Qualifiers
source                 1..902
                       mol_type = unassigned DNA
                       organism = Zea mays
SEQUENCE: 59

```
atggcggcgc cgcgcgtcct cctcctcctc gccgccgcgg cccttctcgc cgtcgcctcc  60
ctcggggacg cttcgggcga gggccccgc gggcgcaagc tgctggtgct cgtcgacgat  120
ctggccgtcc gctcatccca ctcggccttc ttcggctcgc tccaggcccg cgggctagat  180
ctggagttcc gcctcgccga cgaccccaag ctctcgctcc accgctacgg tcagtacctc  240
tacgacggcc tcgtgctctt cgcccatcg accccggcct tcggccggatc ggtggaccag  300
aatgctgttc tggagtttat cgatgccggg catgatatga ttctggcagc agatcattcg  360
gcttcagatc tgatccgcgg catcgcgacg gagtgtgggg ttgactttga tgaggacccg  420
gaagcaatgg ttattgacca catcaattat gcctccagtg aggttgaagg tgaccacacc  480
ttgattgctg gcgatgacct gattcagtca gatgtgatat tgggtccaa aaagattgga  540
gctcctgtgc tgtttcgagg gattgggcat gcggccaatc catccaacag cttggttta  600
aaggttctat ctgcctcgcc atcagcgtat tcagcaaacc cggaggctaa gtggcatctg  660
ttccatctct cactgggtcg gccatatcgc tggttctgt tatgcaggct aggaataatg  720
ctcgtgtgtt gatatctgga tcactggatt tgtttagcaa caggttccta aagtcggtg  780
tgcagaaggc tggcagcaaa atgagccatg acaaagctgg aaatgaacaa tttgtgacag  840
agacgagcaa atgggtcttc catgagaggg ggcatctgaa ggcagggaat gtcaagcacc  900
at                                                                 902
```

SEQ ID NO: 60          moltype = DNA  length = 2184
FEATURE                Location/Qualifiers
source                 1..2184
                       mol_type = unassigned DNA
                       organism = Zea mays
SEQUENCE: 60

```
atggccgcgg ggtcgatccg ggtcaccatg gaggtgggcg ccgacggcgt cgcgctcatc  60
accatcgcca accgcccgt caacgcgctc caccccatca tcatcgcggg gctcaaggac  120
aagtacggcg aggccttgcg ccgtgacgac gttaaggcaa tcgtgctcac tggtgctgga  180
ggcaagttct gtgtgaggatt tgatatcaac gttttcacaa aggttcatca gactgggat  240
gtatcactta tgccggacgt atccgtcgag cttgtgtcaa acatgatgga agagggaaaa  300
aaaccttctg ttgcagccat tcaaggtctt gcattgggtg gtggcctaga gttgactatg  360
ggttgtcatg ctcggatatc tactcctgaa gctcaacttg gattgccaga gctaaccctt  420
ggcatcatcc ctggatttgg aggtacccag cgtttgccga ggcttgtagg tctacccaaa  480
gcaattgaaa tgatgctgca aagtaagttc attacggcaa aggaagggaa tgaacgtggt  540
ttgattgatg ccctttgctc tcctgatgaa ttgataaaga catcacgtct ttgggctctg  600
gaaattgcta attgccgtaa accttggatg aggtctcttg cagaacaga taggcttgaa  660
ccactctctg aagctcgtgc tgtgttaaat gcagcaagac agcaagcaat gaagatcgca  720
ccaaacatgc cacaaaacca ggcctgcctg atgtgatgg aggaaggcat attatgtgga  780
ggccaagctg gtgttttgaa ggaggccgtg gttttcaagg agctggtgat agcaccaaca  840
tcaaaggccg ttgtccatgt tttctttgca caacgttcca cgacaaaggt gccaggtgta  900
actgatgttc aactgaaacc aaggccaatt agaaaagttg ctgttattgg tggtggtctg  960
atgggatctg gaattgccac atcacttctt gttagcaaca tttctgttgt gctcaaggaa  1020
gtaaaccctc agtttctgca aagggagag aaaacaatag caggtaatct tgagggcctg  1080
gtcaaaagag gttcactaac aaaggatagg atgcacaagg ccatggccct tctcaagggt  1140
gctttggatt attcagattt caaggatgtt gatatggtta ttgaggctgt tattgagaag  1200
attcctttga agcaatcaat atttgctgac attgagaaa tctgtccaaa acattgcata  1260
cttgcaacaa acacatccac cattgatttg aatgttgttg caagaagac aaattctcaa  1320
gatagaatta tagggggctca cttttttcagc cctgctcata ttatgccctt gcttgaaatt  1380
gttcggacgg agaagacatc accacaaagct atccttgatc tcatcaccat tgggaagata  1440
ataaagaaag tccctattgt ggtcggcaac tgcacaggat ttgcagtcaa ccgtacattt  1500
tttccttaca cacagggttc tcatcttcta gttagtcttg gtattgatgt tttcagaatt  1560
gatcgagtaa taagcacctt tggcatgcca atgggaccttt tcaactcca agatgtggct  1620
gggtatggag ttgccttggc agtaaaggat atctacgctg atgccttttgg agaaagaaat  1680
ttggactctg acctttgtgga tttgatggta aaggatggac gacaaggaaa ggtgaacggc  1740
aaaggttact acatttatga gaagggtggg aagccaaagc cagatcctag tgttaagcat  1800
gttatcgagg agtaccgaaa gcacgcaaac acaatgcctg tgaaagcc tgttacttta  1860
acggatcaag atattttgga gatgattttc ttcccagttg tgatgaggc atgcagggtt  1920
atggatgaaa atgttgtaat tcgagcttct gatcttgata ttgcttctgt tcttggaatg  1980
ggctttccta aatacagggg tggtcttgtc ttctgggctg acactgttgg agcaccttac  2040
atacattcta agctaagcaa gtgggctgaa atttatggcc ccttcttcaa accatcatca  2100
tatttggaac agcgagctaa gagtggtgta ccattgagcg caccaggagc ttcgcagcaa  2160
ggttcggcga ggtcacgcat gtga                                          2184
```

SEQ ID NO: 61          moltype = AA  length = 390
FEATURE                Location/Qualifiers
source                 1..390
                       mol_type = protein
                       organism = Zea mays

```
SEQUENCE: 61
MQSAAAIGLL RPCAARPLAA YTSPRRGAGA CSGGTQPLIT PRGIRLSARP GLVPASPLEE    60
KENRRCRASM HAAASAGEEA GGGLAKTLQL GALFGLWYLF NIYFNIYNKQ VLKVLPYPIN   120
ITTVQFAVGS AIALFMWITG IHKRPKISGA QLFAILPLAI VHTMGNLFTN MSLGKVAVSF   180
THTIKAMEPF FSVLLSAIFL GELPTPWVVL SLLPIVGGVA LASLTEASFN WAGFWSAMAS   240
NVTFQSRNVL SKKLMVKKEE SLDNINLFSI ITVMSFFLLA PVTLLTEGVK VSPAVLQSAG   300
LNLKQVYTRS LIAAFCFHAY QQVSYMILAR VSPVTHSVGN CVKRVVVIVT SVLFFRTPVS   360
PINSLGTGIA LAGVFLYSQL KRLKPKPKTA                                   390

SEQ ID NO: 62            moltype = AA   length = 239
FEATURE                  Location/Qualifiers
source                   1..239
                         mol_type = protein
                         organism = Glycine max
SEQUENCE: 62
MAAASTMITL KFSFLWSLLL SVSLLGVKSS HSHQNGGRRT IPPTCKRIEC PTHDVIEVGD    60
GYEIRRYNNN STVWMSTSPI QDISLVEATR TGFRSLFDYI QGKNNYKQKI EMTAPVITEV   120
SPSDGPFCKS SFVVSFFVPK LNQANPPPAK GLHVQRWNNM YVAARQFGGH VNDSNVAVEA   180
AVLRASIEGT KWSGAIDKNQ KAGHASVYTV AQYNDPFEYQ NRVNEIWFLF EMESERHAI    239

SEQ ID NO: 63            moltype = AA   length = 326
FEATURE                  Location/Qualifiers
source                   1..326
                         mol_type = protein
                         organism = Glycine max
SEQUENCE: 63
MERSGGMVTG SHERNELVRV RHGSDSGSKP LKNLNGQICQ ICGDTIGLTA TGDLFVACHE    60
CGFPLCHSCY EYELKNVSQS CPQCKTTFTS RQEGAEVEGD DDDEDDADDL DNGINYGQGN   120
NSKSGMLWEE DADLSSSSGH DSHIPNPHLV NGQPMSGEFP CATSDAQSMQ TTSDPMGQSE   180
KVHSLPYADP KQPGPESDEE IRRVPEIGGE SAGTSASRPD AGSNAGTERA QGTGDSQKKR   240
GRSPADKESK RLKRLLRNRV SAQQARERKK AYLIDLETRV KDLEKKNSEL KERLSTLQNE   300
NQMLRQILKN TTASRRGSNS GTNNAE                                       326

SEQ ID NO: 64            moltype = AA   length = 263
FEATURE                  Location/Qualifiers
source                   1..263
                         mol_type = protein
                         organism = Zea mays
SEQUENCE: 64
MLELRLVQGS LLKKVLESIK DLVNDANFDC STTGFSLQAM DSSHVALVSL LLRSEGFEHY    60
RCDRNLSMGM NLGNMSKMLK CAGNDDIITI KADDGGDTVT PMFESPKQDK IADFEMKLMD   120
IDSEHLGIPD AEYHSIVRMP SNEFSRICKD LSTIGDTVVI SVTKEGVKFS TAGDIGTANI   180
VLRQNTTVDK PEDAIVIEMN EPVSLSFALR YMNSFTKATP LSDTVTISLS SELPVVVEYK   240
VAEMGYIRYY LAPKIEEDEE DKA                                          263

SEQ ID NO: 65            moltype = AA   length = 243
FEATURE                  Location/Qualifiers
source                   1..243
                         mol_type = protein
                         organism = Zea mays
SEQUENCE: 65
MAAPRVLLLL AAAALLAVAS LGDASGEGPR GRKLLVLVDD LAVRSSHSAF FGSLQARGLD    60
LEFRLADDPK LSLHRYGQYL YDGLVLFAPS TPRFGGSVDQ NAVLEFIDAG HDMILAADHS   120
ASDLIRGIAT ECGVDFDEDP EAMVIDHINY ASSEVEGDHT LIAGDDLIQS DVILGSKKIE   180
APVLFRGIGH AANPSNSLVL KVLSASPSAY SANPEAKWHL FHLSLGRPYR WFLLCRLGIM   240
LVC                                                                243

SEQ ID NO: 66            moltype = AA   length = 727
FEATURE                  Location/Qualifiers
source                   1..727
                         mol_type = protein
                         organism = Zea mays
SEQUENCE: 66
MAAGSIRVTM EVGADGVALI TIANPPVNAL HPIIIAGLKD KYAEALRRDD VKAIVLTGAG    60
GKFCGGFDIN VFTKVHQTGD VSLMPDVSVE LVSNMMEEGK KPSVAAIQGL ALGGGGLELTM   120
GCHARISTPE AQLGLPELTL GIIPGFGGTQ RLPRLVGLPK AIEMMLQSKF ITAKEGNERG   180
LIDALCSPDE LIKTSRLWAL EIANCRKPWM RSLGRTDRLG PLSEARAVLN AARQQAMKIA   240
PNMPQNQACL DVMEEGILCG GQAGVLKEAV VFKELVIAPT SKALVHVFFA QRSTTKVPGV   300
TDVQLKPRPI RKVAVIGGGL MGSGIATSLL VSNISVVLKE VNPQFLQRGE KTIAGNLEGL   360
VKRGSLTKDR MHKAMALLKG ALDYSDFKDV DMVIEAVIEK IPLKQSIFAD IEKICPKHCI   420
LATNTSTIDL NVVGKKTNSQ DRIIGAHFFS PAHIMPLLEI VRTEKTSPQA ILDLITIGKI   480
IKKVPIVVGN CTGFAVNRTF FPYTQGSHLL VSLGIDVFRI DRVISTFGMP MGPFQLQDVA   540
GYGVALAVKD IYADAFGERN LDSDLVDLMV KDGRQGKVNG KGYYIYEKGG KPKPDPSVKH   600
VIEEYRKHAN TMPGGKPVTL TDQDILEMIF FPVVNEACRV MDENVVIRAS DLDIASVLGM   660
GFPKYRGGLV FWADTVGAPY IHSKLSKWAE IYGPFFKPSS YLEQRAKSGV PLSAPGASQQ   720
GSARSRM                                                            727

SEQ ID NO: 67            moltype = DNA   length = 328
FEATURE                  Location/Qualifiers
```

```
source                  1..328
                        mol_type = other DNA
                        note = Engineered miRNA precursor
                        organism = synthetic construct
SEQUENCE: 67
ggcagagccg tgcccgtctc atccctgcc  cgtgcaagca gctaggtagg acgatttgag    60
cgtggtgtta ggccgaaccg ctgaaggaag attgctccac tgttgactgc attagatgtt   120
gaagaggtac caaaaatgta ttgcttatat tcagcaatat aatgttcttg gtacctaggc   180
aacatctaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggttag                                     328

SEQ ID NO: 68           moltype = DNA  length = 328
FEATURE                 Location/Qualifiers
source                  1..328
                        mol_type = other DNA
                        note = Engineered miRNA precursor
                        organism = synthetic construct
SEQUENCE: 68
ggcagagccg tgcccgtctc atccctgcc  cgtgcaagca gctaggtagg acgatttgag    60
cgtggtgtta ggccgaaccg ctgaaggaag attgctccac tgttgactgc atttcatagc   120
catcacccac ttcaaaatgta ttgcttatat tcagcaatat aatgttcgaa gtgggttcgg   180
gctatgaaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggttag                                     328

SEQ ID NO: 69           moltype = DNA  length = 325
FEATURE                 Location/Qualifiers
source                  1..325
                        mol_type = other DNA
                        note = Engineered miRNA precursor
                        organism = synthetic construct
SEQUENCE: 69
ggcagagccg tgcccgtctc atccctgcc  cgtgcaagca gctaggtagg acgatttgag    60
cgtggtgtta ggccgaaccg ctgaaggaag attgctccac tgttgactgc attgacaagc   120
aacaaagagg tcaaaatgta ttgcttatat tcagcaatat aatgttctga cctcttgtgt   180
gcttgtcaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggt                                        325

SEQ ID NO: 70           moltype = DNA  length = 325
FEATURE                 Location/Qualifiers
source                  1..325
                        mol_type = other DNA
                        note = Engineered miRNA precursor
                        organism = synthetic construct
SEQUENCE: 70
ggcagagccg tgcccgtctc atccctgcc  cgtgcaagca gctaggtagg acgatttgag    60
cgtggtgtta ggccgaaccg ctgaaggaag attgctccac tgttgactgc atttatactc   120
caccacaact ggcaaatgta ttgcttatat tcagcaatat aatgttcgcc agttgtttgg   180
gagtataaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggt                                        325

SEQ ID NO: 71           moltype = DNA  length = 408
FEATURE                 Location/Qualifiers
source                  1..408
                        mol_type = other DNA
                        note = Engineered miRNA precursor
                        organism = synthetic construct
SEQUENCE: 71
ggcagagccg tgcccgtctc atccctgcc  cgtgcaagca gctaggtagg acgatttgag    60
cgtggtgtta ggccgaaccg ctgaaggaag attgctccac tgttgactgc attgagagat   120
ggaacagatg cccaaatgta ttgcttatat tcagcaatat aatgttcggg catctgggac   180
atctctcaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggtttcag tttacctaat ttatggtctg tacccatgaa   360
aagtgggaaa aggctgaaga attcgatttc tttctttctt tcaatgtt              408

SEQ ID NO: 72           moltype = DNA  length = 408
FEATURE                 Location/Qualifiers
source                  1..408
                        mol_type = other DNA
                        note = Engineered miRNA precursor
                        organism = synthetic construct
SEQUENCE: 72
ggcagagccg tgcccgtctc atccctgcc  cgtgcaagca gctaggtagg acgatttgag    60
cgtggtgtta ggccgaaccg ctgaaggaag attgctccac tgttgactgc attagaagat   120
gagaaccctg tgcaaatgta ttgcttatat tcagcaatat aatgttcgca cagggtgagc   180
```

```
atcttctaat atagtcgata gtggaagaac ggtaacatat gtggtttgca gcaggtgagc    240
aggatgggtg tggatgattg aatatctctg ttcagtgttt tcatcatctg actgaacact    300
gaatcagctt gctgacgtta gaggtttcag tttacctaat ttatggtctg tacccatgaa    360
aagtgggaaa aggctgaaga attcgatttc tttctttctt tcaatgtt                 408

SEQ ID NO: 73           moltype = DNA   length = 21
FEATURE                 Location/Qualifiers
source                  1..21
                        mol_type = other DNA
                        note = miRNA recognition site
                        organism = synthetic construct
SEQUENCE: 73
tagatgttga agaggtacca a                                               21

SEQ ID NO: 74           moltype = DNA   length = 21
FEATURE                 Location/Qualifiers
source                  1..21
                        mol_type = other DNA
                        note = miRNA recognition site
                        organism = synthetic construct
SEQUENCE: 74
ttcatagcca tcacccactt c                                               21

SEQ ID NO: 75           moltype = DNA   length = 21
FEATURE                 Location/Qualifiers
source                  1..21
                        mol_type = other DNA
                        note = miRNA recognition site
                        organism = synthetic construct
SEQUENCE: 75
tgacaagcaa caaagaggtc a                                               21

SEQ ID NO: 76           moltype = DNA   length = 21
FEATURE                 Location/Qualifiers
source                  1..21
                        mol_type = other DNA
                        note = miRNA recognition site
                        organism = synthetic construct
SEQUENCE: 76
ttatactcca ccacaactgg c                                               21

SEQ ID NO: 77           moltype = DNA   length = 21
FEATURE                 Location/Qualifiers
source                  1..21
                        mol_type = other DNA
                        note = miRNA recognition site
                        organism = synthetic construct
SEQUENCE: 77
tgagagatgg aacagatgcc c                                               21

SEQ ID NO: 78           moltype = DNA   length = 21
FEATURE                 Location/Qualifiers
source                  1..21
                        mol_type = other DNA
                        note = miRNA recognition site
                        organism = synthetic construct
SEQUENCE: 78
tagaagatga gaaccctgtg c                                               21

SEQ ID NO: 79           moltype = AA    length = 315
FEATURE                 Location/Qualifiers
source                  1..315
                        mol_type = protein
                        organism = Arabidopsis thaliana
SEQUENCE: 79
MVGWAIALHG GAGDIPIDLP DERRIPRESA LRHCLDLGIS ALKSGKPPLD VAELVVRELE     60
NHPDFNAGKG SVLTAQGTVE MEASIMDGKT KRCGAVSGLT TVVNPISLAR LVMEKTPHIY    120
LAFDAAEAFA RAHGVETVYS SHFITPENIA RLKQAKEFNR VQLDYTVPSP KVPDNCGDSQ    180
IGTVGCVAVD SAGNLASATS TGGYVNKMVG RIGDTPVIGA GTYANHLCAI SATGKGEDII    240
RGTVARDVAA LMEYKGLSLT EAAAYVVDQS VPRGSCGLVA VSANGEVTMP FNTTGMFRAC    300
ASEDGYSEIA IWPNN                                                     315

SEQ ID NO: 80           moltype = AA    length = 726
FEATURE                 Location/Qualifiers
source                  1..726
                        mol_type = protein
                        organism = Arabidopsis thaliana
SEQUENCE: 80
MPSHPNFIFR WIGLFSDKFR RQTTGIDENS NLQINGGDSS SSGSDETPVL SSIECYACTQ     60
```

```
VGVPAFHSTS  CDQAHAPEWR  ASAGSSLVPI  QEGSVPNPAR  TRFRRLKGPF  GEVLDPRSKR   120
VQRWNRALLL  ARGMALAVDP  LFFYALSIGR  TTGPACLYMD  GAFAAVVTVL  RTCLDAVHLW   180
HVWLQFRLAY  VSRESLVVGC  GKLVWDPRAI  ASHYARSLTG  FWFDVIVILP  VPQAVFWLVV   240
PKLIREEKVK  LIMTILLLIF  LFQFLPKIYH  CICLMRRMQK  VTGYIFGTIW  WGFALNLIAY   300
FIASHVAGGC  WYVLAIQRVA  SCIRQQCMRT  GNCNLSLACK  EEVCYQFVSP  TSTVGYPCLS   360
GNLTSVVNKP  MCLDSNGPFR  YGIYRWALPV  ISSNSLAVKI  LYPIFWGLMT  LSTFANDLEP   420
TSNWLEVIFS  IVMVLSGLLL  FTLLIGNIQV  FLHAVMAKKR  KMQIRCRDME  WWMKRRQLPS   480
RLRQRVRRFE  RQRWNALGGE  DELELIHDLP  PGLRRDIKRY  LCFDLINKVP  LFRGMDDLIL   540
DNICDRAKPR  VFSKDEKIIR  EGDPVQRMIF  IMRGRVKRIQ  SLSKGVLATS  TLEPGGYLGD   600
ELLSWCLRRP  FLDRLPPSSA  TFVCLENIEA  FSLGSEDLRY  ITDHFRYKFA  NERLKRTARY   660
YSSNWRTWAA  VNIQMAWRRR  RKRTRGENIG  GSMSPVSENS  IEGNSERRLL  QYAAMFMSIR   720
PHDHLE                                                                  726

SEQ ID NO: 81           moltype = AA  length = 365
FEATURE                 Location/Qualifiers
source                  1..365
                        mol_type = protein
                        note = Oryza sativa Japonica Group
                        organism = Oryza sativa
SEQUENCE: 81
AGSDEVNRNE  CKTVVPLHTW  VLISNFKLSY  NILRRADGTF  ERDLGEYLDR  RVPANARPLE    60
GVSSFDHIID  QSVGLEVRIY  RAAAEGDAEE  GAAAVTRPIL  EFLTDAPAAE  PFPVIIFFHG   120
GSFVHSSASS  TIYDSLCRRF  VKLSKGVVVS  VNYRRAPEHR  YPCAYDDGWT  ALKWVMSQPF   180
MRSGGDAQAR  VFLSGDSSGG  NIAHHVAVRA  ADEGVKVCGN  ILLNAMFGGT  ERTESERRLD   240
GKYFVTLQDR  DWYKAYLPE   DADRDHPACN  PFGPNGRRLG  GLPFAKSLII  VSGLDLTCDR   300
QLAYADALRE  DGHHVKVVQC  ENATVGFYLL  PNTVHYHEVM  EEISDFLNAN  LYYGSHHHHH   360
HHHHH                                                                   365

SEQ ID NO: 82           moltype = AA  length = 390
FEATURE                 Location/Qualifiers
source                  1..390
                        mol_type = protein
                        organism = Zea mays
SEQUENCE: 82
MQSAAAIGLL  RPCAARPLAA  YTSPRRGAGA  CSGGTQPIIT  PRGIRLSARP  GLVPASPLEE    60
KENRRCRASM  HTAASAGEEA  GGGLAKTLQL  GALFGLWYLF  NIYFNIYNKQ  VLKVLPYPIN   120
ITTVQFAVGS  AIALFMWITG  IHKRPKISGA  QLFAILPLAI  VHTMGNLFTN  MSLGKVAVSF   180
THTIKAMEPF  FSVLLSAIFL  GELPTPWVVL  SLLPIVGGVA  LASLTEASFN  WAGFWSAMAS   240
NVTFQSRNVL  SKKLMVKKEE  SLDNINLFSI  ITVMSFFLLA  PVTLLTEGVK  VSPAVLQSAG   300
LNLKQVYTRS  LIAACCFHAY  QQVSYMILAR  VSPVTHSVGN  CVKRVVVIVT  SVLFFRTPVS   360
PINSLGTGIA  LAGVFLYSQL  KRLKPKPKTA                                      390

SEQ ID NO: 83           moltype = AA  length = 504
FEATURE                 Location/Qualifiers
source                  1..504
                        mol_type = protein
                        organism = Arabidopsis thaliana
SEQUENCE: 83
MVSLLSFFLL  LLVPIFFLLI  FTKKIKESKQ  NLPPGPAKLP  IIGNLHQLQG  LLHKCLHDLS    60
KKHGPVMHLR  LGFAPMVVIS  SSEAAEEALK  THDLECCSRP  ITMASRVFSR  NGKDIGFGVY   120
GDEWRELRKL  SVREFFSVKK  VQSFKYIREE  ENDLMIKKLK  ELASKQSPVD  LSKILFGLTA   180
SIIFRTAFGQ  SFFDNKHVDQ  ESIKELMFES  LSNMTFRFSD  FFPTAGLKWF  IGFVSGQHKR   240
LYNVFNRVDT  FFNHIVDDHH  SKKATQDRPD  MVDAILDMID  NEQQYASFKL  TVDHLKGVLS   300
NIYHAGIDTS  AITLIWAMAE  LVRNPRVMKK  AQDEIRTCIG  IKQEGRIMEE  DLDKLQYLKL   360
VVKETLRLHP  AAPLLLPRET  MADIKIQGYD  IPQKRALLVN  AWSIGRDPES  WKNPEEFNPE   420
RFIDCPVDYK  GHSCELLPFG  SGRRICPGIA  MAIATIELGL  LNLLYFFDWN  MPEKKKDMDM   480
EEAGDLTVDK  KVPLELLPVI  RISL                                            504

SEQ ID NO: 84           moltype = AA  length = 387
FEATURE                 Location/Qualifiers
source                  1..387
                        mol_type = protein
                        note = Pseudomonas syringae pv. tomato str. DC3000
                        organism = Pseudomonas syringae
SEQUENCE: 84
MTVLKMTDLD  LQGKRVLIRE  DLNVPIKDGV  VSSDARILAS  LPTIRLALEK  GAAVMVCSHL    60
GRPTEGEFSA  ENSLKPVAEY  LSKALGRDVP  LVADYLDGVD  VKAGDIVLFE  NVRFNKGEKK   120
NADELAQKYA  ALCDVPVMDA  FGTAHRAEGS  THGVAKYAKV  AAAGPLLAAE  LEALGKALGA   180
PAQPMAAIVA  GSKVSTKLDV  LNSLSAICDQ  LIVGGGIANT  FLAAAGHKVG  KSLYEPDLLD   240
TARAIAAKVS  VPLPTDVVVA  KEFAESATAT  VKLIADVADD  DMILDIGPQT  AAHFAELLKS   300
SGTILWNGPV  GVFEFDQFGE  GTKTLAKAIA  ESKAFSIAGG  GDTLAAIDKY  GVADQISYIS   360
TGGGAFLEFV  EGKVLPAVEM  LEQRARA                                         387

SEQ ID NO: 85           moltype = AA  length = 387
FEATURE                 Location/Qualifiers
source                  1..387
                        mol_type = protein
                        note = Pseudomonas syringae pv. phaseolicola 1448A
                        organism = Pseudomonas syringae
```

```
SEQUENCE: 85
MTVLKMTDLD LQGKRVLIRE DLNVPVKDGV VSSDARILAS LPTIRLALEK GAAVMVCSHL    60
GRPTEGEFSA ENSLKPVADY LSKALGRDVP LVADYLDGVD VKAGDVVLFE NVRFNKGEKK   120
NADELAQKYA ALCDVFVMDA FGTAHRAEGS THGVAKFAKV AAAGPLLAAE LEALGKALGA   180
PAQPMTAIVA GSKVSTKLDV LNSLSGICNQ LIVGGGIANT FLAAAGHKVG KSLYEPDLLD   240
TARAIAAKVS VPLPTDVVVA KEFAESATAT VKLIADVADD DMILDIGPQT AAHFAELLKS   300
SGTILWNGPV GVFEFDQFGE GTKTLAKAIG ESQAFSIAGG GDTLAAIDKY GVAEQISYIS   360
TGGGAFLEFV EGKVLPAVEV LEQRAKA                                      387

SEQ ID NO: 86         moltype = AA   length = 387
FEATURE               Location/Qualifiers
source                1..387
                      mol_type = protein
                      note = Pseudomonas syringae pv. syringae B728a
                      organism = Pseudomonas syringae
SEQUENCE: 86
MTVLKMTDLD LQGKRVLIRE DLNVPVKDGV VSSDARILAS LPTIRLALEK GAAVMVCSHL    60
GRPTEGEFSA ENSLKPVADY LSKALGRDVP LVADYLDGVD VKAGEVVLFE NVRFNKGEKK   120
NADELAQQYA ALCDVFVMDA FGTAHRAEGS THGVAKFAKV AAAGPLLAAE LEALGKALGA   180
PAQPMTAIVA GSKVSTKLDV LNSLSGICNQ LIVGGGIANT FLAAAGHKVG KSLYEPDLLD   240
TARAIAAKVS VPLPTDVVVA KEFAESAAAT VKLIADVADD DMILDIGPQT AAHFAELLKS   300
SGTILWNGPV GVFEFDQFGE GTKTLAKAIA ESQAFSIAGG GDTLAAIDKY GVAQQISYIS   360
TGGGAFLEFV EGKVLPAVEV LEQRAKA                                      387

SEQ ID NO: 87         moltype = AA   length = 393
FEATURE               Location/Qualifiers
source                1..393
                      mol_type = protein
                      organism = Sorghum bicolor
SEQUENCE: 87
MSLIRGMGNI AKRWKELNGL NYWKGLVDPL DLDRRNIIN YGELSQAAYT GLNRERRSRY     60
AGSCLFNRRD FLSRVDVSNP NLYEITKFIY AMCTVSLPDG FMVKSLSKAA WSRQSNWMGF   120
VAVATDEGKE VLGRRDVVVA WRGTIRMVEW MDDLDISLVP ASEIVLPGSA TNPCVHGGWL   180
SVYTSADPGS QYNKESARHQ VLNEVKRIQD LYKTEETSIS ITGHSLGAAL ATINAIDIVS   240
NGYNRSCPVS AFVFGSPRVG NPDFQEAFDS AADLRLLRVR NSPDVVPKWP KLGYSDVGTE   300
LRIDTGESPY LKSPGNPLTW HDMECYMHGV AGAQGSSGGF ELAVDRDIAL VNKHEDALKN   360
EFAVPSSWWV VQNKDMVKGK DGRWHLADHE DDD                                393

SEQ ID NO: 88         moltype = AA   length = 512
FEATURE               Location/Qualifiers
source                1..512
                      mol_type = protein
                      organism = Arabidopsis thaliana
SEQUENCE: 88
MATLLATPIF SPLASSPARN RLSCSNIRFG SKNGKILNSD GAQKLNLSKF RKPDGQRFLQ    60
MGSSKEMNFE RKLSVQAMDG AGTGNTSTIS RNVIAISHLL VSLGIILAAD YFLKQAFVAA   120
SIKFPSALFG MFCIFSVLMI FDSVVPAAAN GLMNFFEPAF LFIQRWLPLF YVPSLVVLPL   180
SVRDIPAASG VKICYIVAGG WLASLCVAGY TAIAVRKMVK TEMTEAEPMA KPSPFSTLEL   240
WSWSGIFVVS FVGALFYPNS LGTSARTSLP FLLSSTVLGY IVGSGLPSSI KKVFHPIICC   300
ALSAVLAALA FGYASGSGLD PVLGNYLTKV ASDPGAGDIL MGFLGSVILS FAFSMFKQRK   360
LVKRHAAEIF TSVIVSTVFS LYSTALVGRL VGLEPSLTVS ILPRCITVAL ALSIVSLFEG   420
TNSSLTAAVV VVTGLIGANF VQVVLDKLRL RDPIARGIAT ASSAHGLGTA ALSAKEPEAL   480
PFCAIAYALT GIFGSLLCSV PAVRQSLLAV VG                                 512

SEQ ID NO: 89         moltype = AA   length = 311
FEATURE               Location/Qualifiers
source                1..311
                      mol_type = protein
                      organism = Zea mays
SEQUENCE: 89
MARNEEKAQS MLNRFITMKQ EEKRKPRERR PYLASECRDL ADAERWRSEI LREIGAKVAE    60
IQNEGLGEHR LRDLNDEINK LLRERGHWER RIVELGGRDY SRSSNAPLMT DLDGNIVAVP   120
NPSGRGPGYR YFGAARKLPG VRELFDKPPE MRKRRTRYEI HKRINAGYYG YYDDEDGVLE   180
RLEGPAEKRM REEIVSEWHR VERVRREAMK GVMSGEVAAA GGRSGEAARE VLFEGVEEEV   240
EEERKREEEK REREKGEEVG REFVAHVPLP DEKEIERMVL ERKKKELLSK YASDSLLVEQ   300
EEAKEMLNVR R                                                       311

SEQ ID NO: 90         moltype = AA   length = 309
FEATURE               Location/Qualifiers
source                1..309
                      mol_type = protein
                      organism = Sorghum bicolor
SEQUENCE: 90
MARNEEKAQS MLNRFITMKQ EEKRKPRERR PYLASECRDL ADAERWRSEI LREIGAKVAE    60
IQNEGLGEHR LRDLNDEINK LLRERGHWER RIVELGGRDY SRSSNAPLMT DLDGNIVAVP   120
NPSGRGPGYR YFGAARKLPG VRELFDKPPE MRKRRTRYEI HKRINAGYYG YYDDEDGVLE   180
RLEAPAEKRM REEIVSEWHR VERVRREAMK GVVSGEVAAA GGRSGEAARE VLFEGVEEEV   240
EEERKREEEK REREKGEEAE FVAHVPLPDE KEIERMVLER KKKELLSKYA SDSLLVEQEE   300
AKEMLNVRR                                                          309
```

```
SEQ ID NO: 91           moltype = AA  length = 453
FEATURE                 Location/Qualifiers
VARIANT                 327
                        note = Xaa can be any naturally occurring amino acid
source                  1..453
                        mol_type = protein
                        organism = Arabidopsis thaliana
SEQUENCE: 91
MAKVYWPYFD PEYENLSSRI NPPSVSIDNT SCKECTLVKV DSMNKPGILL EVVQVLTDLD    60
LTITKAYISS DGGWFMDVFH VTDQQGNKVT DSKTIDYIEK VLGPKGHASA SQNTWPGKRV   120
GVHSLGDHTS IEIIARDRPG LLSEVSAVLA DLNINVVAAE AWTHNRRIAC VLYVNDNATS   180
RAVDDPERLS SMEEQLNNVL RGCEEQDEKF ARTSLSIGST HVDRRLHQMF FADRDYEAVT   240
KLDDSASCGF EPKITVEHCE EKGYSVINVS CEDRPKLMFD IVCTLTDMQY IVFHATISSS   300
GSHASQEYFI RHKDGCTLDT EGEKERXVKC LEAAIHRRVS EGWSLELCAK DRVGLLSEVT   360
RILREHGLSV SRAGVTTVGE QAVNVFYVKD ASGNPVDVKT IEALRGEIGH SMMIDFKNKV   420
PSRKWKEEGQ AGTGGGWAKT SFFFGNLLEK LLP                                453

SEQ ID NO: 92           moltype = AA  length = 143
FEATURE                 Location/Qualifiers
source                  1..143
                        mol_type = protein
                        organism = Arabidopsis thaliana
SEQUENCE: 92
MQELGLQRFS NDVVRLDLTP PSQTSSTSLS IDEEESTEAK IRRLISEHPV IIFSRSSCCM    60
CHVMKRLLAT IGVIPTVIEL DDHEVSSLPT ALQDEYSGGV SVVGPPPAVF IGRECVGGLE   120
SLVALHLSGQ LVPKLVQVGA LWV                                           143

SEQ ID NO: 93           moltype = AA  length = 942
FEATURE                 Location/Qualifiers
source                  1..942
                        mol_type = protein
                        organism = Zea mays
SEQUENCE: 93
MEGDDFTPEG GKLPEFKLDA RQAQGFISFF KKLPQDPRAV RLFDRRDYYT AHGENATFIA    60
RTYYHTMSAL RQLGSSSDGI LSASVSKAMF ETIARNILLE RTDCTLELYE GSGSNWRLTK   120
SGTPGNIGSF EDILFANNDM EDSPVIVALF PACRESQLYV GLSFLDMTNR KLGLAEFPED   180
SRFTNVESAL VALGCKECLL PADCEKSIDL NPLQDVISNC NVLLTEKKKA DPKSRDLAQD   240
LGRIIRGSVE PVRDLLSQFD YALGPLGALL SYAELLADDT NYGNYTIEKY NLNCYMRLDS   300
AAVRALNIAE GKTDVNKNFS LFGLMNRTCT VGMGKRLLNR WLKQPLLDVN EINNRLDMVQ   360
AFVEDPELRQ GLRQQLKRIS DIDRLTHSLR KKSANLQPVV KLYQSCSRIP YIKGILQQYN   420
GQFSTLIRSK FLEPLEEWMA KNRFGRFSSL VETAIDLAQL ENGEYRISPL YSSDLGVLKD   480
ELSVVENHIN NLHVDTASDL DLSVDKQLKL EKGSLGHVFR MSKKEEQKVR KKLTGSYLII   540
ETRKDGVKFT NSKLKNLSDQ YQALFGEYTS CQKKVVGDVV RVSGTFSEVF ENFAAVLSEL   600
DVLQSFADLA TSCPVPYVRP DITASDEGDI VLLGSRHPCL EAQDGVNFIP NDCTLVRGKS   660
WFQIITGPNM GGKSTFIRQV GVNVLMAQVG SFVPCDQASI SVRDCIFARV GAGDCQLHGV   720
STFMQEMLET ASILKGASDK SLIIIDELGR GTSTYDGFQML AWAICEHLME VTRAPTLFAT   780
HFHELTALAH RNDDEHQHIS DIGVANYHVG AHIDPLSRKL TMLYKVEPGA CDQSFGIHVA   840
EFANFPEAVV ALAKSKAAEL EDFSTTPTFS DDLKDEVGSK RKRVFSPDDI TRGAARARLF   900
LEEFAALPMD EMDGSKILEM ATKMKADLQK DAADNPWLQQ FF                      942

SEQ ID NO: 94           moltype = AA  length = 942
FEATURE                 Location/Qualifiers
source                  1..942
                        mol_type = protein
                        organism = Sorghum bicolor
SEQUENCE: 94
MEGDDFTPEG GKLPEFKLDA RQAQGFISFF KRLPQDPRAV RLFDRRDYYT AHGENATFIA    60
RTYYHTMSAL RQLGSSSDGI SSVSVSKAMF ETIARNILLE RTDCTLELYE GSGSNWRLTK   120
SGTPGNIGSF EDLLFANNDM QDSPVIVALF PVCRESQLYV GLSFLDMTNR KLGLAEFPED   180
SRFTNVESAL VALGCKECLL SEDCEKSIDL NPLRDAISNC NVLLTVKKKA DPKSRDLAQD   240
LGRIIRGSVE PVRDLLSQFD YALGPLGALL SYAELLADDT NYGNYTIEKY NLNCYMRLDS   300
AAVRALNISE RKTDVNKNFS LFGLMNRTCT VGMGKRLLNR WLKQPLLDVN EINNRLDMVQ   360
AFVEDPELRQ GLRQQLKRIS DIDRLTHALR KKSATLQPVV KLYQSCCRIS YIKGILEQYN   420
GQFSTLIRSK FLEPLEEWMA EDRFGRFSSL VETTIDLGQL ENGEYRISPL YSSDLGVLKD   480
ELSVVENHIN NLHVDTASDL DLSVDKQLKL EKGPLGHVFR MSKKEEQKVR KKLTGSYLII   540
ETRKDGVKFT SSKLKKLSDQ YQALFAEYTS CQKKVVGDVV RVSGSYSEVF ENFAAVLSEL   600
DVLQSFADLA TSCPVPYVRP DITVSDEGDI VLLGSRHPCL EAQDGVNFIP NDCTLVRGKS   660
WFQIITGPNM GGKSTFIRQV GVNVLMAQVG SFVPCDQASV SVRDCIFARV GAGDCQLHGV   720
STFMQEMLET ASILKGASDK SLIIIDELGR GTSTYDGFGL AWAICEHLME VTRAPTLFAT   780
HFHELTALAH KNDDEHQRVS NIGIANYHVG AHIDPSSRKL TMLYKVEPGA CDQSFGIHVA   840
EFANFPEAVV ALAKSKAAEL EDFSTTPTFS DDSKDEVGSK RKRVFSPDDV TRGAARARLF   900
LEDFAALPVD EMDRSKIVEM VTKMKSDLQK DAADNPWLQQ FF                      942

SEQ ID NO: 95           moltype = AA  length = 274
FEATURE                 Location/Qualifiers
source                  1..274
                        mol_type = protein
                        organism = Glycine max
```

```
SEQUENCE: 95
MRAKLFVFPI RGRNWCFSRT IDHSLSASHA SSQSPSTLKD LWTNINVGDK PLNTKTELFV    60
DYIANKMNNA WIGLEKAPEG SFKNKIHGLG LRLLSRVKPS EIFLKSISKE ITSVEIIYPS   120
SLNAQLVRRR LRHIAVRGAV IHRNYLYGLV SLIPLTSALS ILPLPNVPFF WVLFRTYSHW   180
RALQGSERLF QLVSDNSKTS NTCTYEKKTE HKESKSQRHS SNEPCWVLRP SKELENLVHL   240
EDGQESFSQH AIINICKIYD LNPVDVIKYE KSVF                              274

SEQ ID NO: 96            moltype = AA  length = 390
FEATURE                  Location/Qualifiers
source                   1..390
                         mol_type = protein
                         organism = Zea mays
SEQUENCE: 96
MQSAAAIGLL RPCAARPLAA YTSPRRGAGA CSGGTQPIIT PRGIRLSARP GLVPASPLEE    60
KENRRCRASM HAAASAGEEA GGGLAKTLQL GALFGLWYLF NIYFNIYNKQ VLKVLPYPIN   120
ITTVQFAVGS AIALFMWITG IHKRPKISGA QLFAILPLAI VHTMGNLFTN MSLGKVAVSF   180
THTIKAMEPF FSVLLSAIFL GELPTPWVVL SLLPIVGGVA LASLTEASFN WAGFWSAMAS   240
NVTFQSRNVL SKKLMVKKEE SLDNINLFSI ITVMSFFLLA PVTLLTEGVK VSPAVLQSAG   300
LNLKQVYTRS LIAAFCFHAY QQVSYMILAR VSPVTHSVGN CVKRVVVIVT SVLFFRTPVS   360
PINSLGTGIA LAGVFLYSQL KRLKPKPKTA                                   390

SEQ ID NO: 97            moltype = DNA  length = 2092
FEATURE                  Location/Qualifiers
source                   1..2092
                         mol_type = other DNA
                         note = Cold inducible promoter
                         organism = synthetic construct
SEQUENCE: 97
cagatccacg ctcgctcggg tgtcgggtca gatcgatcca gttggcgcac gtaataatcc    60
ttttcccag aaggagtcga accccctcctc ccgtccaat caatcaaag cgaccaatcg    120
actggctgtc ctacacacac acaaaaccga ccgaggcgac acaccgcagc agtgatcatt   180
ctgagcattt gcagaaaaag gagaacgtcc cgaaatcctg gtggttgtat tgtgtgattg   240
ctcactcagt ccgtgcaggg tcagggtgaa gccaagccaa caacccaacg ctcgctggga   300
gtagggtcca ccggatttat tggcagtaca tcgctccttg gtcctcctgc ccttcgctta   360
tttttaatt cggcagacgt gcacagacag ggcaccaccg gaccaaggaa gggcgcacac   420
cgtcgtcagt caccaggtgg gtgtgatcag cagccgcttc tcttgtgctg ctttatagcg   480
tatgaaattc cagtgtccct gttccacctg catgcaattg gtttgactga acaacatgat   540
agcaagtgat actatatata tttttataga ggaacacagt gaaaaaatat ttagtattat   600
tacgtgcatg aaattgtatt cacagttatc cctgatgcaa cgcaattgct caatatatag   660
cagtatatat tatacgaagt atatatgtat atctaatttt atgagaccgg gagaaggtgt   720
attcacagta cagtgcaggg ccatggccat gcagcccttg gggcctgaaa agggtcgcgt   780
gaagtggcca acgctgtgca attgcaacca acaaactttt tggtggcggg gtccctgtcc   840
ctggccggct ttgcccacag gccacagcgc atcacaccac cgctttatag cgcaccccca   900
ccacctcgt ctctcccccc gtcgagcaca caacacaccc tcctcgtcct ccaatccaat    960
caacctggta gactcgcttc gcttctcccc ccagctcgga cggagctcct cgcagcagcc   1020
gccgatcaac ctgcgctcgg gctcagcgct ggaaggtgag agctcagtgc ctcgtcccgc   1080
ccgccccaaa tctggttctt gtgctggctc tggctgtcgc ctgcacgaat tctgcatctg   1140
gttctttcga gacgcaattc ccggaccgtg gctttggtt tcggaggggg ccgagagtaa   1200
ggcgttagga ctttctccga gctgcaaggc cgctcgtcgt tgcggcattt ttcgtttcgc   1260
ttgtcctgtg atgagagatg tgcatttccc tttggcgggc ttaccgttcc ctgctcgtct   1320
gtatgtgtgt atgttttgtgt gacctttccc tcaacgccag gctcttcctc cctcttgctg   1380
tttcttcag cagtacagac gcgcatctgt acagcgcctt tcttcggtcc tgggttatga   1440
ttgatccgtt aacagttggt caccaagtgc tggctgttta atatgtacta taagcttctt   1500
ggtgccgctg cctctgccta tacgacttta tgcgctgcct gcacaagtct cagccatctg   1560
tgggaacgtg tgtctctcac ctacctttca tattgcactg gctggattga atcattctgc   1620
tttggagaga tgtccggtca ttttttttta aatcattttc atctcgcgta ctagttttg   1680
ttttgttttg cgagagagta atttttttt aatatttact gtctcctgtc ccatttgctg   1740
tttctttacc cagaaatttc caccagattc agtcaaacga aactcctgtg ctctttttt   1800
tctccctttc aaaagggtgt gtaaccgact accgactcag ataataaag tcggtcaca   1860
tatcacatga tatcatctcg cctctctccc ttctcctgtg ttttattttc cttttttca   1920
accacagcgt gatgaacttc tttttttttt gggggggggg ggggggtaa ctacagctta   1980
gcgaacatga atgggtagtt ttacaactaa tgcaacggct ggttcactga caactgtag   2040
gtgttggaag agaatagcct gaaggttcac agtaaccttc atctgtcgga ag          2092

SEQ ID NO: 98            moltype = DNA  length = 2516
FEATURE                  Location/Qualifiers
source                   1..2516
                         mol_type = other DNA
                         note = Seed preferred promoter
                         organism = synthetic construct
SEQUENCE: 98
acactttat tatcgcgtca aatcagtacc tcaatcgata ttgtagccta gtgttcttat    60
taaatgggaa gaattcgagg acacactaat tccttgctaa cacacactta tgctccattt   120
ggatgtcgat attggaggc atggaactga attggtttca attacaaatc agccatgata   180
ttgtaatgag atgtaatttc aattctattc tttggatgtc actgaattgg agtttggaat   240
tgtgtggtcc aattccacct tatatagaag agggatgctc tgtattggga gagtgagttt   300
ctagttatag tctagcttcg ggaaattgag tctcgttc caaatctcaa ttccatgtgc    360
aaccaaacaa tagaattctg gaaagctgat tccaattcct aattccgtgc tccaatatct   420
acatccaaac gggtgttaca taaatataga aatgacatat caaccatgca aaaccacatt   480
```

-continued

```
ggcgatgttg aacaaaggcg aacacccaca tactatgtac cgcacacggc atctctttct    540
caaaggtcga accacgtgtg ttccatgcat gcgtggaaca tgcaaggttg tcacgtatag    600
ggaatgatga cacacgagag cgcctacaag gcaacaaaca ccttacgtac cacgtagagt    660
gcattttgct accacctgcc accggatgac atgtatgcat gcatgcgttg tgtacgcata    720
cactgctgtc tgctggtgcc caaagaccat ctagaacagc atcttttaat tctccatttc    780
cctcacgcca ttgctagtgc cttgcacatg ctcgcactcc ctaacacatc ttcctcccctt   840
tatttttcgt tgccaattgc tagttgttca aatgccacgt tttccttaca cagctgtagg    900
gcaccgtacc acgtagaatg cattcctcgc caccaacaga caacacgcc gggcatatgt     960
acgtcttacg ccggaccatc accagtatat atgatgctag ggatcagtgg gcgcccttt    1020
tgcctcgtcc tcccggggcg gcattcctat gtcctaactg aagcaaccca cgcgccgcca   1080
tttctgttgc gaatgagtcc atggacatat gtgccaacag aaccctcgg aaggcaccat    1140
ctatctatct atctctcaag caatattata tttggcacct acgctcaagt acatagacag   1200
tgtgcacggc attgtgcagc tggaaagccc gcccgcacg agggctgcca aatcgacagc    1260
tccgcgccct tggaaatcct agtcacttgt tcacaattgc ccaatctacc cttgaagcac   1320
acggtggatg gtactgccac atttggctta tagggcata gaggacaatg aatgcaactg    1380
gagcgggaag gagagcttta atttgtaagt actcggtgaa cacggcacct gatgatgatg   1440
atgatggaca gcgaggaatt gttataaaag gcgcccgtcc ctcccatggc tcaagaacaa    1500
gggaatcgaa gccattcccct cttcaagagg ggatcatcag attgggctta ttattccta    1560
ttactccagg taattcttag tttgttgccc ttccaaacct ttacatctca tataagaatg   1620
attattacat gcaagattat gttgacatgc gtcgtcatgg tatttttttt aggcaaggat   1680
cggagttgct ctgaattgac tgaaccagat ctaccgtctt cggtacgcgc tcactccgcc   1740
ctctgccttt gttactgcca cgtttctctg aatgctctct tgtgtggtga ttgctgagag   1800
tggtttagct ggatctagaa ttacactctg aaatcgtgtt ctgcctgtgc tgattacttg   1860
ccgtcctttg tagcagcaaa atataggac atggtagtac gaaacgaaga tagaacctac     1920
acagcaatac gagaaatgtg taatttgtg cttagcggta tttatttaag cacatgttgg    1980
tgttataggg cacttggatt cagaagtttg ctgttaattt aggcacaggc ttcatactac   2040
atgggtcaat agtataggga ttcatattat aggcgatact ataataattt gttcgtctgc   2100
agagcttatt atttgccaaa attagatatt cctattctgt ttttgttgt gtgctgttaa    2160
attgttaacg cctgaaggaa taaatataaa tgacgaaatt ttgatgttta tctctgctcc    2220
tttattgtga ccataagtca agatcagatg cacttgtttt aaatattgtt gtctgaagaa    2280
ataagtactg acagtatttt gatgcattga tctgcttgtt tgttgtaaca aaatttaaaa    2340
ataaagagtt tccttttttgt tgctctcctt acctcctgat ggtatctagt atctaccaac    2400
tgacactata ttgcttctct ttacatacgt atcttgctcg atgccttctc cctagtgttg    2460
accagtgtta ctcacatagt ctttgctcat ttcattgtaa tgcagatacc aagcgg       2516
```

SEQ ID NO: 99         moltype = DNA   length = 1761
FEATURE               Location/Qualifiers
source                1..1761
                      mol_type = other DNA
                      note = Leaf preferred promoter
                      organism = synthetic construct
SEQUENCE: 99

```
gacatggagg tggaaggcct gacgtagata gagaagatgc tcttagcttt cattgtcttt     60
cttttgtagt catctgattt acctctctcg tttatacaac tggttttttta aacactcctt    120
aactttttcaa attgtctctt tctttacccct agactagata attttaatgg tgattttgct   180
aatgtggcgc catgttagat agaggtaaaa tgaactagtt aaaagctcag agtgataaat    240
caggctctca aaaattcata aactgttttta taaatatcca aatattttta catggaaaat    300
aataaaattt agtttagtat taaaaaattc agttgaatat agttttgtct tcaaaaatta    360
tgaaactgat cttaattatt ttccttaaaa accgtgctct atctttgatg tctagtttga   420
gacgattata taatttttttt tgtgcttaac tacgacgagc tgaagtacgt agaaatacta   480
gtggagtcgt gccgcgtgtg cctgtagcca ctcgtacgct acagcccagg cgctagagcc   540
caagaggccg gaggtggaag gcgtcgcggc actatagcca ctcgccgcaa gagcccaaga   600
gaccggagct ggaaggatga gggtctgggt gttcacgaat tgcctggagg caggaggctc   660
gtcgtccgga gccacaggcg tggagacgtc cgggataagg tgagcagccg ctgcgatagg   720
ggcgcgtgtg aaccccgtcg cgccccacgg atggtataag aataaaggca ttccgcgtcg   780
aggattcacc cgttcgcctc tcacctttttc gctgtactca ctcgccacac acacccctc    840
tccagctccg ttggagctcc ggacagcagc aggcgcgggg cggtcacgta gtaagcagct   900
ctcggctccc tctcccccttg ctccatttga tagtgcaacc catcgagcta cgggcccacc   960
gtcttcggta cgcgctcact ccgccctctg cctttgttac tgccacgttt tgctgaatgc   1020
tctcttgtgt ggtgattgct gagagtggtt tagctggatc tagaattaca ctctgaaatc   1080
gtgttctgcc tgtgctgatt acttgccgtc ctttgtagca gcaaatata gggacatggt     1140
agtacgaaac gaagatagaa cctacacagc aatacgagaa atgtgtaatt tggtgctag    1200
cggtatttat ttaagcacat gttggtgtta tagggcactt ggattcagaa gtttgctgtt   1260
aatttaggca caggcttcat actacatggg tcaatagtat agggattcat attataggcg   1320
atactataat aatttgttcg tctgcagagc ttattatttg ccaaattag atattcctat    1380
tctgttttttg tttgtgtgct gttaaattgt taacgcctga aggaataaat ataaatgacg   1440
aaattttgat gttttatctct gctcctttat tgtgaccata agtcaagatc agatgcactt   1500
gttttaaata ttgtgttctg aagaaataag tactgacagt attttgatgc attgatctgc    1560
ttgttttgttg taacaaaatt taaaaataaa gagtttcctt tttgtctc tccttacctc    1620
ctgatggtat ctagtatcta ccaactgaca ctatattgct tctctttaca tacgtatctt   1680
gctcgatgcc ttctccctag tgttgaccag tgttactcac atagtctttg ctcatttcat   1740
tgtaatgcag ataccaagcg g                                             1761
```

SEQ ID NO: 100        moltype = DNA   length = 2924
FEATURE               Location/Qualifiers
source                1..2924
                      mol_type = other DNA
                      note = Leaf preferred promoter
                      organism = synthetic construct

```
SEQUENCE: 100
atgtgctggt gccccataag gtaggcacct aggtctgtgt ttgaagcatc gacagatttg    60
taaacatgtt cctatgaacc tatttctgat tgataatttg tcaaaactca tcatttgtct   120
tcatccttgc ctgcttgcgt tcacgtgaca aagtacgtgt atgtcttcgg cctttgctgt   180
gtatgtttcg cattgcttag atgtggtgaa agaacatcag aagatgcatt gatggcgtgc   240
ttaaaccagt gatgtgctcc aggtgttcct gcagtctgca gagatattta ctcttgtagt   300
cttgttgaca gcacagttgt atgtgatttc ttggatgtaa tgtaaaccaa atgaaagata   360
ggaacagttc gtcctcttcc gtatacgaag gtcactgtat catttgtcgt ggcacaagat   420
gatctgcagg caggactgca acatggtttc ttggactgtc ctgaatgccc gttcttgttc   480
tttagttgag ccagagcagc agcctggtgt cggtgcctga gacctgacga agcacacggc   540
aaacaaacaa gtcgcagcag ctagcagggg cgttgccatc gccacaagcc cccaagagac   600
ccgccgagga aaagaaaaaa aaactacggc cgccgttgcc aagccgagcg tgcgaaccga   660
tccacgatg ggagatcaga gatcacccac cgcaggcggg cggcagtggc tggcgaggtg    720
cgtccacaga acctgctgca ggtccctgtc cgtcccgggg acccctttc taggcgagca    780
actccccatg gcagagctgc acgcagcagg gcccgtcgtt ggttgcagct ttaacccttt    840
ttgttttaac catacaatgc agagtcgcag aggtgaaaca ggacgaaat tacagaaaag    900
atggtggtgt gccagcagcc ccagcatgaa gaagatcagg acaaaagaaa agcttgtgat   960
tggtgacagc aacaggattg gattggagcc aagctaggca gtgagaggca ggcagcaaga  1020
cgcgtcagcc actgaaatcc agagggcaac ctcggcctca caactcatat ccccttgtgc  1080
tgttgcgcgc cgtggttagc caggtgtgct gcaggggta ccatggcatg catcgataga   1140
tctcgaggga tccaaagaca tggaggtgga aggcctgacg tagatagaga agatgctctt  1200
agcttcatt gtctttcttt tgtagtcatc tgatttacct ctctcgttta tcaactagt    1260
tttttaaaca ctccttaact tttcaaattg tctctttctt tacctgacc tagatatt     1320
taatggtgat tttgctaatg tggcgccatg ttagatagag gtaaaatgaa ctagttaaaa  1380
gctcagagtg ataaatcagg ctctcaaaaa ttcataaact gtttttaaa tatccaaata   1440
tttttacatg gaaaataata aaatttagtt tagtattaaa aaattcagtt gaatatagtt  1500
ttgtcttcaa aaattatgaa actgatctta attattttc cttaaaaccg tgctctatct   1560
ttgatgtcta gtttgagacg attatataat tttttttgtg cttaactacg acgagctgaa  1620
gtacgtagaa atactagtgg agtcgtgccg cgtgtgcctg tagccactcg tacgctacag  1680
cccaagcgct agagcccaag aggcggagg tggaaggcgt cgcggcacta tagccactcg   1740
ccgcaagagc ccaagagacc ggagctggaa ggatgagggt ctgggtgttc acgaattgcc  1800
tggaggcagg aggctcgtcg tccggagcca caggcgtgga gacgtccggg ataaggtgag  1860
cagccgctgc gataggggcg cgtgtgaacc ccgtcgcgcc ccacgcgatgg tataagaata  1920
aaggcattcc gcgtgcagga ttcacccgtt cgcctctcac cttttcgctg tactcactcg   1980
ccacacacac ccctctcca gctccgttgg agctccggac agcagcaggc gcggggcggt   2040
cacgtagtaa gcagctctcg gctccctctc ccttgctcc atttgatagt gcaacccatc    2100
gagctacacc ggtgcggccc accgtcttcg gtacgcgctc actccgccct ctgcctttgt   2160
tactgccacg tttctctgaa tgctctcttg tgtggtgatt gctgagagtg gtttagctgg    2220
atctagaatt acactctgaa atcgtgtct gcctgtgctg attacttgcc gtcctttgta   2280
gcagcaaaat ataggggacat ggtagtacga aacgaagata gaacctacac agcaatacga  2340
gaaatgtgta atttggtgct tagcggtatt tatttaagca catgtggtg ttatagggca    2400
cttggattca gaagtttgct gttaatttag gcacaggctt catactacat gggtcaatag   2460
tatagggatt catatttag gcgatactat aataatttgt tcgtctgcag agcttattat    2520
ttgccaaaat tagatattcc tattctgttt ttgtttgtgt gctgttaaat tgttaacgcc   2580
tgaaggaata aatataaatg acgaaatttt gatgtttatc tctgctcctt tatttgtgacc  2640
ataagtcaag atcagatgca cttgttttaa atattgttgt ctgaagaaat aagtactgac   2700
agtattttga tgcattgatc tgcttgtttg ttgtaacaaa atttaaaaat aaagagtttc   2760
cttttttgttg ctctccttac ctcctgatgg tatctagtat ctaccaactg acactatatt  2820
gcttctcttt acatacgtat cttgctcgat gccttctccc tagtgttgac cagtgttact   2880
cacatagtct ttgctcattt cattgtaatg cagataccaa gcgg                    2924

SEQ ID NO: 101          moltype = DNA   length = 408
FEATURE                 Location/Qualifiers
source                  1..408
                        mol_type = unassigned DNA
                        organism = Oryza sativa
SEQUENCE: 101
ggcagagccg tgcccgtctc atcccctgcc cgtgcaagca gctaggtagg acgatttgag    60
cgtggtgtta ggccgaaccg ctgaaggaag attgctccac tgttgactgc attaggattc   120
aatccttgct gctaaatgta ttgcttatat tcagcaatat aatgttcagc agcaagaact   180
ggatcttaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggtttcag tttacctaat ttatggtctg tacccatgaa   360
aagtgggaaa aggctgaaga attcgatttc tttctttctt tcaatgtt               408

SEQ ID NO: 102          moltype = DNA   length = 325
FEATURE                 Location/Qualifiers
source                  1..325
                        mol_type = unassigned DNA
                        organism = Oryza sativa
SEQUENCE: 102
ggcagagccg tgcccgtctc atcccctgcc cgtgcaagca gctaggtagg acgatttgag    60
cgtggtgtta ggccgaaccg ctgaaggaag attgctccac tgttgactgc attaggattc   120
aatccttgct gctaaatgta ttgcttatat tcagcaatat aatgttcagc agcaagaact   180
ggatcttaat atagtcgata gtggaagaac ggtaacatat gtggtttgca gcaggtgagc   240
aggatgggtg tggatgattg aatatctctg ttcagtgttt tcatcatctg actgaacact   300
gaatcagctt gctgacgtta gaggt                                         325

SEQ ID NO: 103          moltype = DNA   length = 280
```

```
FEATURE              Location/Qualifiers
source               1..280
                     mol_type = unassigned DNA
                     organism = Oryza sativa
SEQUENCE: 103
ggcagagccg tgcccgtctc atccctgcc cgtgcaagca gctaggtagg acgatttgag    60
cgtggtgtta ggccgaaccg ctgaaggaag attgctccac tgttgactgc attaggattc  120
aatccttgct gctaaatgta ttgcttatat tcagcaatat aatgttcagc agcaagaact  180
ggatcttaat atagtcgata gtggaagaac ggtaacatat gtggtttgca gcaggtgagc  240
aggatgggtg tggatgattg aatatctctg ttcagtgttt                        280

SEQ ID NO: 104       moltype = DNA  length = 249
FEATURE              Location/Qualifiers
source               1..249
                     mol_type = unassigned DNA
                     organism = Oryza sativa
SEQUENCE: 104
ggcagagccg tgcccgtctc atccctgcc cgtgcaagca gctaggtagg acgatttgag    60
cgtggtgtta ggccgaaccg ctgaaggaag attgctccac tgttgactgc attaggattc  120
aatccttgct gctaaatgta ttgcttatat tcagcaatat aatgttcagc agcaagaact  180
ggatcttaat atagtcgata gtggaagaac ggtaacatat gtggtttgca gcaggtgagc  240
aggatgggt                                                          249
```